US005856090A

United States Patent [19]

Epstein

[11] Patent Number: 5,856,090

[45] Date of Patent: Jan. 5, 1999

[54] DNA-METHYLASE LINKING REACTION

[75] Inventor: David M. Epstein, San Diego, Calif.

[73] Assignee: The Scripps Research Institute, La Jolla, Calif.

[21] Appl. No.: 305,764

[22] Filed: Sep. 9, 1994

[51] Int. Cl.[6] ............................ C12Q 1/68; G01N 33/53; C12N 15/09; C07H 21/04

[52] U.S. Cl. .............................. 435/6; 435/7.1; 435/69.7; 435/172.1; 435/320.1; 536/23.1

[58] Field of Search .............................. 435/6, 7.1, 172.1, 435/320.1, 69.7; 536/23.1

[56] References Cited

U.S. PATENT DOCUMENTS 5,223,409 6/1993 Ladner et al. .
5,270,170 12/1993 Schatz et al. .
5,302,518 4/1994 Neupert et al. ........................ 435/69.1

OTHER PUBLICATIONS

Smith et. al. Science, 228: 1315 (1985).
Barbas et al. Curr. Opin. Biotechnol. 4: 526 (1993).
Cuel et. al. Proc. Natl. Acad. Sci. USA. 89: 1865–1869 (92).
Schatz et al. Bio/Technology 11: 1138–1143 (1993).
Pluckthum et al. Angew. Chem. Intl. Ed. 30: 296 (1991).
Tuerk et. al. Science 249: 505 (1990).
Ellington, Nature 34: 818–822 (1990).
Thiesen et. al. Nucl. Acids Res. 18: 3203 (1990).
Wilson et. al. Annu. Rev. Genet. 25: 585–627 (1991).
Wu et. al. J. Biol. Chem. 262: 4778–4786 (1987).
Osterman et. al. Biochemistry 27: 5204–5210 (1988).
Santi et. al. Cell, 33: 9–10 (1983).
Finnegan et. al., 21: Nucl. Acids Res. 2383 (1993).
Ellison et. al. Proc. Natl. Acad. Sci. USA. 91: 7316 (1994).
Hatah et. al. J. Biol. Chem. 269: 18814 (1994).
Hughs et. al. Mol. Biochem. Parasitol. 58: 43–52 (1993).
Kilmasauskas et. al. Cell. 357–359 (1994).
Chem et. al. Biochemistry 30: 11018–11025 (1991).
Freidman et. al. J. Biol. Chem. 260: 5698 (1985).
Taylor et. al. Biochem. J. 291: 493–504 (1993).
Doskocil et. al. Biochim. Biophys. Acta. 145: 771 (1967).
Lin et. al. Nucleic acids Research 17: 3001, (1989).
Sugisaki et. al. J. of Biol. Chem. 266: 13952, (1991).
Slatko et. al. Gene 74, 45–50, (1988).
Friedman (1982) J. Bacteriol. 151: 262–268.
Sharma et al. (1987) Biotechnol. Appl. Biochem. 9: 181–193. (Abstract).

*Primary Examiner*—Jasemine C. Chambers
*Assistant Examiner*—Scott D. Priebe
*Attorney, Agent, or Firm*—Thomas Fitting; Emily Holmes

[57] ABSTRACT

The activity of sequence-specific DNA binder proteins, such as DNA methylases, provides a method of obtaining a covalent linkage between a nucleic acid segment and a polypeptide determinant encoded by the nucleic acid segment. The polypeptide determinant is expressed as a fusion protein together with the DNA methylase, which binds in vivo to a cytidine suicide analog when present in a nucleotide sequence. A plasmid suitable for use in this linkage reaction can comprise: (1) a gene fusion construct including a gene encoding a DNA methylase and a gene encoding a polypeptide determinant; (2) a promoter for transcription of the gene fusion construct as messenger RNA; and (3) a methylase conjugation element linked to the gene fusion sequence, the methylase conjugation element including a methylase binding site having at least one copy of a nucleotide sequence including a cytidine suicide analog capable of irreversibly binding the DNA methylase. The plasmid can form a plasmid-polypeptide determinant conjugate. The plasmids and methods of the present invention are useful for in vitro evolution of proteins.

51 Claims, 33 Drawing Sheets

Glutathione S-Transferase-MspI (K2Q) Methylase Gene Fusion and Protein Sequence.

```
250 cagtattcatgtcccctatactaggttattggaaaattaagggccttgtgcaacccactcgacttcttt 318
              METSerProIleLeuGlyTyrTrpLysIleLysGlyLeuValGlnProThrArgLeuLeuL
              Glutathione S-Transferase

319 tggaatatcttgaagaaaaatatgaagagcatttgtatgagcgcgatgaaggtgataaatggcgaaaca 387
    euGluTyrLeuGluGluLysTyrGluGluHisLeuTyrGluArgAspGluGlyAspLysTrpArgAsnL

388 aaaagtttgaattgggtttggagtttcccaatcttccttattatattgatggtgatgttaaattaacac 456
    ysLysPheGluLeuGlyLeuGluPheProAsnLeuProTyrTyrIleAspGlyAspValLysLeuThrG

457 agtctatggccatcatacgttatatagctgacaagcacaacatgttgggtggttgtccaaaagagcgtg 525
    lnSerMETAlaIleIleArgTyrIleAlaAspLysHisAsnMETLeuGlyGlyCysProLysGluArgA

526 cagagatttcaatgcttgaaggagcggttttggatattagatacggtgtttcgagaattgcatatagta 594
    laGluIleSerMETLeuGluGlyAlaValLeuAspIleArgTyrGlyValSerArgIleAlaTyrSerL

595 aagactttgaaactctcaaagttgattttcttagcaagctacctgaaatgctgaaaatgttcgaagatc 663
    ysAspPheGluThrLeuLysValAspPheLeuSerLysLeuProGluMETLeuLysMETPheGluAspA

664 gtttatgtcataaaacatatttaaatggtgatcatgtaacccatcctgacttcatgttgtatgacgctc 732
    rgLeuCysHisLysThrTyrLeuAsnGlyAspHisValThrHisProAspPheMETLeuTyrAspAlaL

733 ttgatgttgttttatacatggacccaatgtgcctggatgcgttcccaaaattagtttgttttaaaaaac 801
    euAspValValLeuTyrMETAspProMETCysLeuAspAlaPheProLysLeuValCysPheLysLysA
```

FIG. 3A

```
802  gtattgaagctatcccacaaattgataagtacttgaaatccagcaagtatatagcatggcctttgcagg  870
     rgIleGluAlaIleProGlnIleAspLysTyrLeuLysSerSerLysTyrIleAlaTrpProLeuGlnG

871  gctggcaagccacgtttggtggtggcgaccatcctccaaaatcggatatcgaaggtcgtgggatcgatc  939
     lyTrpGlnAlaThrPheGlyGlyGlyAspHisProProLysSerAspIleGluGlyArgGlyIleAspP
                                                             Factor X      Linker
                                                           Cleavage Site

940  cccccatgcaacctgaaatattgaaattgattcgtagtaaattggatctaactcaaaagcaagcatctg 1008
     roProMETGlnProGluIleLeuLysLeuIleArgSerLysLeuAspLeuThrGlnLysGlnAlaSerG
          MspI Methylase

1009 aaattattgaagttagtgataaaacatggcaacagtgggaatcaggtaaaacagaaatgcatcctgctt 1077
     luIleIleGluValSerAspLysThrTrpGlnGlnTrpGluSerGlyLysThrGluMETHisProAlaT

1078 attactcttttctccaagaaaaacttaaagataagattaactttgaggaactgagcgctcaaaaaacac 1146
     yrTyrSerPheLeuGlnGluLysLeuLysAspLysIleAsnPheGluGluLeuSerAlaGlnLysThrL

1147 tccaaaagaagatattcgataaatacaatcagaatcaaattactaaaaatgcggaagaattagctgaaa 1215
     euGlnLysLysIlePheAspLysTyrAsnGlnAsnGlnIleThrLysAsnAlaGluGluLeuAlaGluI

1216 ttactcatattgaagaaagaaaagatgcttatagcagtgatttcaaatttattgatttattttctggta 1284
     leThrHisIleGluGluArgLysAspAlaTyrSerSerAspPheLysPheIleAspLeuPheSerGlyI
```

FIG. 3B

```
1285 tcggtggaataaggcaatcattcgaagtgaatggcggaaaatgcgtcttttcgtctgaaatagatccct 1353
     leGlyGlyIleArgGlnSerPheGluValAsnGlyGlyLysCysValPheSerSerGluIleAspProP

1354 ttgcaaaatttacatattatacaaattttggtgtagtcccttttggagatattacaaaagttgaggcta 1422
     heAlaLysPheThrTyrTyrThrAsnPheGlyValValProPheGlyAspIleThrLysValGluAlaT

1423 caactattccacagcatgacattttatgtgcaggatttccgtgtcagccatttagccatattggtaaaa 1491
     hrThrIleProGlnHisAspIleLeuCysAlaGlyPheProCysGlnProPheSerHisIleGlyLysA

1492 gagaaggctttgaacatccaactcaaggaacaatgttccatgaaattgttcgtatcattgaaacaaaaa 1560
     rgGluGlyPheGluHisProThrGlnGlyThrMETPheHisGluIleValArgIleIleGluThrLysL

1561 aaaccccagttttatttctagaaaatgttcctggtctcattaatcatgatgacggaaatacattaaaag 1629
     ysThrProValLeuPheLeuGluAsnValProGlyLeuIleAsnHisAspAspGlyAsnThrLeuLysV

1630 tcatcattgaaacactagaagatatgggctacaaagttcatcatacggtactagacgctagtcattttg 1698
     alIleIleGluThrLeuGluAspMETGlyTyrLysValHisHisThrValLeuAspAlaSerHisPheG

1699 gtatcccacaaaaacgtaagcgtttttacttagtagctttcctaaatcaaaatattcactttgagtttc 1767
     lyIleProGlnLysArgLysArgPheTyrLeuValAlaPheLeuAsnGlnAsnIleHisPheGluPheP

1768 ctaaacctccaatgatttctaaagatatcggtgaagttttagaaagcgatgtaactggatatagcattt 1836
     roLysProProMETIleSerLysAspIleGlyGluValLeuGluSerAspValThrGlyTyrSerIleS
```

FIG. 3C

```
1837 cagagcatttacaaaaagttatctctttaaaaagatgatggtaaaccttctttaattgacaaaata 1905
     erGluHisLeuGlnLysSerTyrLeuPheLysLysAspAspGlyLysProSerLeuIleAspLysAsnT

1906 cgactggggcagttaaaacattagtttctacctatcacaaaattcaacgattaacaggtacttttgtta 1974
     hrThrGlyAlaValLysThrLeuValSerThrTyrHisLysIleGlnArgLeuThrGlyThrPheValL

1975 aggatggagaaacaggtatccgtcttttaacaacgaatgaatgcaaagctattatgggttttccaaaag 2043
     ysAspGlyGluThrGlyIleArgLeuLeuThrThrAsnGluCysLysAlaIleMETGlyPheProLysA

2044 atttgttattcctgtatcaagaactcagatgtaccgtcaaatgggtaactctgtcgtagttccggtgg 2112
     spPheValIleProValSerArgThrGlnMETTyrArgGlnMETGlyAsnSerValValValProValV

2113 ttacaaaaattgcagaacagattagtttggcactaaaaactgttaaccaacaatccccgcaagaaaact 2181
     alThrLysIleAlaGluGlnIleSerLeuAlaLeuLysThrValAsnGlnGlnSerProGlnGluAsnP

2182 ttgaattagaactcgtttaaaaaaatatagcccctaattgaggggctatttaacataaaatctcatat 2250
     heGluLeuGluLeuValStop

2251 acgaaattcagttagtagtgaacttttccgactatgatgttttcattgaaaaacatctataaaatcaat 2319

2320 taaatatattcaagaagtggaattc                                              2344
```

*Numbering is for the the nucleotide sequence and corresponds to the sequence of the parent pGEX-3X vector.

FIG. 3D

Wild Type MspI Methylase Gene and Protein Sequences

```
  1 atgaaacctgaaatattgaaattgattcgtagtaaattggatctaactcaaaagcaagcatctgaaatt   69
    METLysProGluIleLeuLysLeuIleArgSerLysLeuAspLeuThrGlnLysGlnAlaSerGluIle

 70 attgaagttagtgataaaacatggcaacagtgggaatcaggtaaaacagaaatgcatcctgcttattac  138
    IleGluValSerAspLysThrTrpGlnGlnTrpGluSerGlyLysThrGluMETHisProAlaTyrTyr

139 tcttttctccaagaaaaacttaaagataagattaactttgaggaactgagcgctcaaaaacactccaa  207
    SerPheLeuGlnGluLysLeuLysAspLysIleAsnPheGluGluLeuSerAlaGlnLysThrLeuGln

208 aagaagatattcgataaatacaatcagaatcaaattactaaaaatgcggaagaattagctgaaattact  276
    LysLysIlePheAspLysTyrAsnGlnAsnGlnIleThrLysAsnAlaGluGluLeuAlaGluIleThr

277 catattgaagaaagaaaagatgcttatagcagtgatttcaaatttattgatttattttctggtatcggt  345
    HisIleGluGluArgLysAspAlaTyrSerSerAspPheLysPheIleAspLeuPheSerGlyIleGly

346 ggaataaggcaatcattcgaagtgaatggcggaaaatgcgtcttttcgtctgaaatagatccctttgca  414
    GlyIleArgGlnSerPheGluValAsnGlyGlyLysCysValPheSerSerGluIleAspProPheAla
```

FIG. 4A

```
415 aaatttacatattatacaaattttggtgtagtcccttttggagatattacaaagttgaggctacaact 483
    LysPheThrTyrTyrThrAsnPheGlyValValProPheGlyAspIleThrLysValGluAlaThrThr

484 attccacagcatgacattttatgtgcaggatttccgtgtcagccatttagccatattggtaaaagagaa 552
    IleProGlnHisAspIleLeuCysAlaGlyPheProCysGlnProPheSerHisIleGlyLysArgGlu

553 ggctttgaacatccaactcaaggaacaatgttccatgaaattgttcgtatcattgaaacaaaaaaacc 621
    GlyPheGluHisProThrGlnGlyThrMETPheHisGluIleValArgIleIleGluThrLysLysThr

622 ccagttttatttctagaaaatgttcctggtctcattaatcatgatgacggaaatacattaaaagtcatc 690
    ProValLeuPheLeuGluAsnValProGlyLeuIleAsnHisAspAspGlyAsnThrLeuLysValIle

691 attgaaacactagaagatatgggctacaaagttcatcatacggtactagacgctagtcattttggtatc 759
    IleGluThrLeuGluAspMETGlyTyrLysValHisHisThrValLeuAspAlaSerHisPheGlyIle

760 ccacaaaaacgtaagcgtttttacttagtagctttcctaaatcaaaatattcactttgagtttcctaaa 828
    ProGlnLysArgLysArgPheTyrLeuValAlaPheLeuAsnGlnAsnIleHisPheGluPheProLys
```

FIG. 4B

```
829  cctccaatgatttctaaagatatcggtgaagttttagaaagcgatgtaactggatatagcatttcagag  897
     ProProMETIleSerLysAspIleGlyGluValLeuGluSerAspValThrGlyTyrSerIleSerGlu

898  catttacaaaaaagttatctctttaaaaagatgatggtaaaccttctttaattgacaaaaatacgact  966
     HisLeuGlnLysSerTyrLeuPheLysLysAspAspGlyLysProSerLeuIleAspLysAsnThrThr

967  ggggcagttaaaacattagtttctacctatcacaaaattcaacgattaacaggtacttttgttaaggat 1035
     GlyAlaValLysThrLeuValSerThrTyrHisLysIleGlnArgLeuThrGlyThrPheValLysAsp

1036 ggagaaacaggtatccgtcttttaacaacgaatgaatgcaaagctattatgggttttccaaaagatttt 1104
     GlyGluThrGlyIleArgLeuLeuThrThrAsnGluCysLysAlaIleMETGlyPheProLysAspPhe
```

FIG. 4C

```
1105 gttattcctgtatcaagaactcagatgtaccgtcaaatgggtaactctgtcgtagttccggtggttaca 1173
     ValIleProValSerArgThrGlnMETTyrArgGlnMETGlyAsnSerValValValProValValThr

1174 aaaattgcagaacagattagtttggcactaaaaactgttaaccaacaatccccgcaagaaaactttgaa 1242
     LysIleAlaGluGlnIleSerLeuAlaLeuLysThrValAsnGlnGlnSerProGlnGluAsnPheGlu

1243 ttagaactcgtttaaaaaaatatagcccctaattgaggggctatttaacataaaatctcatatacgaa 1311
     LeuGluLeuValStop

1312 attcagttagtagtgaacttttccgactatgatgttttcattgaaaaacatctataaaatcaattaaat 1380

1381 atattcaagaagtggaattc                                                   1400
```

FIG. 4D

Lys2-Gln (K2Q) MspI Methylase Gene and Protein Sequences

```
  1 atgcaacctgaaatattgaaattgattcgtagtaaattggatctaactcaaaagcaagcatctgaaatt  69
    METGlnProGluIleLeuLysLeuIleArgSerLysLeuAspLeuThrGlnLysGlnAlaSerGluIle

 70 attgaagttagtgataaaacatggcaacagtgggaatcaggtaaaacagaaatgcatcctgcttattac 138
    IleGluValSerAspLysThrTrpGlnGlnTrpGluSerGlyLysThrGluMETHisProAlaTyrTyr

139 tcttttctccaagaaaaacttaaagataagattaactttgaggaactgagcgctcaaaaaacactccaa 207
    SerPheLeuGlnGluLysLeuLysAspLysIleAsnPheGluGluLeuSerAlaGlnLysThrLeuGln

208 aagaagatattcgataaatacaatcagaatcaaattactaaaaatgcggaagaattagctgaaattact 276
    LysLysIlePheAspLysTyrAsnGlnAsnGlnIleThrLysAsnAlaGluGluLeuAlaGluIleThr

277 catattgaagaaagaaaagatgcttatagcagtgatttcaaatttattgatttattttctggtatcggt 345
    HisIleGluGluArgLysAspAlaTyrSerSerAspPheLysPheIleAspLeuPheSerGlyIleGly

346 ggaataaggcaatcattcgaagtgaatggcggaaaatgcgtcttttcgtctgaaatagatccctttgca 414
    GlyIleArgGlnSerPheGluValAsnGlyGlyLysCysValPheSerSerGluIleAspProPheAla
```

FIG. 5A

```
415 aaatttacatattatacaaattttggtgtagtcccttttggagatattacaaaagttgaggctacaact 483
    LysPheThrTyrTyrThrAsnPheGlyValValProPheGlyAspIleThrLysValGluAlaThrThr

484 attccacagcatgacattttatgtgcaggatttccgtgtcagccatttagccatattggtaaaagagaa 552
    IleProGlnHisAspIleLeuCysAlaGlyPheProCysGlnProPheSerHisIleGlyLysArgGlu

553 ggctttgaacatccaactcaaggaacaatgttccatgaaattgttcgtatcattgaaacaaaaaaacc 621
    GlyPheGluHisProThrGlnGlyThrMETPheHisGluIleValArgIleIleGluThrLysLysThr

622 ccagttttatttctagaaaatgttcctggtctcattaatcatgatgacggaaatacattaaaagtcatc 690
    ProValLeuPheLeuGluAsnValProGlyLeuIleAsnHisAspAspGlyAsnThrLeuLysValIle

691 attgaaacactagaagatatgggctacaaagttcatcatacggtactagacgctagtcattttggtatc 759
    IleGluThrLeuGluAspMETGlyTyrLysValHisHisThrValLeuAspAlaSerHisPheGlyIle

760 ccacaaaaacgtaagcgtttttacttagtagctttcctaaatcaaaatattcactttgagtttcctaaa 828
    ProGlnLysArgLysArgPheTyrLeuValAlaPheLeuAsnGlnAsnIleHisPheGluPheProLys
```

FIG. 5B

```
829  cctccaatgatttctaaagatatcggtgaagttttagaaagcgatgtaactggatatagcatttcagag  897
     ProProMETIleSerLysAspIleGlyGluValLeuGluSerAspValThrGlyTyrSerIleSerGlu

898  catttacaaaaaagttatctctttaaaaagatgatggtaaaccttctttaattgacaaaaatacgact  966
     HisLeuGlnLysSerTyrLeuPheLysLysAspAspGlyLysProSerLeuIleAspLysAsnThrThr

967  ggggcagttaaaacattagtttctacctatcacaaaattcaacgattaacaggtacttttgttaaggat 1035
     GlyAlaValLysThrLeuValSerThrTyrHisLysIleGlnArgLeuThrGlyThrPheValLysAsp

1036 ggagaaacaggtatccgtcttttaacaacgaatgaatgcaaagctattatgggttttccaaaagatttt 1104
     GlyGluThrGlyIleArgLeuLeuThrThrAsnGluCysLysAlaIleMETGlyPheProLysAspPhe
```

FIG. 5C

```
1105 gttattcctgtatcaagaactcagatgtaccgtcaaatgggtaactctgtcgtagttccggtggttaca 1173
     ValIleProValSerArgThrGlnMETTyrArgGlnMETGlyAsnSerValValValProValValThr

1174 aaaattgcagaacagattagtttggcactaaaaactgttaaccaacaatccccgcaagaaaactttgaa 1242
     LysIleAlaGluGlnIleSerLeuAlaLeuLysThrValAsnGlnGlnSerProGlnGluAsnPheGlu

1243 ttagaactcgtttaaaaaaatatagcccctaattgaggggctatttaacataaaatctcatatacgaa 1311
     LeuGluLeuValStop

1312 attcagttagtagtgaacttttccgactatgatgttttcattgaaaaacatctataaaatcaattaaat 1380

1381 atattcaagaagtggaattc                                                  1400
```

FIG. 5D

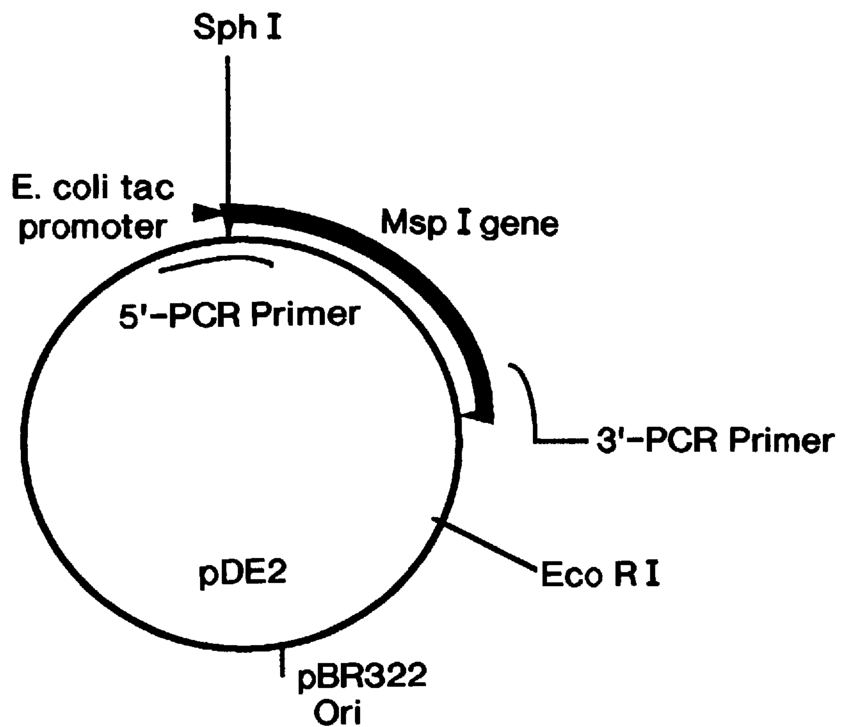
Polymerase Chain Reaction with 5'- and 3'-Primers
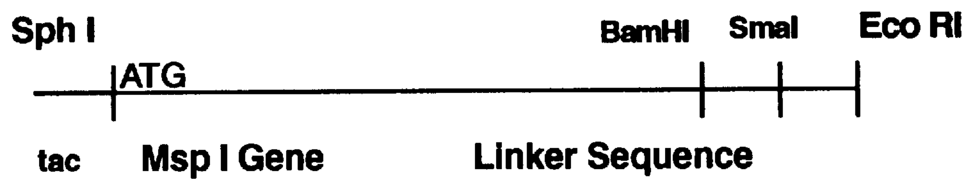
FIG. 10

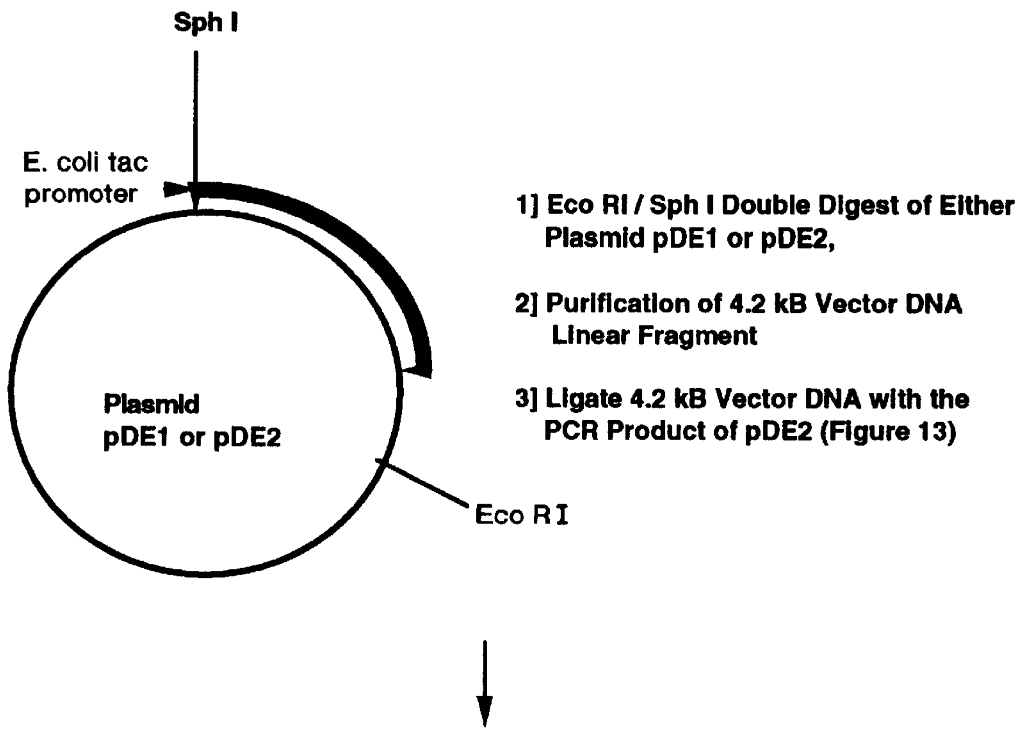
PCR Product From pDE2 (Figure 13)
Sph I BamHI SmaI Eco RI
ATG
tac Msp I Gene Linker Sequence
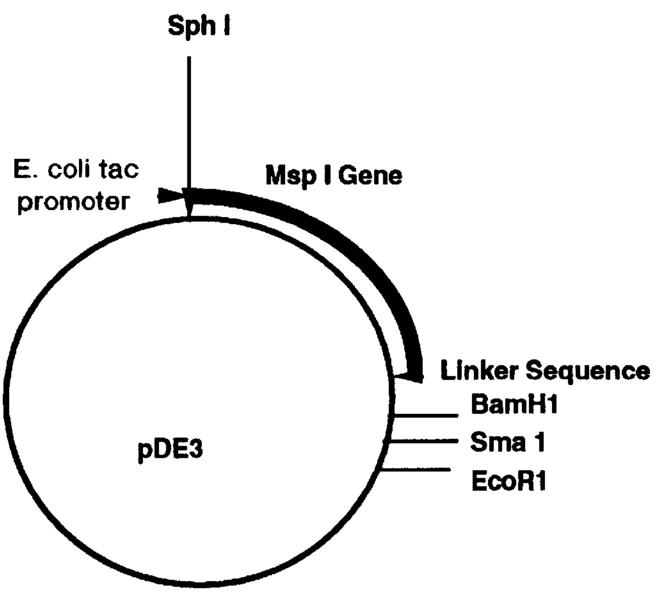
FIG. 11

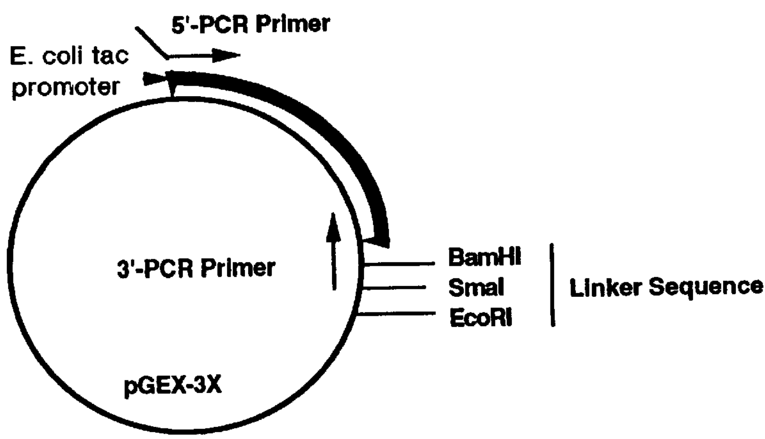
Polymerase Chain Reaction with 5'- and 3'- PCR Primers
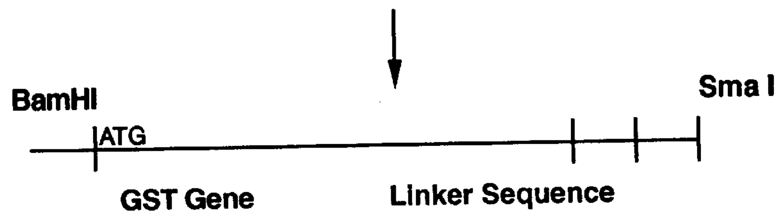
Digest PCR Product with BamHI and Ligate Into BamHI Digested pDE3
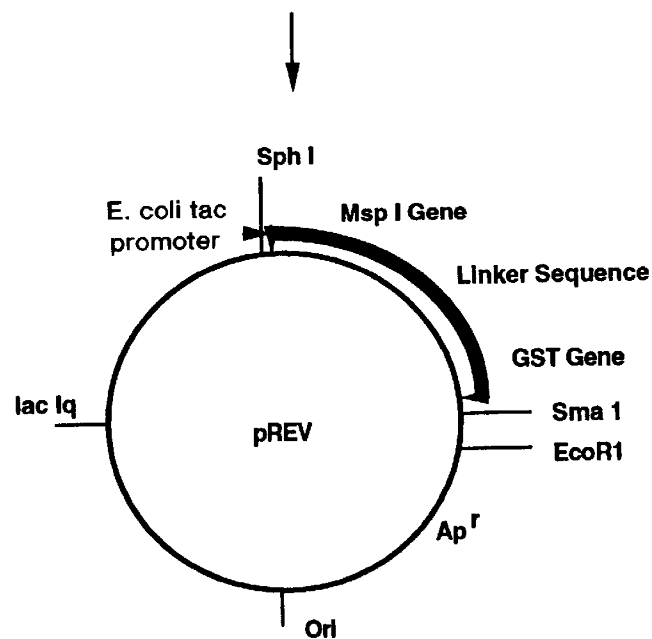
FIG. 12 n = 1 n = 2 n = 3 n = 4 n = 5 n = 6

```
G AATTCAGCGCTGCGCAGCGCTGCGCAGCGCTGCGCGAATTC
  CTTAAGTCGCGACGCGTCGCGACGCGTCGCGACGCGCTTAA G
```

FIG. 15 n = 1 n = 2 n = 3 n = 4 n = 5

```
G AATTCATCCGGATCCGGACCGGTCCGGATCCGGATGAATTC
  CTTAAGTAGGCCTAGGCCTGGCCAGGCCTAGGCCTACTTAA G
```

BamH I BamH I

FIG. 16

Covalent Plasmid Polypeptide Determinant Conjugate
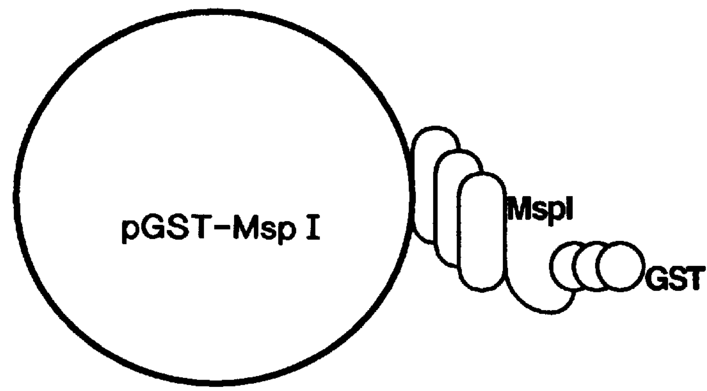
1] Affinity Selection of Novel GST Enzymes by Binding to Glutathione-Sepharose 4B or Immobilized GST Inhibitor
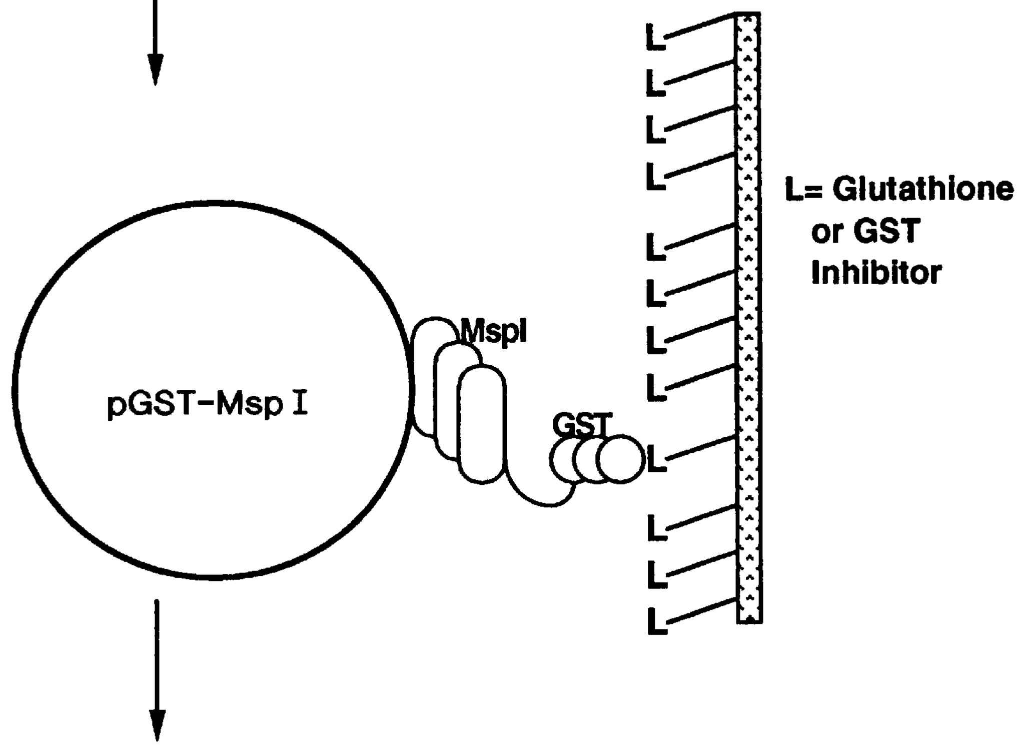
2] Purification of Plasmid-Polypeptide Determinant Conjugates,
3] PCR Amplification & Cloning of Selected GST Gene(s),
4] Sequencing and Expression of Mutated GST Gene(s)
FIG. 21

[GST-Msp I Gene Fusion Construct]

[GST-Msp I Gene Fusion Construct]

SEQUENCE LISTING ( 1 ) GENERAL INFORMATION:

( i i i ) NUMBER OF SEQUENCES: 71

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

TGACGGCGCA TGCAACCTGA 20

( 2 ) INFORMATION FOR SEQ ID NO:2:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

GTAAAACGAC GGCCAGT 17

( 2 ) INFORMATION FOR SEQ ID NO:3:

( i ) SEQUENCE CHARACTERISTICS:
( A ) LENGTH: 12 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

ATGAAACCTG AA 12

( 2 ) INFORMATION FOR SEQ ID NO:4:

( i ) SEQUENCE CHARACTERISTICS:
( A ) LENGTH: 12 base pairs
( B ) TYPE: nucleic acid
( C ) STRANDEDNESS: double ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

ATGCAACCTG AA 12

( 2 ) INFORMATION FOR SEQ ID NO:5:

( i ) SEQUENCE CHARACTERISTICS:
( A ) LENGTH: 5 amino acids
( B ) TYPE: amino acid
( D ) TOPOLOGY: linear ( i i ) MOLECULE TYPE: peptide ( v ) FRAGMENT TYPE: internal ( x i ) SEQUENCE DESCRIPTION: SEQ ID NO:5:

Gly Ile Asp Pro Pro
1 5

( 2 ) INFORMATION FOR SEQ ID NO:6:

( i ) SEQUENCE CHARACTERISTICS:
( A ) LENGTH: 43 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:6:

TCGTGGGATC CCCGGGAATT CAATGGAAAA AAAACTGATA AGC 43

( 2 ) INFORMATION FOR SEQ ID NO:7:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:7:

TATAAGAATT CCTAGAGTGG AAGGTGCATG AG 32

( 2 ) INFORMATION FOR SEQ ID NO:8:

( i ) SEQUENCE CHARACTERISTICS:
( A ) LENGTH: 44 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:8:

T C G T G G G A T C   C C C G G G A A T T   C A A T G G T G G A   A A A T G G G C T A   A A G C   4 4

( 2 ) INFORMATION FOR SEQ ID NO:9:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:9:

T A T A A G A A T T   C A T G C C A A A T   T T G G G T G G   2 8

( 2 ) INFORMATION FOR SEQ ID NO:10:

( i ) SEQUENCE CHARACTERISTICS:
( A ) LENGTH: 43 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:10:

T C G T G G G A T C   C C C G G G A A T T   C A A T G T C T G A   A T T T G A A T T A   C T G   4 3

( 2 ) INFORMATION FOR SEQ ID NO:11:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:11:

T A T A A G A A T T   C T A C C G G G A G   G A G C G A T C   2 8

( 2 ) INFORMATION FOR SEQ ID NO:12:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:12:

TCGTGGGATC CCCGGGAATT CAATGATAAA TATAGATAGG 40

(2) INFORMATION FOR SEQ ID NO:13:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:13:

TATAAGCATG CCATTGCATT AATTTTG 27

(2) INFORMATION FOR SEQ ID NO:14:

(i) SEQUENCE CHARACTERISTICS:
(A) LENGTH: 44 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:14:

TCGTGGGATC CCCGGGAATT CAATGAAAAT TAATGCAATG TCGC 44

(2) INFORMATION FOR SEQ ID NO:15:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:15:

TATAAGAATT CTATCAAATT TGATCATC 28

(2) INFORMATION FOR SEQ ID NO:16:

(i) SEQUENCE CHARACTERISTICS:
(A) LENGTH: 47 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:16:

TCGTGGGATC CCCGGGAATT CAATGATTGA AATAAAAGAT AAACAGC 47

(2) INFORMATION FOR SEQ ID NO:17:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:17:

TATAAGAATT CATGCCCCTT TCAATTTAA 29

( 2 ) INFORMATION FOR SEQ ID NO:18:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:18:

TCGTGGGATC CCCGGGAATT CAATGAAAGA TGTGTTAGAT G 41

( 2 ) INFORMATION FOR SEQ ID NO:19:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:19:

TATAAGAATT CAAGGCTCAC TCCACTCTCC TC 32

( 2 ) INFORMATION FOR SEQ ID NO:20:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:20:

TCGTGGGATC CCCGGGAATT CAATGCAAAA CTCATCACCT ACCAC 45

( 2 ) INFORMATION FOR SEQ ID NO:21:

( i ) SEQUENCE CHARACTERISTICS:
( A ) LENGTH: 32 base pairs
( B ) TYPE: nucleic acid ( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:21:

TATAAGAATT CCAGATGCCT GTAGGAAGGG TG 32

( 2 ) INFORMATION FOR SEQ ID NO:22:

( i ) SEQUENCE CHARACTERISTICS:
( A ) LENGTH: 44 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:22:

TCGTGGGATC CCCGGGAATT CAATGAATTA TATCGGCTCC AAAC 44

( 2 ) INFORMATION FOR SEQ ID NO:23:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:23:

TATAAGAATT CCCAAGTATT CGTACAG 27

( 2 ) INFORMATION FOR SEQ ID NO:24:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:24:

TCGTGGGATC CCCGGGAATT CAATGCTAAG AGTATTTGAA GC 42

( 2 ) INFORMATION FOR SEQ ID NO:25:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:25:

TATAAGAATT CTTCCTTTTA CATTAC 26

( 2 ) INFORMATION FOR SEQ ID NO:26:

( i ) SEQUENCE CHARACTERISTICS:
( A ) LENGTH: 47 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:26:

TCGTGGGATC CCCGGGAATT CAATGATAAT GAATGACATC ATTACCG 47

( 2 ) INFORMATION FOR SEQ ID NO:27:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:27:

TATAAGCATG CAATGGAAGG GGGATTCCC 29

( 2 ) INFORMATION FOR SEQ ID NO:28:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:28:

TCGTGGGATC CCCGGGAATT CAATGAGCAA AGTAGAAAAT 40

( 2 ) INFORMATION FOR SEQ ID NO:29:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:29:

TATAAGCATG CTATGTTTTA TTGACATGT 29

( 2 ) INFORMATION FOR SEQ ID NO:30:

( i ) SEQUENCE CHARACTERISTICS:
( A ) LENGTH: 52 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:30:

TCGTGGGATC CCCGGGAATT CAATGATAAT GACTGATAAT ATCGCAGCAA CA 52

( 2 ) INFORMATION FOR SEQ ID NO:31:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:31:

TATAAGAATT CGCGGTGTTC GCGGCAGAAT C 31

( 2 ) INFORMATION FOR SEQ ID NO:32:

( i ) SEQUENCE CHARACTERISTICS:
( A ) LENGTH: 78 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:32:

TCGTGGGATC CCCGGGAATT CAATGCAGAG TCTCGTGGGA TCCCCGGGAA TTCAATGCAG 60

AGTCTCGAGG TAGTGGAG 78

( 2 ) INFORMATION FOR SEQ ID NO:33:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:33:

TATAAGAATT CGCCTATGTG GACATCCAG 29

(2) INFORMATION FOR SEQ ID NO:34:

(i) SEQUENCE CHARACTERISTICS:
(A) LENGTH: 30 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:34:

CACAGGAAAC AGTATTCATG TCCCCTATAC 30

(2) INFORMATION FOR SEQ ID NO:35:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:35:

CACAGGAAAC AGCATGCATG TCCCCTATAC 30

(2) INFORMATION FOR SEQ ID NO:36:

(i) SEQUENCE CHARACTERISTICS:
(A) LENGTH: 32 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:36:

GGTCGTGGGA TCGATCCCCC CATGCAACCT GA 32

(2) INFORMATION FOR SEQ ID NO:37:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:37:

GGTCGTGGGA TCGATGCATG CATGCAACCT GA 32

( 2 ) INFORMATION FOR SEQ ID NO:38:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:38:

CACAGGAAAC AGCATGCATG CAACCTG 27

( 2 ) INFORMATION FOR SEQ ID NO:39:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:39:

TGAATTCCCG GGGATCCCAC GACCTTCGAT AACGAGTTCT AATTCAAACA AAAG 54

( 2 ) INFORMATION FOR SEQ ID NO:40:

( i ) SEQUENCE CHARACTERISTICS:
( A ) LENGTH: 8 amino acids
( B ) TYPE: amino acid
( D ) TOPOLOGY: linear ( i i ) MOLECULE TYPE: peptide ( v ) FRAGMENT TYPE: C-terminal ( x i ) SEQUENCE DESCRIPTION: SEQ ID NO:40:

Glu Asn Phe Glu Leu Glu Leu Val
1 5

( 2 ) INFORMATION FOR SEQ ID NO:41:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:41:

CACAGGAAAC AGGATCCCCA TGTCCCCTAT ACTAG 35

( 2 ) INFORMATION FOR SEQ ID NO:42:

( i ) SEQUENCE CHARACTERISTICS:
( A ) LENGTH: 40 base pairs
( B ) TYPE: nucleic acid
( C ) STRANDEDNESS: single ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:42:

TCACGAGGAT CCTCATCAAT CCGATTTTGG AGGATGGACG 40

( 2 ) INFORMATION FOR SEQ ID NO:43:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:43:

AATTCCAGGA TCCAGGACCA TGGTCCTGGA TGCAGG 36

( 2 ) INFORMATION FOR SEQ ID NO:44:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:44:

CCTGCGATCT GCGACTGCGT GACGCATGAC GCGCATG 37

( 2 ) INFORMATION FOR SEQ ID NO:45:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:45:

CGCGTCATGC GTCACGCAGT CGCAGATCGC AGGCATG 37

( 2 ) INFORMATION FOR SEQ ID NO:46:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:46:

AATTCAGCGC TGCGCAGCGC TGCGCAGCGC TGCGCG 36

( 2 ) INFORMATION FOR SEQ ID NO:47:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:47:

AATTCGCGCA GCGCTGCGCA GCGCTGCGCA GCGCTG 36

( 2 ) INFORMATION FOR SEQ ID NO:48:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:48:

AATTCATCCG GACCGGTCCG GATCCGGATG 30

( 2 ) INFORMATION FOR SEQ ID NO:49:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:49:

AATTCATGGC CATGGCCAGG CCTGGCCATG GCCATG 36

( 2 ) INFORMATION FOR SEQ ID NO:50:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:50:

AATTCGCCGG CATGCCGGCT AGCCGGCATG CCGGCG 36

( 2 ) INFORMATION FOR SEQ ID NO:51:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:51:

GTTCTGGCAA ATATTCTGAA ATGAGCTG 28

( 2 ) INFORMATION FOR SEQ ID NO:52:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:52:

CACAGTCTAT GGCCATCATA CGTTATATAG 30

( 2 ) INFORMATION FOR SEQ ID NO:53:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:53:

GTCAGTCAGT CACGATGAAT TCCACTTCTT G 31

( 2 ) INFORMATION FOR SEQ ID NO:54:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:54:

CATGGGGGAT CCCACGACCT TCG 23

( 2 ) INFORMATION FOR SEQ ID NO:55:

( i ) SEQUENCE CHARACTERISTICS:
( A ) LENGTH: 2095 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
( A ) NAME/KEY: CDS
( B ) LOCATION: 9..1952

( x i ) SEQUENCE DESCRIPTION: SEQ ID NO:55:

CAGTATTC ATG TCC CCT ATA CTA GGT TAT TGG AAA ATT AAG GGC CTT GTG 50
Met Ser Pro Ile Leu Gly Tyr Trp Lys Ile Lys Gly Leu Val
1 5 10

CAA CCC ACT CGA CTT CTT TTG GAA TAT CTT GAA GAA AAA TAT GAA GAG 98
Gln Pro Thr Arg Leu Leu Leu Glu Tyr Leu Glu Glu Lys Tyr Glu Glu
15 20 25 30

CAT TTG TAT GAG CGC GAT GAA GGT GAT AAA TGG CGA AAC AAA AAG TTT 146
His Leu Tyr Glu Arg Asp Glu Gly Asp Lys Trp Arg Asn Lys Lys Phe
35 40 45

GAA TTG GGT TTG GAG TTT CCC AAT CTT CCT TAT TAT ATT GAT GGT GAT 194
Glu Leu Gly Leu Glu Phe Pro Asn Leu Pro Tyr Tyr Ile Asp Gly Asp
50 55 60

GTT AAA TTA ACA CAG TCT ATG GCC ATC ATA CGT TAT ATA GCT GAC AAG 242
Val Lys Leu Thr Gln Ser Met Ala Ile Ile Arg Tyr Ile Ala Asp Lys
65 70 75

CAC AAC ATG TTG GGT GGT TGT CCA AAA GAG CGT GCA GAG ATT TCA ATG 290
His Asn Met Leu Gly Gly Cys Pro Lys Glu Arg Ala Glu Ile Ser Met
80 85 90

CTT GAA GGA GCG GTT TTG GAT ATT AGA TAC GGT GTT TCG AGA ATT GCA 338
Leu Glu Gly Ala Val Leu Asp Ile Arg Tyr Gly Val Ser Arg Ile Ala
95 100 105 110

TAT AGT AAA GAC TTT GAA ACT CTC AAA GTT GAT TTT CTT AGC AAG CTA 386
Tyr Ser Lys Asp Phe Glu Thr Leu Lys Val Asp Phe Leu Ser Lys Leu
115 120 125

CCT GAA ATG CTG AAA ATG TTC GAA GAT CGT TTA TGT CAT AAA ACA TAT 434
Pro Glu Met Leu Lys Met Phe Glu Asp Arg Leu Cys His Lys Thr Tyr
130 135 140

TTA AAT GGT GAT CAT GTA ACC CAT CCT GAC TTC ATG TTG TAT GAC GCT 482
Leu Asn Gly Asp His Val Thr His Pro Asp Phe Met Leu Tyr Asp Ala
145 150 155

CTT GAT GTT GTT TTA TAC ATG GAC CCA ATG TGC CTG GAT GCG TTC CCA 530
Leu Asp Val Val Leu Tyr Met Asp Pro Met Cys Leu Asp Ala Phe Pro
160 165 170

AAA TTA GTT TGT TTT AAA AAA CGT ATT GAA GCT ATC CCA CAA ATT GAT 578
Lys Leu Val Cys Phe Lys Lys Arg Ile Glu Ala Ile Pro Gln Ile Asp
175 180 185 190

AAG TAC TTG AAA TCC AGC AAG TAT ATA GCA TGG CCT TTG CAG GGC TGG 626
Lys Tyr Leu Lys Ser Ser Lys Tyr Ile Ala Trp Pro Leu Gln Gly Trp
195 200 205

CAA GCC ACG TTT GGT GGT GGC GAC CAT CCT CCA AAA TCG GAT ATC GAA 674
Gln Ala Thr Phe Gly Gly Gly Asp His Pro Pro Lys Ser Asp Ile Glu
210 215 220

GGT CGT GGG ATC GAT CCC CCC ATG CAA CCT GAA ATA TTG AAA TTG ATT 722
Gly Arg Gly Ile Asp Pro Pro Met Gln Pro Glu Ile Leu Lys Leu Ile
225 230 235

-continued

```
CGT AGT AAA TTG GAT CTA ACT CAA AAG CAA GCA TCT GAA ATT ATT GAG     770
Arg Ser Lys Leu Asp Leu Thr Gln Lys Gln Ala Ser Glu Ile Ile Glu
    240                     245                 250

GTT AGT GAT AAA ACA TGG CAA CAG TGG GAA TCA GGT AAA ACA GAA ATG     818
Val Ser Asp Lys Thr Trp Gln Gln Trp Glu Ser Gly Lys Thr Glu Met
255                 260                 265                 270

CAT CCT GCT TAT TAC TCT TTT CTC CAA GAA AAA CTT AAA GAT AAG ATT     866
His Pro Ala Tyr Tyr Ser Phe Leu Gln Glu Lys Leu Lys Asp Lys Ile
                275                 280                 285

AAC TTT GAG GAA CTG AGC GCT CAA AAA ACA CTC CAA AAG AAG ATA TTC     914
Asn Phe Glu Glu Leu Ser Ala Gln Lys Thr Leu Gln Lys Lys Ile Phe
            290                 295                 300

GAT AAA TAC AAT CAG AAT CAA ATT ACT AAA AAT GCG GAA GAA TTA GCT     962
Asp Lys Tyr Asn Gln Asn Gln Ile Thr Lys Asn Ala Glu Glu Leu Ala
        305                 310                 315

GAA ATT ACT CAT ATT GAA GAA AGA AAA GAT GCT TAT AGC AGT GAT TTC    1010
Glu Ile Thr His Ile Glu Glu Arg Lys Asp Ala Tyr Ser Ser Asp Phe
    320                     325                 330

AAA TTT ATT GAT TTA TTT TCT GGT ATC GGT GGA ATA AGG CAA TCA TTC    1058
Lys Phe Ile Asp Leu Phe Ser Gly Ile Gly Gly Ile Arg Gln Ser Phe
335                 340                 345                 350

GAA GTG AAT GGC GGA AAA TGC GTC TTT TCG TCT GAA ATA GAT CCC TTT    1106
Glu Val Asn Gly Gly Lys Cys Val Phe Ser Ser Glu Ile Asp Pro Phe
                355                 360                 365

GCA AAA TTT ACA TAT TAT ACA AAT TTT GGT GTA GTC CCT TTT GGA GAT    1154
Ala Lys Phe Thr Tyr Tyr Thr Asn Phe Gly Val Val Pro Phe Gly Asp
            370                 375                 380

ATT ACA AAA GTT GAG GCT ACA ACT ATT CCA CAG CAT GAC ATT TTA TGT    1202
Ile Thr Lys Val Glu Ala Thr Thr Ile Pro Gln His Asp Ile Leu Cys
        385                 390                 395

GCA GGA TTT CCG TGT CAG CCA TTT AGC CAT ATT GGT AAA AGA GAA GGC    1250
Ala Gly Phe Pro Cys Gln Pro Phe Ser His Ile Gly Lys Arg Glu Gly
    400                     405                 410

TTT GAA CAT CCA ACT CAA GGA ACA ATG TTC CAT GAA ATT GTT CGT ATC    1298
Phe Glu His Pro Thr Gln Gly Thr Met Phe His Glu Ile Val Arg Ile
415                 420                 425                 430

ATT GAA ACA AAA AAA ACC CCA GTT TTA TTT CTA GAA AAT GTT CCT GGT    1346
Ile Glu Thr Lys Lys Thr Pro Val Leu Phe Leu Glu Asn Val Pro Gly
                435                 440                 445

CTC ATT AAT CAT GAT GAC GGA AAT ACA TTA AAA GTC ATC ATT GAA ACA    1394
Leu Ile Asn His Asp Asp Gly Asn Thr Leu Lys Val Ile Ile Glu Thr
            450                 455                 460

CTA GAA GAT ATG GGC TAC AAA GTT CAT CAT ACG GTA CTA GAC GCT AGT    1442
Leu Glu Asp Met Gly Tyr Lys Val His His Thr Val Leu Asp Ala Ser
        465                 470                 475

CAT TTT GGT ATC CCA CAA AAA CGT AAG CGT TTT TAC TTA GTA GCT TTC    1490
His Phe Gly Ile Pro Gln Lys Arg Lys Arg Phe Tyr Leu Val Ala Phe
    480                     485                 490

CTA AAT CAA AAT ATT CAC TTT GAG TTT CCT AAA CCT CCA ATG ATT TCT    1538
Leu Asn Gln Asn Ile His Phe Glu Phe Pro Lys Pro Pro Met Ile Ser
495                 500                 505                 510

AAA GAT ATC GGT GAA GTT TTA GAA AGC GAT GTA ACT GGA TAT AGC ATT    1586
Lys Asp Ile Gly Glu Val Leu Glu Ser Asp Val Thr Gly Tyr Ser Ile
                515                 520                 525

TCA GAG CAT TTA CAA AAA AGT TAT CTC TTT AAA AAA GAT GAT GGT AAA    1634
Ser Glu His Leu Gln Lys Ser Tyr Leu Phe Lys Lys Asp Asp Gly Lys
            530                 535                 540

CCT TCT TTA ATT GAC AAA AAT ACG ACT GGG GCA GTT AAA ACA TTA GTT    1682
Pro Ser Leu Ile Asp Lys Asn Thr Thr Gly Ala Val Lys Thr Leu Val
        545                 550                 555
```

-continued

```
TCT ACC TAT CAC AAA ATT CAA CGA TTA ACA GGT ACT TTT GTT AAG GAT      1730
Ser Thr Tyr His Lys Ile Gln Arg Leu Thr Gly Thr Phe Val Lys Asp
    560                 565                 570

GGA GAA ACA GGT ATC CGT CTT TTA ACA ACG AAT GAA TGC AAA GCT ATT      1778
Gly Glu Thr Gly Ile Arg Leu Leu Thr Thr Asn Glu Cys Lys Ala Ile
575                 580                 585                 590

ATG GGT TTT CCA AAA GAT TTT GTT ATT CCT GTA TCA AGA ACT CAG ATG      1826
Met Gly Phe Pro Lys Asp Phe Val Ile Pro Val Ser Arg Thr Gln Met
                595                 600                 605

TAC CGT CAA ATG GGT AAC TCT GTC GTA GTT CCG GTG GTT ACA AAA ATT      1874
Tyr Arg Gln Met Gly Asn Ser Val Val Val Pro Val Val Thr Lys Ile
            610                 615                 620

GCA GAA CAG ATT AGT TTG GCA CTA AAA ACT GTT AAC CAA CAA TCC CCG      1922
Ala Glu Gln Ile Ser Leu Ala Leu Lys Thr Val Asn Gln Gln Ser Pro
        625                 630                 635

CAA GAA AAC TTT GAA TTA GAA CTC GTT TAAAAAAAAT ATAGCCCCTA            1969
Gln Glu Asn Phe Glu Leu Glu Leu Val
    640                 645

ATTGAGGGGC TATTTAACAT AAAATCTCAT ATACGAAATT CAGTTAGTAG TGAACTTTTC    2029

CGACTATGAT GTTTTCATTG AAAAACATCT ATAAAATCAA TTAAATATAT TCAAGAAGTG    2089

GAATTC                                                               2095
```

( 2 ) INFORMATION FOR SEQ ID NO:56:

( i ) SEQUENCE CHARACTERISTICS:
( A ) LENGTH: 647 amino acids
( B ) TYPE: amino acid
( D ) TOPOLOGY: linear ( i i ) MOLECULE TYPE: protein ( x i ) SEQUENCE DESCRIPTION: SEQ ID NO:56:

```
Met Ser Pro Ile Leu Gly Tyr Trp Lys Ile Lys Gly Leu Val Gln Pro
  1               5                  10                  15

Thr Arg Leu Leu Leu Glu Tyr Leu Glu Glu Lys Tyr Glu Glu His Leu
             20                  25                  30

Tyr Glu Arg Asp Glu Gly Asp Lys Trp Arg Asn Lys Lys Phe Glu Leu
         35                  40                  45

Gly Leu Glu Phe Pro Asn Leu Pro Tyr Tyr Ile Asp Gly Asp Val Lys
     50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
```

-continued

```
        195                     200                     205

Thr Phe Gly Gly Gly Asp His Pro Pro Lys Ser Asp Ile Glu Gly Arg
    210                 215                 220

Gly Ile Asp Pro Pro Met Gln Pro Glu Ile Leu Lys Leu Ile Arg Ser
225                 230                 235                 240

Lys Leu Asp Leu Thr Gln Lys Gln Ala Ser Glu Ile Ile Glu Val Ser
                245                 250                 255

Asp Lys Thr Trp Gln Gln Trp Glu Ser Gly Lys Thr Glu Met His Pro
            260                 265                 270

Ala Tyr Tyr Ser Phe Leu Gln Glu Lys Leu Lys Asp Lys Ile Asn Phe
        275                 280                 285

Glu Glu Leu Ser Ala Gln Lys Thr Leu Gln Lys Lys Ile Phe Asp Lys
    290                 295                 300

Tyr Asn Gln Asn Gln Ile Thr Lys Asn Ala Glu Glu Leu Ala Glu Ile
305                 310                 315                 320

Thr His Ile Glu Glu Arg Lys Asp Ala Tyr Ser Ser Asp Phe Lys Phe
                325                 330                 335

Ile Asp Leu Phe Ser Gly Ile Gly Gly Ile Arg Gln Ser Phe Glu Val
            340                 345                 350

Asn Gly Gly Lys Cys Val Phe Ser Ser Glu Ile Asp Pro Phe Ala Lys
        355                 360                 365

Phe Thr Tyr Tyr Thr Asn Phe Gly Val Val Pro Phe Gly Asp Ile Thr
    370                 375                 380

Lys Val Glu Ala Thr Thr Ile Pro Gln His Asp Ile Leu Cys Ala Gly
385                 390                 395                 400

Phe Pro Cys Gln Pro Phe Ser His Ile Gly Lys Arg Glu Gly Phe Glu
                405                 410                 415

His Pro Thr Gln Gly Thr Met Phe His Glu Ile Val Arg Ile Ile Glu
            420                 425                 430

Thr Lys Lys Thr Pro Val Leu Phe Leu Glu Asn Val Pro Gly Leu Ile
        435                 440                 445

Asn His Asp Asp Gly Asn Thr Leu Lys Val Ile Ile Glu Thr Leu Glu
    450                 455                 460

Asp Met Gly Tyr Lys Val His His Thr Val Leu Asp Ala Ser His Phe
465                 470                 475                 480

Gly Ile Pro Gln Lys Arg Lys Arg Phe Tyr Leu Val Ala Phe Leu Asn
                485                 490                 495

Gln Asn Ile His Phe Glu Phe Pro Lys Pro Pro Met Ile Ser Lys Asp
            500                 505                 510

Ile Gly Glu Val Leu Glu Ser Asp Val Thr Gly Tyr Ser Ile Ser Glu
        515                 520                 525

His Leu Gln Lys Ser Tyr Leu Phe Lys Lys Asp Asp Gly Lys Pro Ser
    530                 535                 540

Leu Ile Asp Lys Asn Thr Thr Gly Ala Val Lys Thr Leu Val Ser Thr
545                 550                 555                 560

Tyr His Lys Ile Gln Arg Leu Thr Gly Thr Phe Val Lys Asp Gly Glu
                565                 570                 575

Thr Gly Ile Arg Leu Leu Thr Thr Asn Glu Cys Lys Ala Ile Met Gly
            580                 585                 590

Phe Pro Lys Asp Phe Val Ile Pro Val Ser Arg Thr Gln Met Tyr Arg
        595                 600                 605

Gln Met Gly Asn Ser Val Val Val Pro Val Val Thr Lys Ile Ala Glu
    610                 615                 620
```

-continued

```
Gln Ile Ser Leu Ala Leu Lys Thr Val Asn Gln Gln Ser Pro Gln Glu
625                 630                 635                 640

Asn Phe Glu Leu Glu Leu Val
                645
```

( 2 ) INFORMATION FOR SEQ ID NO:57:

( i ) SEQUENCE CHARACTERISTICS:
( A ) LENGTH: 1400 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
( A ) NAME/KEY: CDS
( B ) LOCATION: 1..1257

( x i ) SEQUENCE DESCRIPTION: SEQ ID NO:57:

```
ATG AAA CCT GAA ATA TTG AAA TTG ATT CGT AGT AAA TTG GAT CTA ACT       48
Met Lys Pro Glu Ile Leu Lys Leu Ile Arg Ser Lys Leu Asp Leu Thr
  1               5                  10                  15

CAA AAG CAA GCA TCT GAA ATT ATT GAA GTT AGT GAT AAA ACA TGG CAA       96
Gln Lys Gln Ala Ser Glu Ile Ile Glu Val Ser Asp Lys Thr Trp Gln
             20                  25                  30

CAG TGG GAA TCA GGT AAA ACA GAA ATG CAT CCT GCT TAT TAC TCT TTT      144
Gln Trp Glu Ser Gly Lys Thr Glu Met His Pro Ala Tyr Tyr Ser Phe
         35                  40                  45

CTC CAA GAA AAA CTT AAA GAT AAG ATT AAC TTT GAG GAA CTG AGC GCT      192
Leu Gln Glu Lys Leu Lys Asp Lys Ile Asn Phe Glu Glu Leu Ser Ala
     50                  55                  60

CAA AAA ACA CTC CAA AAG AAG ATA TTC GAT AAA TAC AAT CAG AAT CAA      240
Gln Lys Thr Leu Gln Lys Lys Ile Phe Asp Lys Tyr Asn Gln Asn Gln
 65                  70                  75                  80

ATT ACT AAA AAT GCG GAA GAA TTA GCT GAA ATT ACT CAT ATT GAA GAA      288
Ile Thr Lys Asn Ala Glu Glu Leu Ala Glu Ile Thr His Ile Glu Glu
                 85                  90                  95

AGA AAA GAT GCT TAT AGC AGT GAT TTC AAA TTT ATT GAT TTA TTT TCT      336
Arg Lys Asp Ala Tyr Ser Ser Asp Phe Lys Phe Ile Asp Leu Phe Ser
            100                 105                 110

GGT ATC GGT GGA ATA AGG CAA TCA TTC GAA GTG AAT GGC GGA AAA TGC      384
Gly Ile Gly Gly Ile Arg Gln Ser Phe Glu Val Asn Gly Gly Lys Cys
        115                 120                 125

GTC TTT TCG TCT GAA ATA GAT CCC TTT GCA AAA TTT ACA TAT TAT ACA      432
Val Phe Ser Ser Glu Ile Asp Pro Phe Ala Lys Phe Thr Tyr Tyr Thr
    130                 135                 140

AAT TTT GGT GTA GTC CCT TTT GGA GAT ATT ACA AAA GTT GAG GCT ACA      480
Asn Phe Gly Val Val Pro Phe Gly Asp Ile Thr Lys Val Glu Ala Thr
145                 150                 155                 160

ACT ATT CCA CAG CAT GAC ATT TTA TGT GCA GGA TTT CCG TGT CAG CCA      528
Thr Ile Pro Gln His Asp Ile Leu Cys Ala Gly Phe Pro Cys Gln Pro
                165                 170                 175

TTT AGC CAT ATT GGT AAA AGA GAA GGC TTT GAA CAT CCA ACT CAA GGA      576
Phe Ser His Ile Gly Lys Arg Glu Gly Phe Glu His Pro Thr Gln Gly
            180                 185                 190

ACA ATG TTC CAT GAA ATT GTT CGT ATC ATT GAA ACA AAA AAA ACC CCA      624
Thr Met Phe His Glu Ile Val Arg Ile Ile Glu Thr Lys Lys Thr Pro
        195                 200                 205

GTT TTA TTT CTA GAA AAT GTT CCT GGT CTC ATT AAT CAT GAT GAC GGA      672
```

```
Val Leu Phe Leu Glu Asn Val Pro Gly Leu Ile Asn His Asp Asp Gly
    210                 215                 220

AAT ACA TTA AAA GTC ATC ATT GAA ACA CTA GAA GAT ATG GGC TAC AAA       720
Asn Thr Leu Lys Val Ile Ile Glu Thr Leu Glu Asp Met Gly Tyr Lys
225                 230                 235                 240

GTT CAT CAT ACG GTA CTA GAC GCT AGT CAT TTT GGT ATC CCA CAA AAA       768
Val His His Thr Val Leu Asp Ala Ser His Phe Gly Ile Pro Gln Lys
                245                 250                 255

CGT AAG CGT TTT TAC TTA GTA GCT TTC CTA AAT CAA AAT ATT CAC TTT       816
Arg Lys Arg Phe Tyr Leu Val Ala Phe Leu Asn Gln Asn Ile His Phe
            260                 265                 270

GAG TTT CCT AAA CCT CCA ATG ATT TCT AAA GAT ATC GGT GAA GTT TTA       864
Glu Phe Pro Lys Pro Pro Met Ile Ser Lys Asp Ile Gly Glu Val Leu
        275                 280                 285

GAA AGC GAT GTA ACT GGA TAT AGC ATT TCA GAG CAT TTA CAA AAA AGT       912
Glu Ser Asp Val Thr Gly Tyr Ser Ile Ser Glu His Leu Gln Lys Ser
    290                 295                 300

TAT CTC TTT AAA AAA GAT GAT GGT AAA CCT TCT TTA ATT GAC AAA AAT       960
Tyr Leu Phe Lys Lys Asp Asp Gly Lys Pro Ser Leu Ile Asp Lys Asn
305                 310                 315                 320

ACG ACT GGG GCA GTT AAA ACA TTA GTT TCT ACC TAT CAC AAA ATT CAA      1008
Thr Thr Gly Ala Val Lys Thr Leu Val Ser Thr Tyr His Lys Ile Gln
                325                 330                 335

CGA TTA ACA GGT ACT TTT GTT AAG GAT GGA GAA ACA GGT ATC CGT CTT      1056
Arg Leu Thr Gly Thr Phe Val Lys Asp Gly Glu Thr Gly Ile Arg Leu
            340                 345                 350

TTA ACA ACG AAT GAA TGC AAA GCT ATT ATG GGT TTT CCA AAA GAT TTT      1104
Leu Thr Thr Asn Glu Cys Lys Ala Ile Met Gly Phe Pro Lys Asp Phe
        355                 360                 365

GTT ATT CCT GTA TCA AGA ACT CAG ATG TAC CGT CAA ATG GGT AAC TCT      1152
Val Ile Pro Val Ser Arg Thr Gln Met Tyr Arg Gln Met Gly Asn Ser
    370                 375                 380

GTC GTA GTT CCG GTG GTT ACA AAA ATT GCA GAA CAG ATT AGT TTG GCA      1200
Val Val Val Pro Val Val Thr Lys Ile Ala Glu Gln Ile Ser Leu Ala
385                 390                 395                 400

CTA AAA ACT GTT AAC CAA CAA TCC CCG CAA GAA AAC TTT GAA TTA GAA      1248
Leu Lys Thr Val Asn Gln Gln Ser Pro Gln Glu Asn Phe Glu Leu Glu
                405                 410                 415

CTC GTT TAAAAAAAAT ATAGCCCCTA ATTGAGGGGC TATTTAACAT AAAATCTCAT       1304
Leu Val

ATACGAAATT CAGTTAGTAG TGAACTTTTC CGACTATGAT GTTTTCATTG AAAAACATCT    1364

ATAAAATCAA TTAAATATAT TCAAGAAGTG GAATTC                              1400
```

( 2 ) INFORMATION FOR SEQ ID NO:58:

( i ) SEQUENCE CHARACTERISTICS:
( A ) LENGTH: 418 amino acids
( B ) TYPE: amino acid
( D ) TOPOLOGY: linear ( i i ) MOLECULE TYPE: protein ( x i ) SEQUENCE DESCRIPTION: SEQ ID NO:58:

```
Met Lys Pro Glu Ile Leu Lys Leu Ile Arg Ser Lys Leu Asp Leu Thr
  1               5                  10                  15

Gln Lys Gln Ala Ser Glu Ile Ile Glu Val Ser Asp Lys Thr Trp Gln
             20                  25                  30

Gln Trp Glu Ser Gly Lys Thr Glu Met His Pro Ala Tyr Tyr Ser Phe
         35                  40                  45

Leu Gln Glu Lys Leu Lys Asp Lys Ile Asn Phe Glu Glu Leu Ser Ala
```

50 55 60

Gln Lys Thr Leu Gln Lys Lys Ile Phe Asp Lys Tyr Asn Gln Asn Gln
65 70 75 80

Ile Thr Lys Asn Ala Glu Glu Leu Ala Glu Ile Thr His Ile Glu Glu
85 90 95

Arg Lys Asp Ala Tyr Ser Ser Asp Phe Lys Phe Ile Asp Leu Phe Ser
100 105 110

Gly Ile Gly Gly Ile Arg Gln Ser Phe Glu Val Asn Gly Gly Lys Cys
115 120 125

Val Phe Ser Ser Glu Ile Asp Pro Phe Ala Lys Phe Thr Tyr Tyr Thr
130 135 140

Asn Phe Gly Val Val Pro Phe Gly Asp Ile Thr Lys Val Glu Ala Thr
145 150 155 160

Thr Ile Pro Gln His Asp Ile Leu Cys Ala Gly Phe Pro Cys Gln Pro
165 170 175

Phe Ser His Ile Gly Lys Arg Glu Gly Phe Glu His Pro Thr Gln Gly
180 185 190

Thr Met Phe His Glu Ile Val Arg Ile Ile Glu Thr Lys Lys Thr Pro
195 200 205

Val Leu Phe Leu Glu Asn Val Pro Gly Leu Ile Asn His Asp Asp Gly
210 215 220

Asn Thr Leu Lys Val Ile Ile Glu Thr Leu Glu Asp Met Gly Tyr Lys
225 230 235 240

Val His His Thr Val Leu Asp Ala Ser His Phe Gly Ile Pro Gln Lys
245 250 255

Arg Lys Arg Phe Tyr Leu Val Ala Phe Leu Asn Gln Asn Ile His Phe
260 265 270

Glu Phe Pro Lys Pro Pro Met Ile Ser Lys Asp Ile Gly Glu Val Leu
275 280 285

Glu Ser Asp Val Thr Gly Tyr Ser Ile Ser Glu His Leu Gln Lys Ser
290 295 300

Tyr Leu Phe Lys Lys Asp Asp Gly Lys Pro Ser Leu Ile Asp Lys Asn
305 310 315 320

Thr Thr Gly Ala Val Lys Thr Leu Val Ser Thr Tyr His Lys Ile Gln
325 330 335

Arg Leu Thr Gly Thr Phe Val Lys Asp Gly Glu Thr Gly Ile Arg Leu
340 345 350

Leu Thr Thr Asn Glu Cys Lys Ala Ile Met Gly Phe Pro Lys Asp Phe
355 360 365

Val Ile Pro Val Ser Arg Thr Gln Met Tyr Arg Gln Met Gly Asn Ser
370 375 380

Val Val Val Pro Val Val Thr Lys Ile Ala Glu Gln Ile Ser Leu Ala
385 390 395 400

Leu Lys Thr Val Asn Gln Gln Ser Pro Gln Glu Asn Phe Glu Leu Glu
405 410 415

Leu Val ( 2 ) INFORMATION FOR SEQ ID NO:59:

( i ) SEQUENCE CHARACTERISTICS:
( A ) LENGTH: 1400 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
( A ) NAME/KEY: CDS
( B ) LOCATION: 1..1257

( x i ) SEQUENCE DESCRIPTION: SEQ ID NO:59:

```
ATG CAA CCT GAA ATA TTG AAA TTG ATT CGT AGT AAA TTG GAT CTA ACT       48
Met Gln Pro Glu Ile Leu Lys Leu Ile Arg Ser Lys Leu Asp Leu Thr
  1               5                  10                  15

CAA AAG CAA GCA TCT GAA ATT ATT GAG GTT AGT GAT AAA ACA TGG CAA       96
Gln Lys Gln Ala Ser Glu Ile Ile Glu Val Ser Asp Lys Thr Trp Gln
             20                  25                  30

CAG TGG GAA TCA GGT AAA ACA GAA ATG CAT CCT GCT TAT TAC TCT TTT      144
Gln Trp Glu Ser Gly Lys Thr Glu Met His Pro Ala Tyr Tyr Ser Phe
         35                  40                  45

CTC CAA GAA AAA CTT AAA GAT AAG ATT AAC TTT GAG GAA CTG AGC GCT      192
Leu Gln Glu Lys Leu Lys Asp Lys Ile Asn Phe Glu Glu Leu Ser Ala
     50                  55                  60

CAA AAA ACA CTC CAA AAG AAG ATA TTC GAT AAA TAC AAT CAG AAT CAA      240
Gln Lys Thr Leu Gln Lys Lys Ile Phe Asp Lys Tyr Asn Gln Asn Gln
 65                  70                  75                  80

ATT ACT AAA AAT GCG GAA GAA TTA GCT GAA ATT ACT CAT ATT GAA GAA      288
Ile Thr Lys Asn Ala Glu Glu Leu Ala Glu Ile Thr His Ile Glu Glu
                 85                  90                  95

AGA AAA GAT GCT TAT AGC AGT GAT TTC AAA TTT ATT GAT TTA TTT TCT      336
Arg Lys Asp Ala Tyr Ser Ser Asp Phe Lys Phe Ile Asp Leu Phe Ser
            100                 105                 110

GGT ATC GGT GGA ATA AGG CAA TCA TTC GAA GTG AAT GGC GGA AAA TGC      384
Gly Ile Gly Gly Ile Arg Gln Ser Phe Glu Val Asn Gly Gly Lys Cys
        115                 120                 125

GTC TTT TCG TCT GAA ATA GAT CCC TTT GCA AAA TTT ACA TAT TAT ACA      432
Val Phe Ser Ser Glu Ile Asp Pro Phe Ala Lys Phe Thr Tyr Tyr Thr
    130                 135                 140

AAT TTT GGT GTA GTC CCT TTT GGA GAT ATT ACA AAA GTT GAG GCT ACA      480
Asn Phe Gly Val Val Pro Phe Gly Asp Ile Thr Lys Val Glu Ala Thr
145                 150                 155                 160

ACT ATT CCA CAG CAT GAC ATT TTA TGT GCA GGA TTT CCG TGT CAG CCA      528
Thr Ile Pro Gln His Asp Ile Leu Cys Ala Gly Phe Pro Cys Gln Pro
                165                 170                 175

TTT AGC CAT ATT GGT AAA AGA GAA GGC TTT GAA CAT CCA ACT CAA GGA      576
Phe Ser His Ile Gly Lys Arg Glu Gly Phe Glu His Pro Thr Gln Gly
            180                 185                 190

ACA ATG TTC CAT GAA ATT GTT CGT ATC ATT GAA ACA AAA AAA ACC CCA      624
Thr Met Phe His Glu Ile Val Arg Ile Ile Glu Thr Lys Lys Thr Pro
        195                 200                 205

GTT TTA TTT CTA GAA AAT GTT CCT GGT CTC ATT AAT CAT GAT GAC GGA      672
Val Leu Phe Leu Glu Asn Val Pro Gly Leu Ile Asn His Asp Asp Gly
    210                 215                 220

AAT ACA TTA AAA GTC ATC ATT GAA ACA CTA GAA GAT ATG GGC TAC AAA      720
Asn Thr Leu Lys Val Ile Ile Glu Thr Leu Glu Asp Met Gly Tyr Lys
225                 230                 235                 240

GTT CAT CAT ACG GTA CTA GAC GCT AGT CAT TTT GGT ATC CCA CAA AAA      768
Val His His Thr Val Leu Asp Ala Ser His Phe Gly Ile Pro Gln Lys
                245                 250                 255

CGT AAG CGT TTT TAC TTA GTA GCT TTC CTA AAT CAA AAT ATT CAC TTT      816
Arg Lys Arg Phe Tyr Leu Val Ala Phe Leu Asn Gln Asn Ile His Phe
            260                 265                 270

GAG TTT CCT AAA CCT CCA ATG ATT TCT AAA GAT ATC GGT GAA GTT TTA      864
```

-continued

```
Glu Phe Pro Lys Pro Pro Met Ile Ser Lys Asp Ile Gly Glu Val Leu
        275                 280                 285

GAA AGC GAT GTA ACT GGA TAT AGC ATT TCA GAG CAT TTA CAA AAA AGT      912
Glu Ser Asp Val Thr Gly Tyr Ser Ile Ser Glu His Leu Gln Lys Ser
    290                 295                 300

TAT CTC TTT AAA AAA GAT GAT GGT AAA CCT TCT TTA ATT GAC AAA AAT      960
Tyr Leu Phe Lys Lys Asp Asp Gly Lys Pro Ser Leu Ile Asp Lys Asn
305                 310                 315                 320

ACG ACT GGG GCA GTT AAA ACA TTA GTT TCT ACC TAT CAC AAA ATT CAA     1008
Thr Thr Gly Ala Val Lys Thr Leu Val Ser Thr Tyr His Lys Ile Gln
                325                 330                 335

CGA TTA ACA GGT ACT TTT GTT AAG GAT GGA GAA ACA GGT ATC CGT CTT     1056
Arg Leu Thr Gly Thr Phe Val Lys Asp Gly Glu Thr Gly Ile Arg Leu
            340                 345                 350

TTA ACA ACG AAT GAA TGC AAA GCT ATT ATG GGT TTT CCA AAA GAT TTT     1104
Leu Thr Thr Asn Glu Cys Lys Ala Ile Met Gly Phe Pro Lys Asp Phe
        355                 360                 365

GTT ATT CCT GTA TCA AGA ACT CAG ATG TAC CGT CAA ATG GGT AAC TCT     1152
Val Ile Pro Val Ser Arg Thr Gln Met Tyr Arg Gln Met Gly Asn Ser
    370                 375                 380

GTC GTA GTT CCG GTG GTT ACA AAA ATT GCA GAA CAG ATT AGT TTG GCA     1200
Val Val Val Pro Val Val Thr Lys Ile Ala Glu Gln Ile Ser Leu Ala
385                 390                 395                 400

CTA AAA ACT GTT AAC CAA CAA TCC CCG CAA GAA AAC TTT GAA TTA GAA     1248
Leu Lys Thr Val Asn Gln Gln Ser Pro Gln Glu Asn Phe Glu Leu Glu
                405                 410                 415

CTC GTT TAAAAAAAAT ATAGCCCCTA ATTGAGGGGC TATTTAACAT AAAATCTCAT      1304
Leu Val

ATACGAAATT CAGTTAGTAG TGAACTTTTC CGACTATGAT GTTTTCATTG AAAAACATCT   1364

ATAAAATCAA TTAAATATAT TCAAGAAGTG GAATTC                             1400
```

( 2 ) INFORMATION FOR SEQ ID NO:60:

( i ) SEQUENCE CHARACTERISTICS:
( A ) LENGTH: 418 amino acids
( B ) TYPE: amino acid
( D ) TOPOLOGY: linear ( i i ) MOLECULE TYPE: protein ( x i ) SEQUENCE DESCRIPTION: SEQ ID NO:60:

```
Met Gln Pro Glu Ile Leu Lys Leu Ile Arg Ser Lys Leu Asp Leu Thr
  1               5                  10                  15

Gln Lys Gln Ala Ser Glu Ile Ile Glu Val Ser Asp Lys Thr Trp Gln
             20                  25                  30

Gln Trp Glu Ser Gly Lys Thr Glu Met His Pro Ala Tyr Tyr Ser Phe
         35                  40                  45

Leu Gln Glu Lys Leu Lys Asp Lys Ile Asn Phe Glu Glu Leu Ser Ala
     50                  55                  60

Gln Lys Thr Leu Gln Lys Lys Ile Phe Asp Lys Tyr Asn Gln Asn Gln
 65                  70                  75                  80

Ile Thr Lys Asn Ala Glu Glu Leu Ala Glu Ile Thr His Ile Glu Glu
                 85                  90                  95

Arg Lys Asp Ala Tyr Ser Ser Asp Phe Lys Phe Ile Asp Leu Phe Ser
            100                 105                 110

Gly Ile Gly Gly Ile Arg Gln Ser Phe Glu Val Asn Gly Gly Lys Cys
        115                 120                 125

Val Phe Ser Ser Glu Ile Asp Pro Phe Ala Lys Phe Thr Tyr Tyr Thr
    130                 135                 140
```

Asn Phe Gly Val Val Pro Phe Gly Asp Ile Thr Lys Val Glu Ala Thr
145 150 155 160

Thr Ile Pro Gln His Asp Ile Leu Cys Ala Gly Phe Pro Cys Gln Pro
165 170 175

Phe Ser His Ile Gly Lys Arg Glu Gly Phe Glu His Pro Thr Gln Gly
180 185 190

Thr Met Phe His Glu Ile Val Arg Ile Ile Glu Thr Lys Lys Thr Pro
195 200 205

Val Leu Phe Leu Glu Asn Val Pro Gly Leu Ile Asn His Asp Asp Gly
210 215 220

Asn Thr Leu Lys Val Ile Ile Glu Thr Leu Glu Asp Met Gly Tyr Lys
225 230 235 240

Val His His Thr Val Leu Asp Ala Ser His Phe Gly Ile Pro Gln Lys
245 250 255

Arg Lys Arg Phe Tyr Leu Val Ala Phe Leu Asn Gln Asn Ile His Phe
260 265 270

Glu Phe Pro Lys Pro Pro Met Ile Ser Lys Asp Ile Gly Glu Val Leu
275 280 285

Glu Ser Asp Val Thr Gly Tyr Ser Ile Ser Glu His Leu Gln Lys Ser
290 295 300

Tyr Leu Phe Lys Lys Asp Asp Gly Lys Pro Ser Leu Ile Asp Lys Asn
305 310 315 320

Thr Thr Gly Ala Val Lys Thr Leu Val Ser Thr Tyr His Lys Ile Gln
325 330 335

Arg Leu Thr Gly Thr Phe Val Lys Asp Gly Glu Thr Gly Ile Arg Leu
340 345 350

Leu Thr Thr Asn Glu Cys Lys Ala Ile Met Gly Phe Pro Lys Asp Phe
355 360 365

Val Ile Pro Val Ser Arg Thr Gln Met Tyr Arg Gln Met Gly Asn Ser
370 375 380

Val Val Val Pro Val Val Thr Lys Ile Ala Glu Gln Ile Ser Leu Ala
385 390 395 400

Leu Lys Thr Val Asn Gln Gln Ser Pro Gln Glu Asn Phe Glu Leu Glu
405 410 415

Leu Val ( 2 ) INFORMATION FOR SEQ ID NO:61:

( i ) SEQUENCE CHARACTERISTICS:
( A ) LENGTH: 42 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:61:

GAATTCCAGG ATCCAGGACC ATGGTCCTGG ATCCAGGAAT TC 42

( 2 ) INFORMATION FOR SEQ ID NO:62:

( i ) SEQUENCE CHARACTERISTICS:
( A ) LENGTH: 43 base pairs
( B ) TYPE: nucleic acid
( C ) STRANDEDNESS: double (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:62:

GCATGCCTGC GATCTGCGAC TGCGTGACGC ATGACGCGCA TGC 43

(2) INFORMATION FOR SEQ ID NO:63:

(i) SEQUENCE CHARACTERISTICS:
(A) LENGTH: 42 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:63:

GAATTCAGCG CTGCGCAGCG CTGCGCAGCG CTGCGCGAAT TC 42

(2) INFORMATION FOR SEQ ID NO:64:

(i) SEQUENCE CHARACTERISTICS:
(A) LENGTH: 42 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:64:

GAATTCATCC GGATCCGGAC CGGTCCGGAT CCGGATGAAT TC 42

(2) INFORMATION FOR SEQ ID NO:65:

(i) SEQUENCE CHARACTERISTICS:
(A) LENGTH: 42 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:65:

GAATTCATGG CCATGGCCAG GCCTGGCCAT GGCCATGAAT TC 42

(2) INFORMATION FOR SEQ ID NO:66:

(i) SEQUENCE CHARACTERISTICS:
(A) LENGTH: 42 base pairs
(B) TYPE: nucleic acid
(C) STRANDEDNESS: double
(D) TOPOLOGY: linear (ii) MOLECULE TYPE: DNA (genomic)

( i i i ) HYPOTHETICAL: NO ( i v ) ANTI-SENSE: NO ( x i ) SEQUENCE DESCRIPTION: SEQ ID NO:66:

GAATTCGCCG GCATGCCGGC TAGCCGGCAT GCCGGCGAAT TC 42

( 2 ) INFORMATION FOR SEQ ID NO:67:

( i ) SEQUENCE CHARACTERISTICS:
( A ) LENGTH: 42 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:67:

GAATTCCTGG ATCCAGGACC ATGGTCCTGG ATCCTGGAAT TC 42

( 2 ) INFORMATION FOR SEQ ID NO:68:

( i ) SEQUENCE CHARACTERISTICS:
( A ) LENGTH: 43 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:68:

GCATGCGCGT CATGCGTCAC GCAGTCGCAG ATCGCAGGCA TGC 43

( 2 ) INFORMATION FOR SEQ ID NO:69:

( i ) SEQUENCE CHARACTERISTICS:
( A ) LENGTH: 42 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:69:

GAATTCGCGC AGCGCTGCGC AGCGCTGCGC AGCGCTGAAT TC 42

( 2 ) INFORMATION FOR SEQ ID NO:70:

( i ) SEQUENCE CHARACTERISTICS:
( A ) LENGTH: 42 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO

-continued ( x i ) SEQUENCE DESCRIPTION: SEQ ID NO:70:

GAATTCATCC GGATCCGGAC CGGTCCGGAT CCGGATGAAT TC 42

( 2 ) INFORMATION FOR SEQ ID NO:71:

( i ) SEQUENCE CHARACTERISTICS:
( A ) LENGTH: 42 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:71:

GAATTCATGG CCATGGCCAG GCCTGGCCAT GGCCATGAAT TC 42

DNA-METHYLASE LINKING REACTION

BACKGROUND OF THE INVENTION

This invention is directed to methods of linking genetic information with proteins encoded by the genetic information, to plasmids that can be used in the process of covalently linking nucleic acid segments to protein encoded by the nucleic acid, and in methods for selection and screening of mutagenized genes and proteins.

The selection, identification, and evolution of in vitro modified biological receptors presents a significant experimental problem. In the broadest sense, this problem can be described as the linking or association of the genotype to its corresponding phenotype. This is a particular problem when large numbers of mutants are generated in a random or quasi-random process, such as in a combinatorial system.

A key step, therefore, in all combinatorial selection systems is the linkage of genetic information with its protein offspring. Phage display accomplishes this linkage by engineering the phage to display a small peptide on their coats. The phage contains the DNA encoding the display peptide as a part of their single-stranded viral DNA (G. P. Smith, *Science* 228:1315 (1985); C. F. Barbas, *Curr. Opin. Biotechnol.* 4:526 (1993)). Phage display is limited by the requirement that the displayed protein or peptide exist in an active conformation while covalently linked at its amino-terminus to phage coat protein. Additionally, the system is limited because proteins or peptides that would disrupt the structure of the coat protein would not be detected in this system. Phage display is also limiting because it requires the displayed protein to be active subsequent to secretion through the bacterial membrane. The displayed protein must be competent for secretion. In addition, the displayed protein must be biologically active in the macromolecular context of the phage coat.

A second approach to the problem of linking genotype to phenotype has been suggested by the peptide-on-plasmid technology (M. G. Cull et al., "Screening for Receptor Ligands Using Large Libraries of Peptides Linked to the C Terminus of the lac Repressor," *Proc. Natl. Acad. Sci. USA* 89:1865–1869 (1992); P. J. Schatz, "Use of Peptide Libraries to Map the Substrate Specificity of a Peptide-Modifying Enzyme: A 13 Residue Consensus Peptide Specifies Biotinylation in *Escherichia coli,*" *Bio/Technology* 11:1138–1143 (1993); U.S. Pat. No. 5,270,170 to Schatz et al., issued Dec. 14, 1993). In the peptide-on-plasmid system, random peptide sequences are cloned onto the carboxyl terminus of the lac repressor. The DNA binding activity of the lac repressor is used to link the peptides to the plasmids encoding them by binding to Lac operator sequences on the plasmids. Combinatorial libraries of peptides-on-plasmids are prepared from up to $10^8$ *E. coli* transformants, which are harvested in-batch, gently lysed, and screened by conventional ligand affinity procedures, a process known as "panning." For the panning process to succeed, the fusion protein must remain connected to the plasmid. However, the half-life of the complex is only approximately 30 minutes, due to the non-covalent DNA-protein complex thus formed. In the normal panning methodology, sufficient time elapses to allow dissociation and re-association with an incorrect partner. In addition, lac binds to DNA as a tetramer, thus allowing mixed tetramers to form during and after the panning process. Thus, the linkage of one gene to its protein offspring is not insured and errors can be introduced.

As indicated above, the need for such techniques has grown as technologies for developing large libraries of nucleic acids and peptides have been developed. In particular, these libraries have proven useful for the isolation of ligands that bind biological receptors. The isolation of such ligands is critical in understanding signal transduction and in discovering new therapeutic substances and new therapeutic applications of previously known substances. In particular, the ability to synthesize DNA chemically has made possible the construction of extremely large collections of nucleic acid and peptide sequences as potential ligands. Recently developed methods allow efficient screening of libraries for desired binding activities (Pluckthun & Ge, *Angew. Chem. Int'l. Ed. Engl.* 30:296–298 (1991)). Other techniques, such as nucleic acid amplification techniques, particularly polymerase chain reaction (PCR) methodology, have also contributed to this area. For example, RNA molecules with the ability to bind a particular protein (Tuerk & Gold, *Science* 249:505–510 (1990)) or a dye (Ellington & Szostak, *Nature* 34:818–822 (1990)) have been selected by alternate rounds of affinity selection and PCR amplification. A similar technique was used to determine the DNA sequences that bind to human transcription factor (Thiesen & Bach, *Nucl. Acids Res.* 18:3203–3209 (1990)).

The power of nucleic acid synthesis, screening and amplification techniques such as PCR and solid-phase nucleic acid synthesis, greatly increases the need for an efficient and reliable method of linking nucleic acid segments to the proteins or peptides which they encode. There is also a need for plasmids that are particularly suitable for use in such linking procedures. These linking procedures and the plasmids for use with them preferably are adaptable to screening and selection techniques, as well as amplification techniques such as PCR, to allow multiple rounds of mutagenesis and selection, to study in vitro evolution of proteins and peptides. The improved methods and plasmids for such linkage are preferably also usable with a wide variety of genes and do not depend on the particular properties of the gene, protein or peptide being expressed.

SUMMARY OF THE INVENTION

To meet these needs, I have developed plasmids and methods that provide covalent linkage between genetic information and peptides or proteins encoded by the genetic information, resulting in a plasmid-polypeptide determinant conjugate. The linkage is stable, allowing both the plasmid and the polypeptide determinant to be manipulated.

One aspect of the present invention is a plasmid comprising, in general:

(1) a gene fusion construct including a DNA binder gene and polypeptide determinant gene covalently joined thereto, the gene fusion construct encoding a gene fusion product including a DNA binder peptide having a DNA binding activity and a polypeptide determinant covalently joined thereto, the DNA binder polypeptide being a polypeptide other than a subunit of lac repressor;

(2) a promoter operatively linked to the gene fusion construct promoting transcription of the gene fusion construct as messenger RNA; and (3) a binding element linked to the gene fusion construct, the binding element being capable of binding the DNA binder polypeptide of the gene fusion product.

More specifically, a plasmid according to the present invention comprises:

(1) a gene fusion construct including a gene encoding a DNA methylase and a gene encoding a polypeptide determinant covalently joined, either directly or through a linker, the gene fusion construct encoding a gene fusion product including a cytosine (C-5) DNA methylase having a methyltransferase activity and a polypeptide determinant covalently joined thereto, either directly or through a peptide linker;

(2) a promoter operatively linked to the gene fusion construct for promoting transcription of the gene fusion construct as messenger RNA; and (3) a methylase conjugation element linked to the gene fusion either directly or through an intervening sequence, the methylase conjugation element including a methylase binding site having at least one copy of a nucleotide sequence including a cytidine suicide analog capable of irreversibly binding the cytosine (C-5) DNA methylase within the gene fusion product.

Typically, the cytidine suicide analogue is 2'-deoxy-5-fluorocytidine, 2'-deoxy-5-azacytidine, or 2'-pyrimidinone-1-β-D-2-deoxyriboside. Preferably, the cytidine suicide analog is 2'-deoxy-5-azacytidine; an alternative is 2'-deoxy-5-fluorocytidine.

Typically, the methylase conjugation element includes 1 to 50 copies of the methylase binding site having a specificity for the cytosine (C-5) DNA methylase. More typically, the methylase conjugation element includes 3 to 20 copies of the methylase binding site; preferably, it includes 4 to 6 copies of the methylase binding site.

The gene fusion construct can have the DNA methylase gene covalently joined contiguously in-frame to the polypeptide determinant gene with a linking orientation selected from the group consisting of a first orientation with the 5'-terminus of the DNA methylase gene covalently joined to the 3'-terminus of the polypeptide determinant gene and a second orientation in which the 3'-terminus of the DNA methylase gene is covalently linked to the 5'-terminus of the polypeptide determinant gene.

The cytosine (C-5) DNA methylase can be one of Aqu I, Eag I, Eco 72 I, Hga I-1, Hga I-2, Hha I, Hpa II, Msp I, Nae I, Sss I, EcoR II, Hae III, NgoP II, Fnu D, Nla III, ScrF I, Sin I, Sso II, BsuF I, NgoM I, or Arabt. The nucleotide sequence of the methylase binding site of the methylase conjugation element is capable of serving as a substrate for the cytosine (C-5) DNA methylase used. Typically, the methylase is Msp I, Aqu I, or Hha I.

The gene fusion construct can include a linker for linking the DNA methylase gene to the polypeptide determinant gene, the linker encoding from 1 to 20 amino acids. Typically, the linker encoded by the gene fusion is from 5 to 20 amino acids and is of substantially α-helical secondary structure. Typically, the amino acids of the linker are selected from the group consisting of glycine, valine, isoleucine, leucine, and alanine. In one alternative, the linker is polyglycine. In another alternative, the linker has the sequence G-I-D-P-P (SEQ ID NO: 5).

Typically, the promoter is a prokaryotic promoter capable of promoting transcription in *Escherichia coli*. A preferred promoter is the *E. coli* tac promoter; an alternative promoter is the bacteriophage T7 promoter.

Another aspect of the present invention is a plasmid-polypeptide determinant conjugate comprising a plasmid and a gene fusion product covalently conjugated to the plasmid via a pyrimidine moiety of a cytidine suicide analogue. The plasmid is the plasmid described above.

Alternatively, a plasmid-polypeptide determinant conjugate according to the present invention can comprise a plasmid and a gene fusion product covalently conjugated to the plasmid via a pyrimidine moiety of a cytidine suicide analogue, the plasmid including:

(1) a gene fusion construct including a DNA methylase gene and a polypeptide determinant gene covalently joined thereto, the gene fusion construct encoding a gene fusion product including a cytosine (C-5) DNA methylase having a methyltransferase activity and a polypeptide determinant covalently joined thereto;

(2) a promoter operatively linked to the gene fusion construct for promoting transcription of the gene fusion construct as messenger RNA; and (3) a framework region including at least one methylase binding site having a nucleotide sequence including a cytidine suicide analogue capable of irreversibly binding the cytosine (C-5) DNA methylase of the gene fusion product and having a methylation specificity for the cytosine (C-5) DNA methylase.

In this alternative, the plasmid can be pNRT2, the methylase encoded by the gene fusion construct can be Msp I, and the framework region of the plasmid can include Msp I binding sites at nucleotides 1038, 1072, 1627, 1869, 1979, 2046, 2080, 2484, 2674, 2700, 2847, 3288, 3355, 3747, 3988, 4096, 4465, 4715, and 4733, with at least one of these binding sites being conjugated to the polypeptide determinant through a cytidine suicide analog.

Another aspect of the present invention is a library comprising a plurality of plasmid-polypeptide determinant conjugates, each plasmid-polypeptide determinant conjugate including:

(1) an encoding plasmid molecule as described above; and (2) the gene fusion product encoded by the gene fusion construct and covalently bound to the plasmid.

In one particularly preferred alternative, each of the polypeptide determinant genes within the plurality of plasmid-polypeptide determinant conjugates can be derived from a single parent polypeptide determinant gene by random mutagenesis. The parent polypeptide determinant gene can code for any polypeptide, including, but not limited to, glutathione S-transferase, estrogen receptor, triose phosphate isomerase, thrombin, plasminogen, tissue plasminogen activator, streptokinase, human insulin, erythropoietin, thrombopoietin, a fibrinogen type III domain or a protein including a fibrinogen type III domain, a DNA binding domain or a protein including a DNA binding domain, a helix-turn-helix DNA binding domain or a protein including a helix-turn-helix DNA binding domain, interleukin, HIV reverse transcriptase, HIV protease, renin, elastase, subtilisin, α-lytic protease, hirudin, omatin, kistin, or eglin C. In one preferred alternative, the parent polypeptide determinant gene is glutathione S-transferase.

Another aspect of the present invention is a method for obtaining a purified plasmid-polypeptide determinant conjugate comprising the steps of:

(1) causing expression of a gene fusion product from members of a library of plasmids, each plasmid encoding a gene fusion product, to produce a plurality of polypeptide determinants, each polypeptide determinant being an expressed gene fusion product;

(2) forming an irreversible covalent joining of the polypeptide determinants of step (a) to the plasmids encoding them to form a library of plasmid-polypeptide determinant conjugates; and (3) isolating a plasmid-polypeptide determinant conjugate that binds a predetermined target moiety from the library of plasmid-polypeptide determinant conjugates.

In this method, the step of isolating the lasmid-polypeptide determinant conjugate that binds a predetermined target moiety from the library of plasmid-polypeptide determinant conjugates can include:

(a) isolating the library of plasmid-polypeptide determinant conjugates of step (2); and (b) contacting the library of plasmid-polypeptide determinant conjugates with the predetermined target moiety for a period sufficient to allow the polypeptide determinant and the predetermined target moiety to form a complex.

Another aspect of the present invention is a method for obtaining a purified plasmid encoding a polypeptide determinant that binds a predetermined target moiety. This method comprises:

(1) obtaining a purified plasmid-polypeptide determinant conjugate as described above; and (2) deproteinizing the plasmid-polypeptide determinant conjugate obtained to form a purified plasmid encoding a polypeptide determinant binding a predetermined target moiety.

Analogous methods can be used to isolate a library of plasmid-polypeptide determinant conjugates, or to obtain a purified gene-gene product conjugate in which the gene encodes the gene product. Alternatively, from an isolated plasmid-gene fusion product conjugate that binds a predetermined target moiety, a DNA fragment can be isolated that includes a polypeptide determinant gene linked to a methylase conjugation element with the gene fusion product covalently joined to the methylase conjugation element, and the resulting DNA fragment deproteinized to form a purified polynucleotide fragment encoding the polypeptide determinant. The purified polynucleotide fragment can then be inserted into an expression plasmid, which can be used for in vivo expression of the polypeptide determinant. The nucleotide sequence of the purified polynucleotide fragment can also be determined by standard methods. Fragments encoding essentially the gene fusion construct or the polypeptide determinant gene can be isolated.

As another alternative, a method of obtaining a nucleic acid fragment encoding a polypeptide determinant that binds a predetermined target moiety can comprise:

(1) causing expression of a gene fusion product from members of a library of plasmids, each plasmid encoding a gene fusion product, to produce a plurality of polypeptide determinants, each polypeptide determinant being an expressed gene fusion product;

(2) forming an irreversible covalent joining of the polypeptide determinants of step (a) to the plasmids encoding them to form a library of plasmid-polypeptide determinant conjugates;

(3) isolating a plasmid-polypeptide determinant conjugate that binds a predetermined target moiety from the library of plasmid-polypeptide determinant conjugates; and (4) amplifying a region of the plasmid in the isolated plasmid-polypeptide determinant conjugate of step (3) by a sequence-specific primer-based amplification method employing at least two primers to yield a nucleic acid fragment encoding a polypeptide determinant that binds the predetermined target moiety. The sequence-specific primer-based amplification method can be the polymerase chain reaction (PCR) technique.

Another aspect of the present invention is a method for obtaining a library of gene-gene product conjugates. The method comprises:

(1) causing expression of gene fusion products from each of a library of plasmids, each plasmid encoding a polypeptide determinant;

(2) forming an irreversible covalent joining of gene fusion products to the plasmids encoding the gene fusion products so that each gene fusion product is joined to the plasmid encoding it to form a library of plasmid-polypeptide determinant conjugates;

(3) isolating a library of plasmid-polypeptide determinant conjugates; and (4) from each member of the library of plasmid-polypeptide determinant conjugates, isolating a DNA fragment including a polypeptide determinant gene linked to a methylase conjugation element with the methylase conjugation element being joined to the gene fusion product to form a library of gene-gene product conjugates.

Another aspect of the present invention is a method for making a plasmid-polypeptide determinant conjugate. The method comprises:

(1) introducing a plasmid into a host cell to form a transformed cell, the host cell being capable of incorporating a cytidine suicide analog into its DNA to partially replace cytidine, the plasmid being the plasmid described above;

(2) growing the transformed cell on a defined medium including a cytidine suicide analogue to incorporate the cytidine suicide analogue into the methylase binding site;

(3) causing expression of the gene fusion product from the plasmid of the transformed cell; and (4) forming an irreversible covalent joining of the gene fusion product to the methylase binding site of the plasmid.

Another aspect of the present invention is a method for obtaining a nucleic acid segment encoding a polypeptide, the polypeptide having at least one property altered from a wild-type polypeptide. The method comprises:

(1) obtaining a nucleic acid segment encoding the wild-type polypeptide;

(2) subjecting the nucleic acid segment encoding the wild-type polypeptide to random mutagenesis to generate a plurality of mutagenized nucleic acid segments;

(3) constructing a library of plasmids as described above from the plurality of mutagenized nucleic acid segments;

(4) causing expression of the gene fusion product from each of the library of plasmids;

(5) forming an irreversible joining of the gene fusion product to the plasmid encoding the gene fusion product for each member of the library of plasmids, forming a library of plasmid-polypeptide determinant conjugates;

(6) isolating a plasmid-polypeptide determinant conjugate from the library of plasmid-polypeptide determinant conjugates that binds a predetermined target moiety in a manner such that only plasmid-polypeptide determinant conjugates that have a property altered when compared to the wild-type polypeptide bind the target moiety;

(7) deproteinizing the plasmid-polypeptide determinant conjugate obtained in step (6) to form a purified plasmid encoding a polypeptide determinant having an altered property; and (8) isolating from the purified plasmid of step (7) a nucleic acid segment that encodes a polypeptide determinant having at least one property altered when compared with the wild-type polypeptide determinant.

Alternatively, the method can omit the deproteinization step, in which case the isolation of the nucleic acid segment that encodes the polypeptide determinant having at least one altered property can be performed by amplifying the nucleic acid segment encoding the polypeptide determinant with the at least one altered property by a sequence-specific primer-based amplification method employing at least two primers, such as PCR.

The step of isolating the plasmid-polypeptide determinant conjugate that binds a predetermined target moiety in such a way that only the polypeptide determinant with at least one altered property binds the target moiety can comprise the step of binding the plasmid-polypeptide determinant conjugate to a ligand under conditions such that the wild-type polypeptide determinant does not bind to the ligand and only plasmid-polypeptide determinant conjugates with increased affinity for the ligand bind to the ligand.

The method can be repeated, subjecting the nucleic acid segment of step (8) encoding the polypeptide determinant with at least one altered property to further random mutagenesis to produce a plurality of doubly mutagenized nucleic acid segments, constructing a second library of plasmids, causing expression of the gene fusion product from each of the second library of plasmids, forming an irreversible covalent joining of each of the gene fusion products to the plasmid encoding for the gene fusion product to form a second library of plasmid-polypeptide determinant conjugates, isolating a plasmid-polypeptide determinant conjugate from the second library of plasmid-polypeptide determinant conjugates that binds a predetermined target moiety in such a way that neither the wild-type protein determinant nor the protein determinant encoded by the nucleic acid segment generated in the first cycle of selection binds the predetermined target moiety, and deproteinizing the plasmid-polypeptide determinant conjugate obtained in the second cycle of selection to form a purified plasmid encoding a doubly mutagenized polypeptide determinant.

The polypeptide determinant encoded by the doubly mutagenized nucleic acid segment can bind a ligand with an increased affinity so that the second isolation occurs under conditions such that neither the wild-type polypeptide moiety nor the polypeptide moiety encoded by the nucleic acid segment generated in the first cycle binds.

The nucleic acid segment produced can be amplified with a sequence-specific primer-based amplification technique employing at least two primers, such as the polymerase chain reaction (PCR) technique.

BRIEF DESCRIPTION OF THE DRAWINGS

These and other features, aspects, and advantages of the present invention will become better understood with reference to the following description, appended claims, and the accompanying drawings where:

FIG. 3 is the nucleotide sequence and amino acid residue sequence of the encoded fusion protein between glutathione S-transferase and the Msp I methylase, including the linker, shown in SEQ ID NOs 55 and 56, respectively.

FIGS. 4A through 4D is the wild-type glutathione S-transferase gene and protein sequences, presented for comparison and shown in SEQ ID NOs 57 and 58, respectively.

FIGS. 5A through 5D is the gene and protein sequences shown in SEQ ID NOs 59 and 60, respectively, of the mutated Msp I methylase that is part of the fusion protein.

FIGS. 8B-1 and 8B-2 is a diagram of the use of the splice-verlap extension technique to join any polypeptide determinant open reading frame (ORF) to any methylase (C-5) ORF or DNA binder ORF;

FIG. 10 is a diagram showing the results of PCR using primers to excise the Msp I methylase gene and add a linker sequence;

FIG. 11 is a diagram of the ligation step yielding plasmid pDE3;

FIG. 12 is a schematic diagram of the generation of a glutathione S-transferase gene attached to the carboxyl-terminus of Msp I methylase;

FIG. 15 is a schematic diagram of the insertion of a methylase conjugation element for Hha I methylase into a vector (SEQ ID NO:63);

FIG. 16 is the nucleic acid sequence of the linker fragment ligated into pNRT2 to clone in the methylase conjugation element for the methylases Hpa II or Msp I (SEQ ID NO:64);

FIG. 21 is a diagram showing, schematically, the screening of the library of plasmid-polypeptide determinant conjugates by affinity chromatography;

Figure 24A:
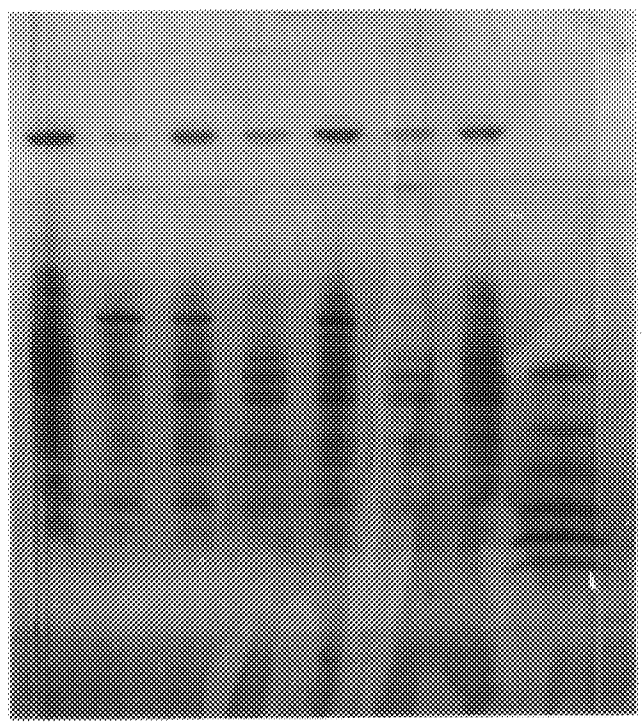
FIG. 24A is an electropherogram of proteins from uninduced and induced cells transfected with plasmid pNRT2 grown in minimal media with varying proportions of cytosine and 5-fluorocytosine.
Figure 24B:
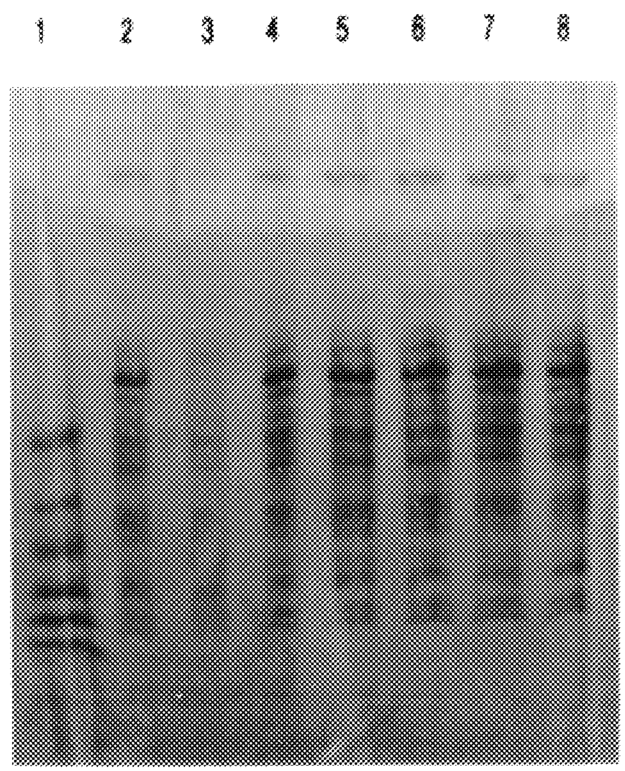
Figure 24C:
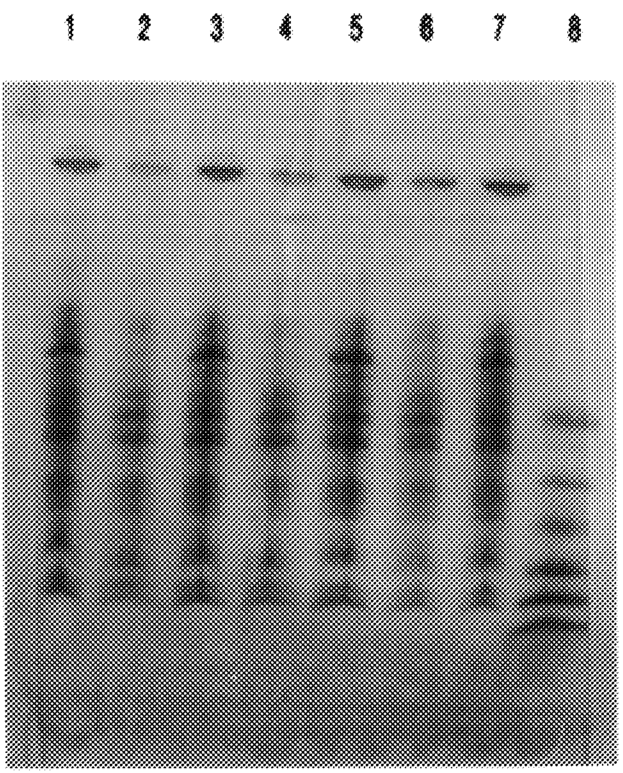

FIG. 24B is a second electropherogram of proteins as in FIG. 24A, with different proportions of cytosine and 5-fluorocytosine; and FIG. 24C is a third electropherogram of proteins as in FIG. 24A, with different proportions of cytosine and 5-fluorocytosine.

DESCRIPTION

DEFINITIONS

In the context of this disclosure, including the description, examples, and claims, the following terms are defined as follows unless otherwise indicated:

"Nucleic Acid Sequence" includes both DNA and RNA and, unless otherwise specified, includes both double-stranded and single-stranded nucleic acids. Also included are hybrids such as DNA-RNA hybrids. Reference to a nucleic acid sequence can also include modified bases as long as the modification does not significantly interfere either with binding of a ligand such as a protein by the nucleic acid or Watson-Crick base pairing. In particular, several substitutions for cytidine in DNA are described below.

"Gene Fusion Construct" means a segment of nucleic acid that codes for two or more polypeptides or domains that have independent origins and can be expressed independently or individually when not present in the gene fusion construct. The gene fusion construct can also include a segment encoding a linker peptide in such a way that the linker peptide is between two of the proteins or domains in the gene fusion construct.

"Polypeptide Determinant" refers to a single continuous chain of amino acids linked in peptide linkage. The polypeptide determinant can be an intact protein, either wild-type or created by mutagenesis, a structural or functional domain of a protein, a naturally occurring peptide, or a peptide fragment cleaved from a larger polypeptide or protein, such as by proteolytic cleavage. The polypeptide determinant can also be the result of synthesis.

"Contiguously" means without interruption of a single polypeptide chain in such a manner that the amino acids referred to as being contiguous or being joined contiguously are part of a single peptide chain produced by translation of a single messenger RNA molecule from a single open reading frame. The term "contiguous" or "contiguously" does not exclude the presence of linker peptides between two polypeptide determinants or proteins, as long as the combination of the two proteins or polypeptide determinants together with the linker peptide are translated from a single open reading frame to produce a single uninterrupted polypeptide chain.

"Irreversibly" means bound by covalent interactions in such a way that conditions that can break noncovalent interactions do not significantly reverse the binding. Typically, the energy required to break such covalent interactions is at least about 50 kcal/mole.

"Nucleic Acid Segment" includes both DNA and RNA unless specified to the contrary. In particular, a reference to DNA includes RNA that has either the equivalent base sequence except for the substitution of uracil in RNA for thymine in DNA, or has a complementary base sequence except for the substitution of uracil for thymine, complementarity being determined according to the Watson-Crick base pairing rules.

"Binding Site" is a site within a nucleic acid segment, such as a plasmid, that specifically binds a methylase and that contains a residue that is specifically methylated by the methylase.

I. BASIS OF THE LINKING REACTION

The DNA-methylase linking reaction that is the subject of the present invention allows one to isolate pharmacologically or physiologically important full-length proteins or domains of such proteins from a combinatorial or cDNA library of linked plasmid-DNA binder protein/fusion proteins. In the procedure, known as MLR, plasmid DNA becomes covalently linked, in vivo, to the DNA binder protein-fusion protein encoded within the same plasmid. Thus, the genetic information is irreversibly tagged to the protein encoded by the genetic information.

MLR allows rapid multiple-round selection of proteins or peptides of pharmacological or physiological interest, and it does not require the use of the phage display system. As discussed below, this novel system is particularly effective, for example, in selecting new glutathione S-transferase (GST) enzymes derived from the wild-type GST enzyme. GST is an important chemotherapy target. However, mutations in the enzyme lead to drug resistance. Thus, a method for screening the spectrum of anti-GST activity of a given drug is of significant utility to the pharmaceutical industry. The technique is also useful in screening for alternative forms of insulins, peptide hormones, or new industrial enzymes.

The new binding proteins and receptors produced can be applied in cell-type-specific gene therapy. They can also be used to screen the spectrum of binding affinities of inhibitors and inactivators useful as anti-neoplastic and anti-malarial agents targeted to GST.

The covalent linking method of the present invention uses trapping of covalent intermediates formed by DNA-modifying enzymes, particularly cytosine (C-5) methylases.

DNA methylases (DMases) are bacterial enzymes that catalyze the transfer of the activated methyl group of S-adenosylmethionine (Ado-Met) to the C-5 position of cytosine in DNA. In bacteria, DNA modification by methylation prevents digestion of host DNA by the host restriction endonucleases. DNA methylation binding/recognition sites are specific and typically, two, four, or six nucleotides in length. The genes for over 90 bacterial DNA methylases have been cloned and sequenced (G. G. Wilson & N. E. Murray, "Restriction and Modification Systems," *Annu. Rev. Genet.* 25:585–627 (1991)).

Figure 1:
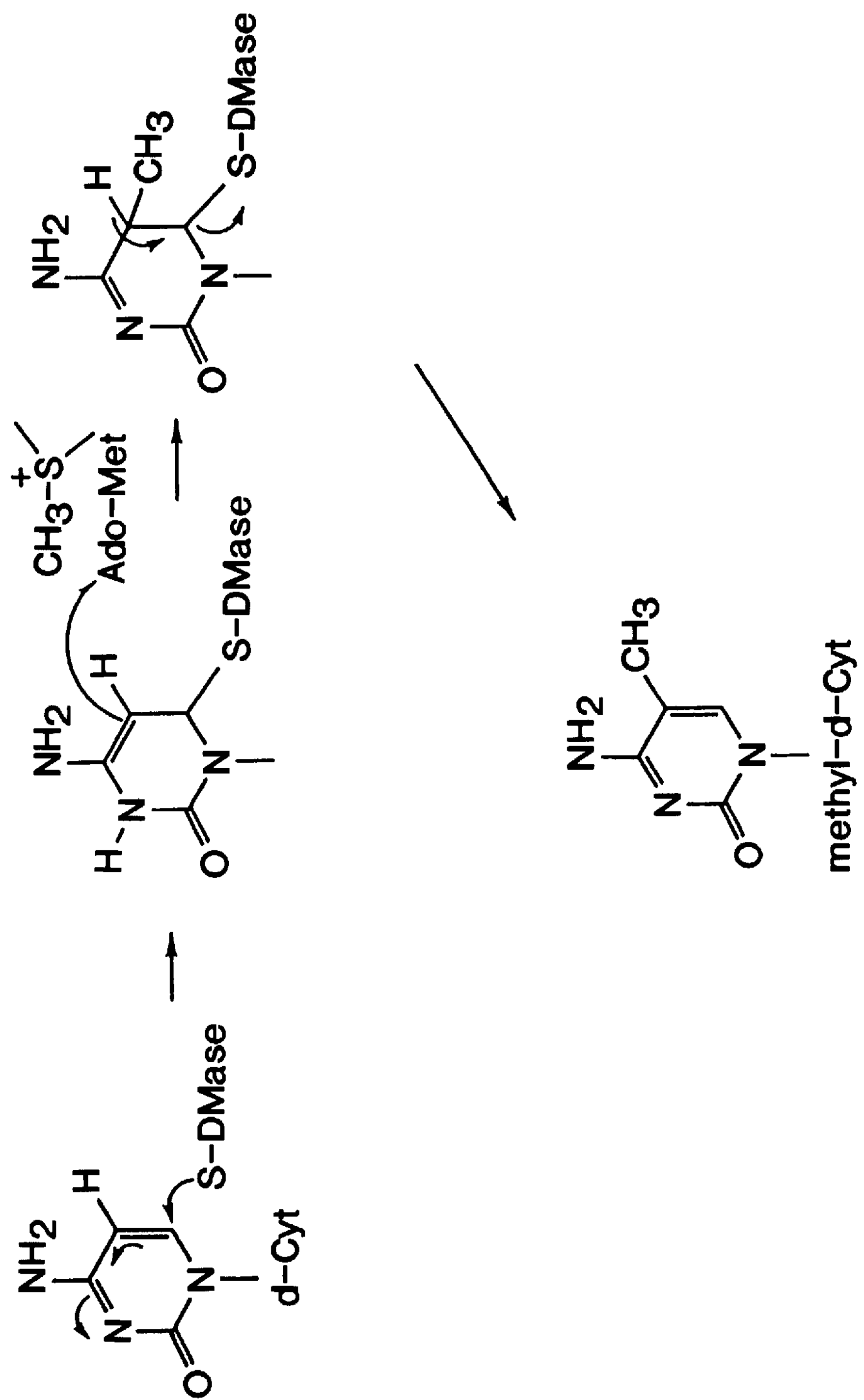
FIG. 1 is a schematic diagram of the cytosine methylation reaction carried out by cytosine methylases with S-adenosylmethionine as cofactor, showing structural formulas of the relevant reactants.

The mechanism of reaction for methylation of cytosine at the C-5 position is shown in Scheme 1 (FIG. 1). Upon DNA-enzyme complex formation, proton donation to N-3 of cytosine stabilizes Michael addition of an active site nucleophile, a thiol, to C-6. Addition of a methyl group to C-5 is provided by the cofactor S-adenosylmethionine (Ado-Met). Free enzyme and methylated DNA are then generated by proton removal from C-5 (J. C. Wu & D. V. Santi, "Kinetic and Catalytic Mechanism of Hha Methyltransferase," *J. Biol. Chem.* 262:4778–4786 (1987); L. Chen et al., "Direct Identification of the Active-Site Nucleophile in a DNA (Cytosine-5)-Methyltransferase," *Biochemistry* 30:11018–11925 (1991)).

Figure 2:
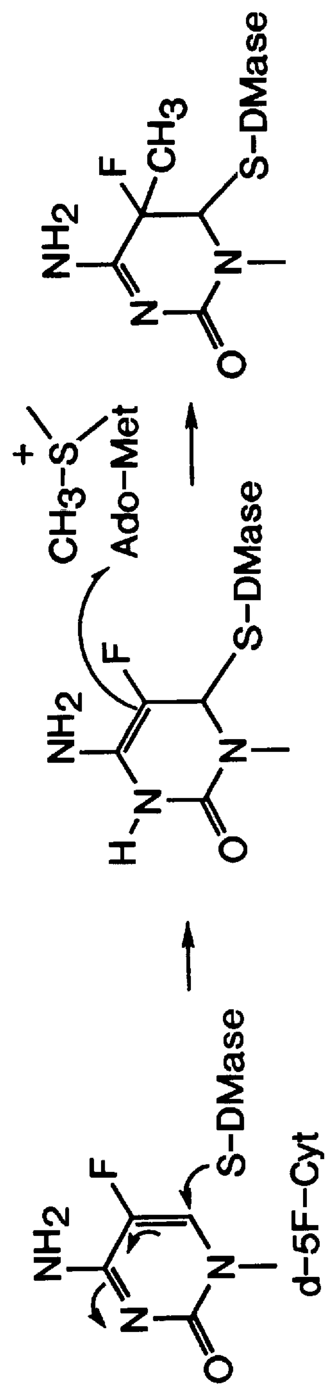
FIG. 2 is a schematic diagram of the inactivation of DNA methylase caused by the reaction of 5-fluorocytidine with the methylase, causing a covalent linkage of the enzyme with the 5-fluorocytidine residue, showing structural formulas.

The mechanism-based inactivation of DMase by 5-fluorocytosine in DNA is illustrated in Scheme 2 (FIG. 2). As noted above, reaction with substrate results in transient formation of a covalent enzyme-DNA intermediate. When the reaction occurs with 5-fluorocytosine-containing DNA, this covalent intermediate is formed and the methyl group is transferred to the C-5 position. However, irreversible inactivation occurs because the fluorine at position 5 cannot be released as $F^+$(D. G. Osterman et al., "5-Fluorocytosine in DNA Is a Mechanism-Based Inhibitor of Hha I Methylase," *Biochemistry* 27: 5204–5210 (1988)). During the course of this reaction, Ado-Met is converted to S-adenosylhomocysteine (Ado-Hcy), which stays bound in the complex (S. Klimasauskas et al., "Hha I Methyltransferase Flips Its Target Base Out of the DNA Helix," *Cell* 78:357–369 (1994)).

The mechanism of DMase inactivation by 5-azacytidine occurs by a similar mechanism (D. V. Santi et al., "On the Mechanism of Inhibition of DNA-Cytosine Methyltransferases by Cytosine Analogs," *Cell* 33: 9–10 (1983)). Similarly, the inactivation of DMases by 2-pyrimidinone-1-β-D-2'-deoxyriboside occurs by a mechanism-based reaction pathway. In all cases a covalent bond is formed between a reactive sulfhydryl group on the methylase enzyme and the C-6 carbon of the pyrimidine base.

A. Suitable Enzymes

1. Methylases

Particularly suitable enzymes for the plasmids and methods of the present invention are cytosine methylases that methylate the 5-position of cytosine in DNA, typically double-stranded DNA. A number of suitable DNA methylases are known. These include, from prokaryotic sources, Aqu I, Eag I, Eco 72 I, Hga I-1, Hga I-2, Hha I, Hpa II, Msp I, Nae I, Sss I, EcoR II, Hae III, NgoP II, Fnu D, Nla III, ScrF I, Sin I, Sso II, BsuF I, and NgoM I. Still other methylases are known from eukaryotic sources, such as the methylase Arabt from *Arabidopsis thaliana* (E. J. Finnegan & E. S. Dennis, "Isolation and Identification by Sequence Homology of a Putative Cytosine Methyltransferase from *Arabidopsis thaliana,*" *Nucl. Acids Res.* 21: 2383–2388 (1993). This enzyme recognizes the sequence C-G and C-N-G, where N is any of A, C, G, or T. It is likely that, in the future, additional DNA cytosine (C-5) methylases will be discovered, cloned, and sequenced.

Particularly preferred methylases include Msp I, Aqu I, and Hha I. These are all monomeric enzymes of approximately 30 kDa. The Msp I, Aqu I, and Hha I genes have been cloned, sequenced, and overexpressed in *Escherichia coli*. Significantly, it has been shown that Msp I and Aqu I are active as fusion proteins. Both of these methylases are active when glutathione-S-transferase is fused to either the C- or N-terminus.

It is generally preferred to use methylases that recognize four or more bases. However, in some cases, it is desirable to use methylases whose recognition sites include fewer bases. This means that sites of methylation occur more frequently in any stretch of DNA.

The cloning of the gene for Msp I methylase is disclosed in P. M. Lin et al., "Cloning and Characterization of the Genes Encoding the MspI Restriction Modification System," *Nucl. Acids Res.* 17: 3001–3011 (1989). Msp I methylase methylates at the sequence C-C-G-G, with the first cytosine being methylated. See also C. Taylor et al., "Determination of the Order of Substrate Addition to Msp I DNA Methyltransferase Using a Novel Mechanism-Based Inhibitor," *Biochem. J.* 291:493–504 (1993).

The cloning of the gene for Aqu I methylase is disclosed in C. Karreman & A. de Waard, "*Agmenellum quadruplicatum* M·AquI, a Novel Modification Methylase," *J. Bacteriol.* 172: 266–272 (1990). Aqu I methylase methylates at the sequences C-C-C-G-G-G and C-T-C-G-A-G, with the first cytosine in each sequence being methylated. This enzyme is a heterodimer of two polypeptides, the polypeptides being translated from partially overlapping reading frames.

The cloning of the gene for Hha I methylase is disclosed in M. Caserta et al., "Cloning, Sequencing, in Vivo Promoter Mapping, and Expression in *Escherichia coli* of the Gene for the HhaI Methyltransferase," *J. Biol. Chem.* 262: 4770–4777 (1987). Hha I methylase methylates at the sequence G-C-G-C, with the first cytosine being methylated.

Eag I methylase methylates at the sequence C-G-G-C-C-G, with the site of methylation within the sequence not yet determined.

Eco72 I methylase methylates at the sequence C-A-C-G-T-G, with the site of methylation within the sequence not yet determined.

The cloning of the genes for Hga I-1 and Hga I-2 is disclosed in H. Sugisaki et al., "The HgaI Restriction-Modification System Contains Two Cytosine Methylase Genes Responsible for Modification of Two Different DNA Strands," *J. Biol. Chem.* 266: 13952–13957 (1991). Hga I-1 methylase methylates at the sequence C-T-G-C-G, with the second cytosine (residue 4 of the sequence) being methylated. Hga I-2 methylase methylates at the sequence G-A-C-G-C, with the first cytosine (residue 3 of the sequence) being methylated.

The cloning of the gene for Hpa II methylase is disclosed in C. O. Card et al., "Cloning and Characterization of the HpaII Methylase Gene," *Nucl. Acids Res.* 18: 1377–1383 (1990). Hpa II methylase methylates at the four-base sequence C-C-G-G, with the second cytosine being methylated; this enzyme is therefore an isoschizomer of Msp I, although the site of methylation is different.

The cloning of the genes for FnuD I, Nae I, and Nco I methylases is disclosed in E. M. Van Cott & G. G. Wilson, "Cloning the FnuDI, NaeI, NcoI and XbaI Restriction-Modification Systems," *Gene* 74: 55–59 (1988). The FnuD I methylase methylates at the four-base sequence G-G-C-C, the Nae I methylase methylates at the six-base sequence G-C-C-G-G-C, and the Nco I methylase methylates at the six-base sequence C-C-A-T-G-G. The FnuD II methylase methylates at the four-base sequence C-G-C-G, with methylation occurring at the first cytosine.

The cloning of the gene for Sss I methylase is disclosed in P. Renbaum et al., "Cloning, Characterization and Expression in *Escherichia coli* of the Gene Coding for the CpG DNA Methylase from *Spiroplasma sp.* Strain MQ1 (M·SssI)," *Nucl. Acids Res.* 18: 1145–1152 (1990). The Sss I methylase methylates the cytosine in the two-base sequence C-G.

The cloning of the gene for EcoR II methylase is disclosed in S. Som et al., "Nucleotide Sequence and Expression of the Gene Encoding the EcoRII Modification System," *Nucl. Acids Res.* 15: 313–332 (1987). The EcoR II methylase methylates at the sequences C-C-W-G-G, where W is A or T. In either case, the second cytosine in the sequence (residue 2) is methylated.

The cloning of the gene for Hae III methylase is disclosed in B. E. Slatko et al., "Cloning and Analysis of the HaeIII and HaeII Methyltransferase Genes, " *Gene* 74: 45–50 (1988). The Hae III methylase methylates at the sequence G-G-C-C, with the first cytosine (residue 3) being methylated.

The NgoP II methylase is described in N. Ritchot & P. H. Roy, "DNA Methylation in *Neisseria gonorrhoeae* and Other Neisseriae," *Gene* 56: 103–106 (1990); J. S. Gunn & D. C. Stein, "Natural Variation of the NgoII Restriction-Modification System of *Neisseria gonorrhoeae,*" *Gene* 132:

15–20 (1993); K. M. Sullivan & J. R. Saunders, "Nucleotide Sequence and Genetic Organization of the NgoPII Restriction-Modification System of *Neisseria gonorrhoeae,*" *Mol. Gen. Genet.* 216: 380–387 (1989); and D. C. Stein et al., "Construction of a *Neisseria gonorrhoeae* MS11 Derivative Deficient in NgoMI Restriction and Modification," *J. Bacteriol.* 174: 4899–4906 (1992). The NgoP II methylase methylates at the sequence G-G-C-C, with the second cytosine (residue 4) being methylated.

The cytosine-specific Nla III methylase is described in D. Labbe et al., "Cloning and Characterization of Two Tandemly Arranged DNA Methyltransferase Genes of *Neisseria lactamica*: An Adenine-Specific M.NlaIII and a Cytosine-Type Methylase," *Mol. Gen. Genet.* 224: 101–110 (1990). The Nla III cytosine-specific methylase recognizes the sequence C-A-T-G, with residue 1, the only cytosine, being methylated.

The cloning and sequencing of the gene for the ScrF I methylase are described in D. P. Twomey et al., "Sequence of the Gene Encoding a Second ScrFI $m^5C$ Methyltransferase of *Lactococcus lactis,*" *Gene* 136: 205–209 (1993). The ScrF I methylase recognizes the sequence C-C-N-G-G, where N is any of A, C, G, or T. The site of methylation has not yet been determined.

The cloning of the gene for Sin I methylase is disclosed in C. Karreman & A. de Waard, "Cloning and Complete Nucleotide Sequences of the Type II Restriction-Modification Genes of *Salmonella infantis,*" *J. Bacteriol.* 170: 2527–2532 (1988). The Sin I methylase recognizes the sequences G-G-W-C-C, where W is A or T; the actual site of methylation has not yet been determined.

The sequencing of the gene for the Sso II methylase is disclosed in A. S. Karyagina et al., "Analysis of the Nucleotide and Derived Amino Acid Sequences of the SsoII Restriction Endonuclease and Methyltransferase," *Gene* 124: 13–19 (1993). The Sso II methylase recognizes the sequence C-C-N-G-G, where N is any of A, C, G, or T. The second cytosine (residue 2) is methylated.

The amino acid sequence of the BsuF I methylase is disclosed in J. Walter et al., "The Amino Acid Sequence of the CCGG Recognizing DNA Methyltransferase M. BsuFI: Implications for the Analysis of Sequence Recognition by Cytosine DNA Methyltransferases," *EMBO J.* 9: 1007–1013 (1990). The BsuF I methylase recognizes the sequence C-C-G-G, with the first cytosine (residue 1) being methylated.

2. Other Enzymes

Other nucleic acid modifying enzymes that form covalent intermediates with DNA can be used in the invention with suitable nucleotide analogs. These enzymes include DNA N-glycosylases, integrases, such as bacteriophage λ integrase, and topoisomerases. Other enzymes methylate tRNA. These include cytosine and uracil C-5 methylases specific for tRNA modification.

Other enzymes of these classes that are suitable include HIV integrase, which can be expressed in *E. coli* (V. Ellison & P. O. Brown, "A Stable Complex Between Integrase and Viral DNA Ends Mediates Human Immunodeficiency Virus Integration In Vitro," *Proc. Natl. Acad. Sci. USA* 91:7316–7320 (1994)) and the enzymes formamidopyrimidine DNA N-glycosylase and uracil DNA-glycosylase (Z. Hatahet, "New Substrates for Old Enzymes," *J. Biol. Chem.* 269:18814–18820 (1994)).

B. Suitable Mechanism-Based Inhibitors or Suicide Substrates

For methylases, suicide substrates include cytidine analogs such as 2'-deoxy-5-fluorocytidine, 2'-deoxy-5-azacytidine, and 2-pyrimidinone-1-β-D-2-deoxyriboside. These substrates are referred to generically as cytidine suicide analogs. A particularly preferred cytidine suicide analog is 2'-deoxy-5-azacytidine. Conditions for the in vivo use of these cytidine suicide analogs are discussed below in Section V.

II. PLASMIDS

One aspect of the present invention is plasmids suitable for performing the linking and selection processes of the present invention. These plasmids are designed so that linkage occurs in vivo between the plasmid and a fusion protein encoded by the plasmid. In general, plasmids according to the present invention comprise:

(1) a gene fusion construct including a DNA binder gene and polypeptide determinant gene covalently joined thereto, the gene fusion construct encoding a gene fusion product including a DNA binder peptide having a DNA binding activity and a polypeptide determinant covalently joined thereto, the DNA binder polypeptide being a polypeptide other than a subunit of lac repressor;

(2) a promoter operatively linked to the gene fusion construct promoting transcription of the gene fusion construct as messenger RNA; and (3) a binding element linked to the gene fusion construct, the binding element being capable of binding the DNA binder polypeptide of the gene fusion product.

Typically, the DNA binder polypeptide is a DNA methylase and the binding element is a DNA sequence that specifically binds a DNA methylase. Thus, the plasmid typically comprises:

(1) a gene fusion construct including a gene encoding a DNA methylase and a gene encoding a polypeptide determinant covalently joined, either directly or through a linker, the gene fusion construct encoding a gene fusion product including a cytosine (C-5) DNA methylase having a methyltransferase activity and a polypeptide determinant covalently joined thereto, either directly or through a peptide linker;

(2) a promoter operatively linked to the gene fusion construct for promoting transcription of the gene fusion construct as messenger RNA; and (3) a methylase conjugation element linked to the gene fusion either directly or through an intervening sequence, the methylase conjugation element including a methylase binding site having at least one copy of a nucleotide sequence including a cytidine suicide analog capable of irreversibly binding the cytosine (c-5) DNA methylase within the gene fusion product.

A. The Gene Fusion Construct

The gene fusion construct includes a gene for an enzyme capable of covalent interaction with DNA that can be trapped covalently and stably by reaction with a base analog, covalently joined to a polypeptide determinant gene. Typically, the enzyme capable of covalently binding to DNA and being trapped is a DNA methylase, as described above, and having a methyltransferase activity.

1. The Polypeptide Determinant

The polypeptide determinant can be any single polypeptide chain expressible in a prokaryotic system, generally *E. coli*. There are no fixed length restrictions on the polypeptide determinant; it can be a short peptide or a long protein chain. It can be an intact protein or single subunit of a multi-subunit protein. Alternatively, it can be a structural or functional domain of a protein, or a fragment of a protein or peptide produced by proteolytic cleavage, either chemical or enzymatic. The polypeptide determinant can also be a synthetic or naturally occurring peptide. Typical polypeptide determinants include, but are not necessarily limited to, glutathione S-transferase, estrogen receptor, triose phosphate isomerase, thrombin, plasminogen, tissue plasminogen activator, streptokinase, human insulin, erythropoietin, thrombopoietin, a fibrinogen type III domain or a protein including a fibrinogen type III domain, a DNA binding domain or a protein including a binding domain, a helix-turn-helix DNA binding domain or a protein including a helix-turn-helix DNA binding domain, interleukin, interferon, HIV reverse transcriptase, HIV protease, renin, elastase, subtilisin, α-lytic protease, hirudin, omatin, kistin, and eglin C.

As discussed below, the polypeptide determinant can be mutated from a naturally occurring or wild-type polypeptide determinant by mutagenesis.

A particularly preferred polypeptide determinant is the gene for schistosomal glutathione S-transferase (GST) from *Schistosoma japonicum.*

GST from *S. japonicum* is an important anti-parasitic chemotherapy target. Over 200 million people are affected by this parasite. GST is an important locus for drug resistance, because it plays a key role in the xenobiotic response to drug treatment. Drug resistance in Schistosoma arises rapidly due to spontaneous mutation within the GST substrate binding site.

Thus, methods which screen the spectrum of drug anti-GST activity as a function of GST active site mutations, through the study of entire populations of GST variants, are of great utility. See A. L. Hughs, "Rates of Evolution in the 26- and 28-kDa Glutathione S-Transferases of Schistosoma," *Mol. Biochem. Parasitol.* 58: 43–52 (1993). Presently, Schistosoma GST is a key drug target for the design of Schistosoma-selective GST inhibitors. Newly designed inhibitors will exploit the differences between mammalian and schistosomal GST drug-binding sites. Likewise, mammalian GST remains a key cancer chemotherapeutic target.

2. The Peptide Linker

Optionally, the gene fusion construct includes a linker for linking the DNA methylase gene to the polypeptide determinant When present, the linker forms a continuous open reading frame in the gene fusion construct with the polypeptide determinant and the DNA methylase gene so that a single polypeptide chain results from translation. The single polypeptide chain contains the linker between the polypeptide determinant and the DNA methylase. Typically, the linker contains from 1 to 20 amino acids. More typically, the linker contains from 5 to 20 amino acids and the amino acids encoded by the linker are present in substantially α-helical conformation when the gene fusion construct is expressed as a polypeptide chain. Preferably, the amino acids found in the linker, therefore, are those that do not interfere with formation of α-helical structure. Particularly favored are amino acids such as glycine, alanine, leucine, isoleucine, and valine. These amino acids, other than glycine, are relatively nonreactive and hydrophobic. A particularly preferred amino acid in the linker is glycine, and a particularly preferred linker is therefore polyglycine.

Although in general it is preferred to have relatively unreactive hydrophobic α-helix forming residues in the linker, for some applications it can be desirable to have charged or other reactive amino acids or α-helix-disrupting amino acids such as proline in the linker.

For examples in the present invention, the disclosed linker has the sequence G-I-D-P-P (SEQ ID NO: 5) and is fully functional.

3. The Linking Orientation

The DNA methylase gene and the polypeptide determinant gene are covalently joined contiguously in the gene fusion construct, including any intervening peptide linker, so that the DNA methylase gene and the polypeptide determinant form a single open reading frame and are thus contiguous as that term is defined herein. As indicated above in the definition of "contiguous", this does not exclude the possibility of having a peptide linker. The DNA methylase gene and the polypeptide determinant gene can be joined in either a first linking orientation or a second linking orientation. In the first linking orientation, the 5'-terminus of the DNA methylase gene is covalently joined to the 3'-terminus of the polypeptide determinant gene, either directly or through an intervening linker. In the second linking orientation, the 3'-terminus of the DNA methylase gene is covalently joined to the 5'-terminus of the polypeptide determinant gene, either directly or through an intervening linker.

B. The Promoter

The plasmid further includes a promoter operatively linked to the gene fusion construct for promoting transcription of the gene fusion construct as messenger RNA. The promoter is typically a promoter that efficiently promotes transcription of messenger RNA in prokaryotic systems, such as *E. coli*. Suitable strains of *E. coli* are described below in Section V. A particularly preferred promoter is *E. coli* tac promoter (E. Amann et al., "Vectors Bearing a Hybrid trp-lac Promoter Useful for Regulated Expression of Cloned Genes in *Escherichia coli,*" *Gene* 25: 167 (1983); H. A. de Boer et al., "The tac promoter: A Functional Hybrid Derived from the trp and lac Promoters," *Proc. Natl. Acad. Sci. USA* 80: 21 (1983)), although other promoters active in *E. coli* can also be used, for example bacteriophage promoters such as T7 promoter. Alternatively, other prokaryotic promoters can be used. Optionally, other control elements can also be present.

C. The Methylase Conjugation Element

The plasmid of the present invention further includes a methylase conjugation element linked to the gene fusion construct. The methylase conjugation element includes a methylase binding site having a nucleotide sequence including a cytidine suicide analog capable of irreversibly and covalently binding the cytosine (C-5) DNA methylase that is encoded by the gene fusion construct and that is present in the gene fusion product. The nucleotide sequence of the methylase binding site is, therefore, a substrate for the methylase present in the gene fusion product. When a cytidine analog containing an electrophilic group at C-5 (i.e., F, Br, I, CN) is incorporated into the DNA at the nucleotide sequence of the methylase binding site, then the binding site is a suicide substrate for the encoded methylase. This results in the covalent linkage described above. The methylase conjugation element can include from 1 to 50 copies of the methylase binding site, with up to 10% of the binding sites containing the cytidine analog.

Typically, the methylase conjugation element has from 3 to 20 copies of the methylase binding site, more typically from 4 to 6 copies, any or all of which may have the cytidine analog incorporated at the cytosine methylation site.

The plasmid within the complex can also include copies of the methylase binding site within the remainder of the plasmid, either within the methylase gene itself, or within the framework regions of the plasmid (i.e., those regions not within the promoter, the methylase gene, the polypeptide determinant gene, or the linker). For example, the Msp I methylase gene itself includes one Msp I binding site, at codon 387. The pGEX-3X plasmid, into which the gene fusion construct can be cloned, as discussed below, has 19 Msp I (or Hpa II) binding sites at nucleotides 1038, 1072, 1627, 1869, 1979, 2046, 2080, 2484, 2674, 2700, 2847, 3288, 3355, 3747, 3988, 4096, 4465, 4715, and 4733. These methylase binding sites can be used to covalently link plasmids to polypeptides when an appropriate suicide substrate analog is incorporated into the position of cytosine methylation within the binding site. In general, it is preferred to link the polypeptide to the plasmid through a methylase binding site a methylase conjugation element or in the framework region of the plasmid to provide an optimum environment for subsequent manipulation of the plasmid.

Binding sites for other methylases also exist within the methylase genes themselves and within the framework regions of pGEX-3X and other vectors. The number of binding sites for a number of methylases within pGEX-3X and within the gene coding for the methylase is shown in Table 1.

TABLE 1

FREQUENCY OF OCCURRENCE OF METHYLASE RECOGNITION SITES IN PLASMID pGEX-3X AND IN GENE ENCODING METHYLASE

| Enzyme | pGEX-3X | Gene |
|---|---|---|
| Aqu I | O | — |
| EcoR I | 2 | 1 |
| Hha I | 34 | 0 |
| Hga I-1 | 3 | 1 |
| Hga I-2 | 8 | 1 |
| Hpa II | 20 | 2 |
| Msp I | 20 | 1 |
| NgoP II | 20 | 2 |
| Nla III | 22 | 0 |
| Nae I | 0 | 1 |
| Scrf I | 19 | — |
| Sin I | 4 | — |

The binding sequences for a large number of cytosine (C-5) methylases are known. Generally, these sequences are four- to six-base sequences including a cytosine residue It is this cytosine residue to which the methyl group is transferred (to C-5) during the course of the normal methyltransferase reaction and to which the enzyme becomes irreversibly covalently linked (to C-6) during the linking reaction. For Msp I, the sequence is C-C-G-G, with the first cytosine being methylated. For Hpa II, an isoschizomer of Msp I, the second cytosine (i.e., the internal cytosine) is methylated.

D. Construction of a GST-Msp I Expression Vector

Cloning procedures for the construction of plasmids containing a polypeptide determinant, such as glutathione S-transferase, and the Msp I methylase, so that a fusion protein can be expressed, and optionally, a methylase conjugation element, use modifications of generally known methods for expression cloning. One such cloning scheme starts with a 2.9-kb Eco RI-Hind III restriction fragment including the Msp I restriction and modification genes, also including a Eco RI site. PCR amplification is then used to introduce mutations, and the mutated segment is inserted in the plasmid pGEX-3X. This cloning scheme is described further in Example 1.

The sequences of the resulting nucleotide segment and encoded fusion protein are shown in FIG. 3A through 3D, including the factor X cleavage site near the carboxy-terminal end of the glutathione transferase and the linker. For comparison, the sequences of the wild-type Msp I methylase gene and protein are shown in FIG. 4A through 4D, and the sequences of the mutated Msp I methylase portion of the fusion protein are shown in FIG. 5A through 5D.

E. Cloning of a Methylase Conjugation Element into pNRT2

A methylase conjugation element can then be cloned into the pNRT2 vector by cloning into the EcoR I site. This site is near the 3'-end of the insert at the 3'-end of the methylase gene. This procedure is described further below in Example 2.

F. Cloning of Alternative DNA C-5 Methylases into pGEX-3X

Figure 6:
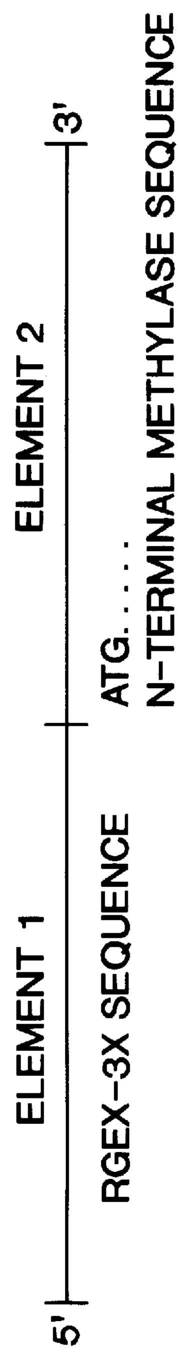
FIG. 6 is a schematic diagram of the 5'-primer sequence for PCR cloning of another methylase into pGEX-3X to replace the Msp I methylase.

The Msp I methylase can be replaced by other DNA (C-5) methylases or DNA binder genes of interest by placing them in-frame into pGEX-3X, using PCR. In general, the procedure for cloning of other DNA cytosine (C-5) methylases fused contiguously to the 3'-end of the glutathione S-transferase gene comprises:

(1) Performing PCR on fragments of DNA containing the methylases or DNA binder genes of interest. The fragments to be used for a number of methylases are described in detail below. The 5'-PCR primers are consistent; they are composed of two elements. The first element on the 5'-end of the 5'-primer sequence is identical to the pGEX-3X linker sequence (i.e., the multiple cloning site); it contains the BamH I, Sma I, and EcoR I sites in-frame with the first methionine of the second element. The second element of the 5'-primer sequence is composed of the first 1 to 10 codons of the methylase or DNA binder gene to be inserted. A schematic diagram of the 5'-primer is shown in FIG. 6. Typically, the primer extends about five codons into the methylase, although a longer primer can be used.

Figure 7:
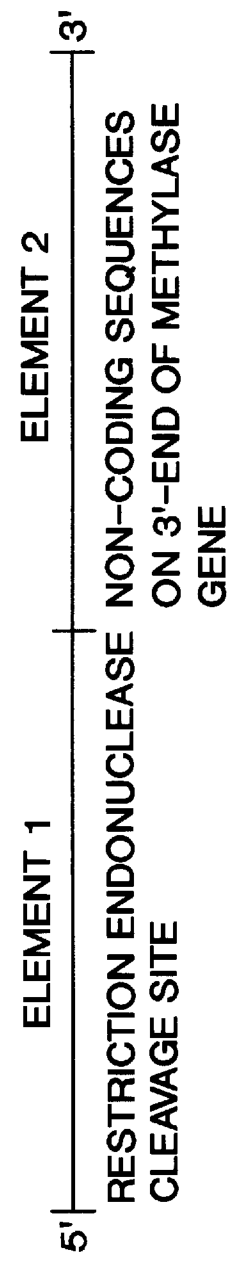
FIG. 7 is a schematic diagram of the 3'-primer sequence for PCR cloning of another methylase into pGEX-3X to replace the Msp I methylase.

The 3'-primers are similarly constructed, only using the non-coding strand sequences. The first element contains a restriction site necessary for cloning the methylase conjugation element and necessary for cloning into pGEX-3X. The second element of the 3'-primer is homologous to the non-coding strand of the gene to be inserted and has an EcoR I site. A schematic diagram of the 3'-primer is shown in FIG. 7.

(2) Insertion of the PCR product into the pGEX-3X vector. The PCR product has blunt ends. The product can be subcloned, isolated by digestion with EcoR I (or in some cases EcoR I and Sph I) and cloned into the EcoR I site of the pGEX-3X vector. Alternatively, the PCR product can be cleaved with EcoR I and cloned into the pGEX-3X vector. As another alternative, the blunt-ended PCR product can be cloned directly into pGEX-3X at the Sma I site; the resulting clone can then be redigested with BamH I and then religated to give the correct reading frame.

For the methylase Aqu I, a suitable 5'-primer is 5'-T-C-G-T-G-G-A-T-C-C-C-C-G-G-G-A-A-T-T-C-A-A-T-G-G-A-A-A-A-A-A-A-A-C-T-G-A-T-A-A-G-C-3' (SEQ ID NO: 6). In this primer, the first 22 bases are derived from the pGEX-3X linker sequence, and the remainder correspond to nucleotides 395 to 416 of the coding strand of Aqu I ethylase (C. Karreman & A. de Waard (1990), supra). The 3'-primer can be 5'-T-A-T-A-A-G-A-A-T-T-C-C-T-A-G-A-G-T-G-G-A-A-G-G-T-G-C-A-T-G-A-G-3' (SEQ ID NO: 7). The first 11 bases of this primer include an EcoR I cleavage site, and the remainder correspond to nucleotides 1191 to 1171 of the complementary non-coding strand of the α-subunit of Aqu I. The fragment to be amplified can be a fragment derived from the pAQ6,pMAQU, or pMAQUANTI plasmids by restriction endonuclease cleavage, e.g., by Hind III and Xba I from pMAQUANTI (C. Karreman & A. de Waard (1990), supra, p. 267).

For cloning the Arabidopsis methylase Arabt into pGEX-3X, a suitable 5'-primer is 5'-T-C-G-T-G-G-G-A-T-C-C-C-C-G-G-G-A-A-T-T-C-A-A-T-G-G-T-G-G-A-A-A-A-T-G-G-G-C-T-A-A-A-G-C-3' (SEQ ID NO: 8). The first 22 bases of this primer are again derived from the pGEX-3X linker sequence, and the remainder correspond to nucleotides 67 to 83 of the coding strand for the methylase (E. J. Finnegan & E. S. Dennis (1993), supra). A suitable 3'-primer is 5'-T-A-T-A-A-G-A-A-T-T-C-A-T-G-C-C-A-A-A-T-T-T-G-G-G-T-G-G-3' (SEQ ID NO: 9). The first 11 bases of this primer again include an EcoR I cleavage site, and the remainder correspond to nucleotides 4690 to 4676 of the non-coding strand for the nuclease. The DNA fragment to be amplified can be obtained from a clone by cleavage with BamH I (E. J. Finnegan & E. S. Dennis (1993), supra).

For cloning the EcoR II methylase into pGEX-3X, a suitable 5'-primer is 5'-T-C-G-T-G-G-G-A-T-C-C-C-C-G-G-G-A-A-T-T-C-A-A-T-G-T-C-T-G-A-A-T-T-T-G-A-A-T-T-A-C-T-G-3' (SEQ ID NO: 10). The first 22 bases of this primer are again derived from the pGEX-3X linker sequence, and the remainder correspond to nucleotides 208 to 229 of the coding strand for the methylase (S. Som et al. (1987), supra). A suitable 3'-primer is 5'-T-A-T-A-A-G-A-A-T-T-C-T-A-C-C-G-G-G-A-G-G-A-G-C-G-A-T-C-3' (SEQ ID NO: 11). The first 11 bases of this primer again include an EcoR I cleavage site, and the remainder of this primer corresponds to nucleotides 1656–1640 of the complementary non-coding strand. The DNA fragment to be amplified can be obtained from plasmids disclosed in S. Som et al. (1987), supra, carrying the cloned EcoR II gene, e.g., pSS18 or pSS19 (FIG. 1, p. 317), by cleavage with the endonucleases Pst I and BamH I, or other enzymes that cleave the plasmids to yield the fragment to be amplified.

For cloning the Hga I-1 methylase into pGEX-3X, a suitable 5'-primer is 5'-T-C-G-T-G-G-G-A-T-C-C-C-C-G-G-G-A-A-T-T-C-A-A-T-G-A-T-A-A-A-T-A-T-A-G-A-T-A-G-G-3' (SEQ ID NO: 12). The first 22 bases of this primer are again derived from the pGEX-3X linker sequence, and the remainder correspond to nucleotides 207 to 224 of the coding strand for the methylase (H. Sugisaki et al. (1991), supra). A suitable 3'-primer is 5'-T-A-T-A-A-G-C-A-T-G-C-C-A-T-T-G-C-A-T-T-A-A-T-T-T-T-G-3' (SEQ ID NO: 13). The first 11 bases of this primer include an Sph I cleavage site, and the remainder correspond to nucleotides 1311 to 1296 of the complementary non-coding strand. The DNA to be amplified can be obtained by cleavage of the clone pKS318 of Sugisaki et al. (1991), such as by Hind III.

For cloning the Hga I-2 methylase into pGEX-3X, a suitable 5'-primer is 5'-T-C-G-T-G-G-G-A-T-C-C-C-C-G-G-G-A-T-T-C-A-A-T-G-A-A-A-A-T-T-A-A-T-G-C-A-A-T-G-T-C-G-C-3' (SEQ ID NO: 14). The first 22 bases of this primer are gain derived from the pGEX-3X linker sequence, and the remainder correspond to nucleotides 1294 to 1315 of the coding strand for the methylase (H. Sugisaki et al. (1991), supra). A suitable 3'-primer is 5'-T-A-T-A-A-G-A-A-T-T-C-T-A-T-C-A-A-A-T-T-T-G-A-T-C-A-T-C-3' (SEQ ID NO: 15). The first 11 bases of this primer again include an EcoR I cleavage site, and the remainder of this primer corresponds to nucleotides 2387–2370 of the complementary non-coding strand. As Hga I-1 and Hga I-2 are read from partially overlapping, out-of-phase reading frames from the same sense strand, the DNA to be amplified can also be obtained by cleavage of the clone pKS318 of Sugisaki et al. (1991).

For cloning Hha I methylase into pGEX-3X, a suitable 5'-primer is 5'-T-C-G-T-G-G-G-A-T-C-C-C-C-G-G-G-A-A-T-T-C-A-A-T-G-A-T-T-G-A-A-A-T-A-A-A-A-G-A-T-A-A-A-C-A-G-C-3' (SEQ ID NO: 16). The first 22 bases of this primer are again derived from the pGEX-3X linker sequence, and the remainder correspond to nucleotides 437–461 of the coding sequence for Hha I methylase (M. Caserta et al. (1987), supra). A suitable 3'-primer is 5'-T-A-T-A-A-G-A-A-T-T-C-A-T-G-C-C-C-C-T-T-T-C-A-A-T-T-T-A-A-3' (SEQ ID NO: 17). The first 11 bases of this primer again include a EcoR I cleavage site, and the remainder correspond to nucleotides 1434–1417 of the complementary non-coding strand for Hha I. The fragment to be amplified can be isolated from clones including Hha I methylase, such as the clones pNW2801 and pRW959 of M. Caserta et al. (1987), supra, by cleavage with an appropriate endonuclease, such as Hind III (see FIG. 1 of M. Caserta et al. (1987), supra, p. 4772).

For cloning Hpa II methylase into pGEX-3X, a suitable 5'-primer is 5'-T-C-G-T-G-G-G-A-T-C-C-C-C-G-G-G-A-T-T-C-A-A-T-G-A-A-A-G-A-T-G-T-G-T-T-A-G-A-T-G-3' (SEQ ID NO: 18). The first 22 bases of this primer are again derived from the pGEX-3X linker, while the remainder correspond to residues 574–592 of the coding strand for Hpa II methylase (C. O. Card et al. (1990), supra). A suitable 3'-primer is 5'-T-A-T-A-A-G-A-A-T-T-C-A-A-G-G-C-T-C-A-C-T-C-C-A-C-T-C-T-C-C-T-C-3' (SEQ ID NO: 19). The first 11 bases of this primer include an EcoR I cleavage site, while the remainder correspond to nucleotides 1688–1668 of the non-coding strand for Hpa II methylase. Fragments containing Hpa II methylase DNA can be obtained from plasmids such as pCChpaIIM2-1 (C. O. Card et al. (1990), supra; see FIG. 1, p. 1379).

For cloning NgoP II methylase into pGEX-3X, a suitable 5'-primer has the sequence 5'-T-C-G-T-G-G-G-A-T-C-C-C-C-G-G-G-A-A-T-T-C-A-A-T-G-C-A-A-A-A-C-T-C-A-T-C-A-C-C-T-A-C-C-A-C-3' (SEQ ID NO: 20). The first 22 bases of this primer are derived from the pGEX-3X linker, while the remainder correspond to nucleotides 1857–1879 of the coding strand for NgoP II methylase (i.e., amino acids 1–8) (K. M. Sullivan & J. R. Saunders (1989), supra). The open reading frame for NgoP II methylase partially overlaps with the open reading frame for NgoP II restriction endonuclease, with the two being out of phase. A suitable 3'-primer has the sequence 5'-T-A-T-A-A-G-A-A-T-T-C-C-A-G-A-T-G-C-C-T-G-T-A-G-G-A-A-G-G-G-T-G-3' (SEQ ID NO: 21). The first 11 bases of this primer include an EcoR I cleavage site, while the remainder correspond to nucleotides 2905–2885 of the non-coding strand. Fragments containing DNA coding for NgoP II methylase can be obtained from clones such as pLV150 or pLV151 (K. M. Sullivan & J. R. Saunders (1989), supra), or from subclones, by cleavage with appropriate restriction endonucleases such as Hpa I and Pst I.

For cloning Nla III cytosine methylase, a suitable 5'-primer is 5'-T-C-G-T-G-G-G-A-T-C-C-C-C-G-G-G-A-A-T-T-C-A-A-T-G-A-A-T-T-A-T-A-T-C-G-G-C-T-C-C-A-A-A-C-3' (SEQ ID NO: 22). As described above, the first 22 bases of 5 this primer are derived from the pGEX-3X linker, while the remainder correspond to nucleotides 518–539 of the coding strand of the Nla III methylase (D. Labbe et al. (1990), supra). A suitable 3'-primer is 5'-T-A-T-A-A-G-A-A-T-T-C-C-C-A-A-G-T-A-T-T-C-G-T-A-C-A-G-3' (SEQ ID NO: 23). The 10 first 11 bases of this primer include an EcoR I site, while the remainder correspond to nucleotides 1597–1582 of the complementary, non-coding strand of the Nla III cytosine methylase. The DNA to be amplified can be derived from clones such as pUNL6 and other clones carrying Nla III cytosine methylase, such as by cleavage with EcoR I and Pst I restriction endonucleases (D. Labbe et al. (1990), supra).

For cloning of the methylase ScrF I into pGEX-3X, a suitable 5'-primer is 5'-T-C-G-T-G-G-G-A-T-C-C-C-C-G-G-G-A-A-T-T-C-A-A-T-G-C-T-A-A-G-A-G-T-A-T-T-G-A-A-G-C-3' (SEQ ID NO: 24). The first 22 bases of this primer are derived from the pGEX-3X linker, while the remainder correspond to nucleotides 186–205 of the coding strand for ScrF I methylase (D. P. Twomey et al. (1993), supra). A suitable 3'-primer is 5'-T-A-T-A-A-G-A-A-T-T-C-T-T-C-C-T-T-T-T-A-C-A-T-T-A-C-3' (SEQ ID NO: 25). The first 11 bases of this primer include an EcoR I site, and the remainder correspond to residues 1347–1327 of the complementary, non-coding strand of ScrF I methylase. The DNA to be amplified can be obtained from clones such as p1932m (D. P. Twomey et al. (1993), supra) by cleavage with restriction endonucleases such as EcoR I and Sau3A.

For cloning of the Sin I methylase into pGEX-3X, a suitable 5'-primer is 5'-T-C-G-T-G-G-G-A-T-C-C-C-C-G-G-G-A-A-T-T-C-A-A-T-G-A-T-A-A-T-G-A-A-T-G-A-C-A-T-C-A-T-T-A-C-C-G-3' (SEQ ID NO: 26). In this primer, the first 22 bases correspond to the pGEX-3X linker, while the remainder correspond to nucleotides 908–932 of the coding strand for the Sin I methylase (C. Karreman & A. de Waard (1988), supra). A suitable 3'-primer is 5'-T-A-T-A-A-G-C-A-T-G-C-A-A-T-G-G-A-A-G-G-G-G-G-A-T-T-C-C-C-3' (SEQ ID NO: 27). In this primer, the first 11 bases include an Sph I site, while the remainder correspond to nucleotides 2323–2306 of the complementary, non-coding strand of Sin I methylase (C. Karreman & A. de Waard (1988), supra). The DNA to be amplified can be obtained from clones such as pS14 by cleavage with the restriction endonucleases Pst I and Hind III, or from other subclones.

For cloning of the Sss I methylase into pGEX-3X, a suitable 5'-primer is 5'-T-C-G-T-G-G-G-A-T-C-C-C-C-G-G-G-A-A-T-T-C-A-A-T-G-A-G-C-A-A-A-G-T-A-G-A-A-A-A-T' (SEQ ID NO: 28). In this primer, the first 22 bases again correspond to the pGEX-3X linker, while the remainder correspond to the coding sequence for the first 6 amino acids of the Sss I methylase, nucleotides 104–121 in the coding strand (P. Renbaum et al. (1990), supra). A suitable 3'-primer is 5'-T-A-T-A-A-G-C-A-T-G-C-T-A-T-G-T-T-T-T-A-T-T-G-A-C-A-T-G-T-3' (SEQ ID NO: 29). In this primer, the first 11 bases include an Sph I cleavage site, while the remainder correspond to nucleotides 1282–1275 of the complementary, non-coding strand of the Sss I methylase. The DNA to be amplified can be obtained from clones such as pMT1, pMT21, or pMT7 by cleavage with appropriate restriction endonucleases (P. Renbaum et al. (1990), supra; see p. 1147, FIG. 4).

For cloning of the Sso II methylase into pGEX-3X, a suitable 5'-primer is 5'-T-C-G-T-G-G-G-A-T-C-C-C-C-G-G-G-A-A-T-T-C-A-A-T-G-A-T-A-A-T-G-A-C-T-G-A-T-A-A-T-A-T-C-G-C-A-G-C-A-A-C-A (SEQ ID NO: 30). In this primer, the first 22 bases are derived from the pGEX-3X linker, while the remainder correspond to amino acids 1–8 of the methylase (residues 1301–1277 of the complementary strand, the coding strand in this instance). (A. S. Karyagina et al. (1993), supra). For *Shigella sonnei*, the Sso II methylase and Sso II restriction endonuclease are read from the opposite strands. A suitable 3'-primer is 5'-T-A-T-A-A-G-A-A-T-T-C-G-C-G-G-T-G-T-T-C-G-C-G-G-C-A-G-A-A-T-C-3' (SEQ ID NO: 31). In this primer, the first 11 bases include an EcoR I cleavage site, while the remainder correspond to nucleotides 42–62 of the non-coding strand for Sso methylase. The DNA to be amplified can be obtained from clones described in A. S. Karyagina et al. (1993), supra, or in A. S. Karyagina et al., "Characterization of the Genetic Determinants of SsoII-Restriction Endonuclease and Modification Methyltransferase," *Gene* 87: 113–118 (1990).

For Nae I methylase, a suitable 5'-primer has the sequence 5'-T-C-G-T-G-G-G-A-T-C-C-C-C-G-G-G-A-A-T-T-C-A-A-T-G-C-A-G-A-G-T-C-T-C-G-A-G-G-T-A-G-T-G-G-A-G-3' (SEQ ID NO: 32). The first 22 nucleotides of this primer correspond to the pGEX-3X linker, while the remainder correspond to the nucleotide sequence of the coding strand encoding the first 8 amino acids of the Nae I methylase. A suitable 3'-primer is 5'-T-A-T-A-A-G-A-A-T-T-C-G-C-C-T-A-T-T-G-G-A-C-A-T-C-C-A-G-3' (SEQ ID NO: 33). The first 11 bases of this primer include an EcoR I site, while the remainder correspond to nucleotides 9–26 downstream of the T-A-G stop codon for the Nae I methylase gene. The DNA to be amplified can be obtained from clones such as those described in E. M. Van Cott & G. G. Wilson (1988), supra.

Other primers than those recited above can also be used. In particular, primers with a limited degree of mismatching can be used to carry out mutagenesis. Additionally, longer or shorter primers can be used in most cases. Moreover, for the 3'-primers, a different portion of the non-coding strand that is past the stop codon for the methylase whose gene is being amplified can be used.

Alternatively, other plasmids can be substituted for pGEX-3X in the construction of the plasmid of the present invention. An alternative plasmid is the similar plasmid pGEX-2T (Pharmacia Biotech), which also incorporates the gene *S. japonicum* glutathione transferase, but in which the fusion product can be cleaved by the proteolytic enzyme thrombin.

In addition, a technique known as splice-overlap extension (SOE) can be used to join any polypeptide determinant open reading frame (ORF) to any methylase (C-5) ORF or DNA binder ORF. This technique is described in R. M. Horton et al., "Gene Splicing by Overlap Extension: Tailor-Made Genes Using the Polymerase Chain Reaction," *BioTechniques* 8: 528–534 (1990); S. N. Ho et al., "DNA and Protein Engineering Using the Polymerase Chain Reaction," *DNA & Prot. Engineer. Tech*. 2: 50–55 (1990); S. N. Ho et al., "Site-Directed Mutagenesis by Overlap Extension Using the Polymerase Chain Reaction," *Gene* 77: 51–59 (1989); R. M. Horton et al,. "Engineering Hybrid Genes Without the Use of Restriction Enzymes: Gene Splicing by Overlap Extension," *Gene* 77: 61–68 (1989); and J. Yon & M. Fried, "Precise Gene Fusion by PCR," *Nucl. Acids Res*. 17: 4895 (1989).

Figure 8A:
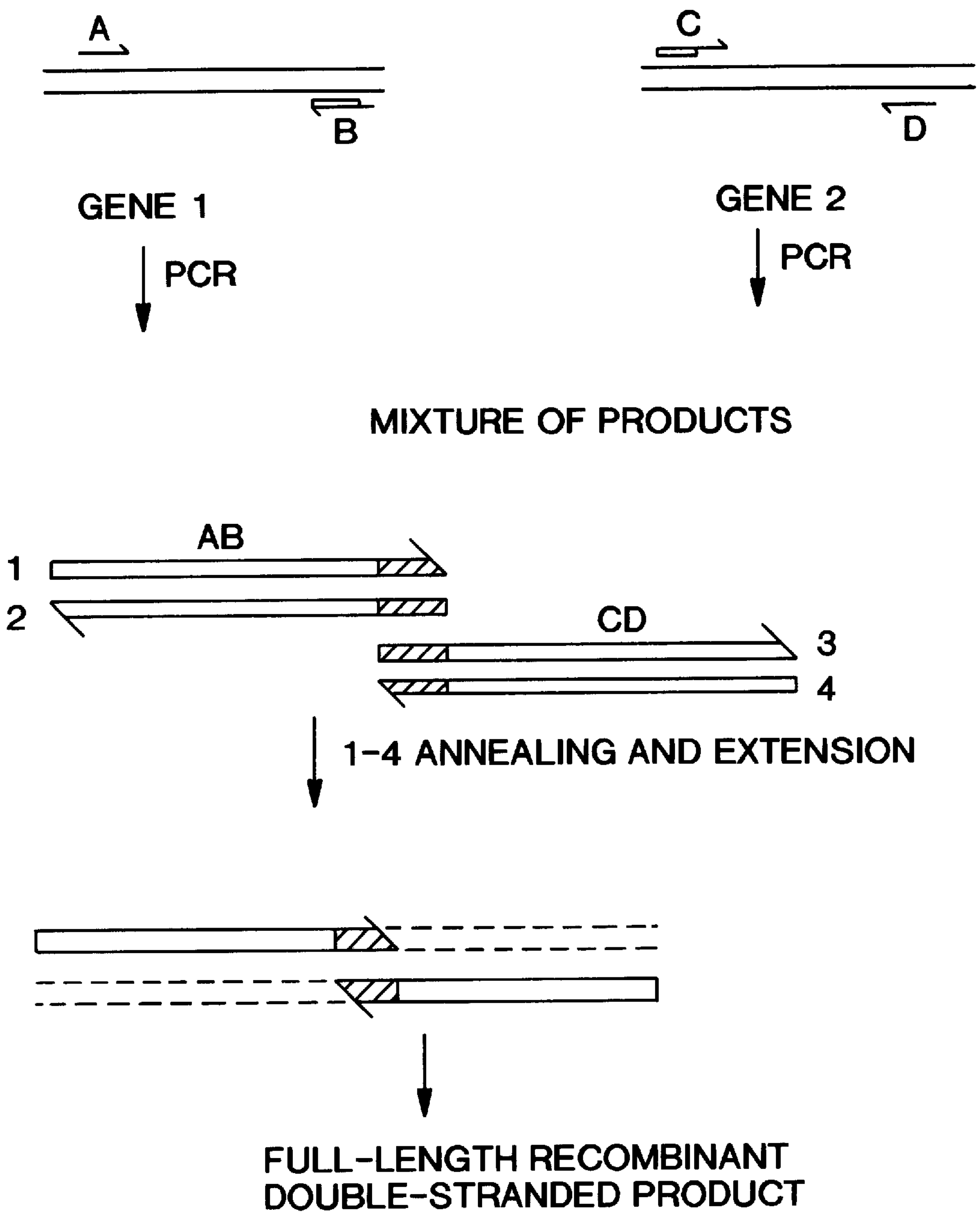
FIG. 8A is a schematic diagram of the splice-verlap extension technique.
Figures 1, 8B:
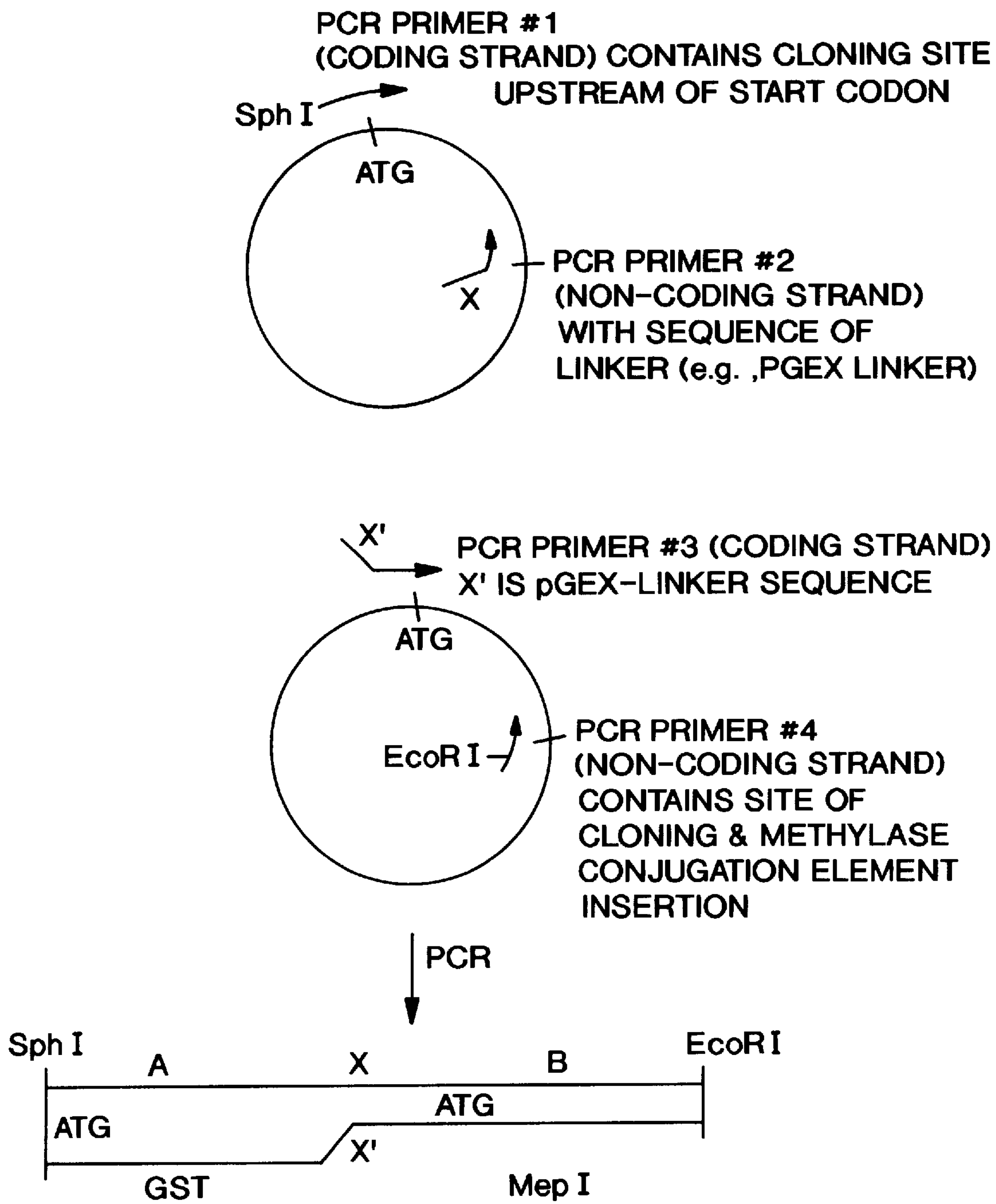
Figures 2, 8B:
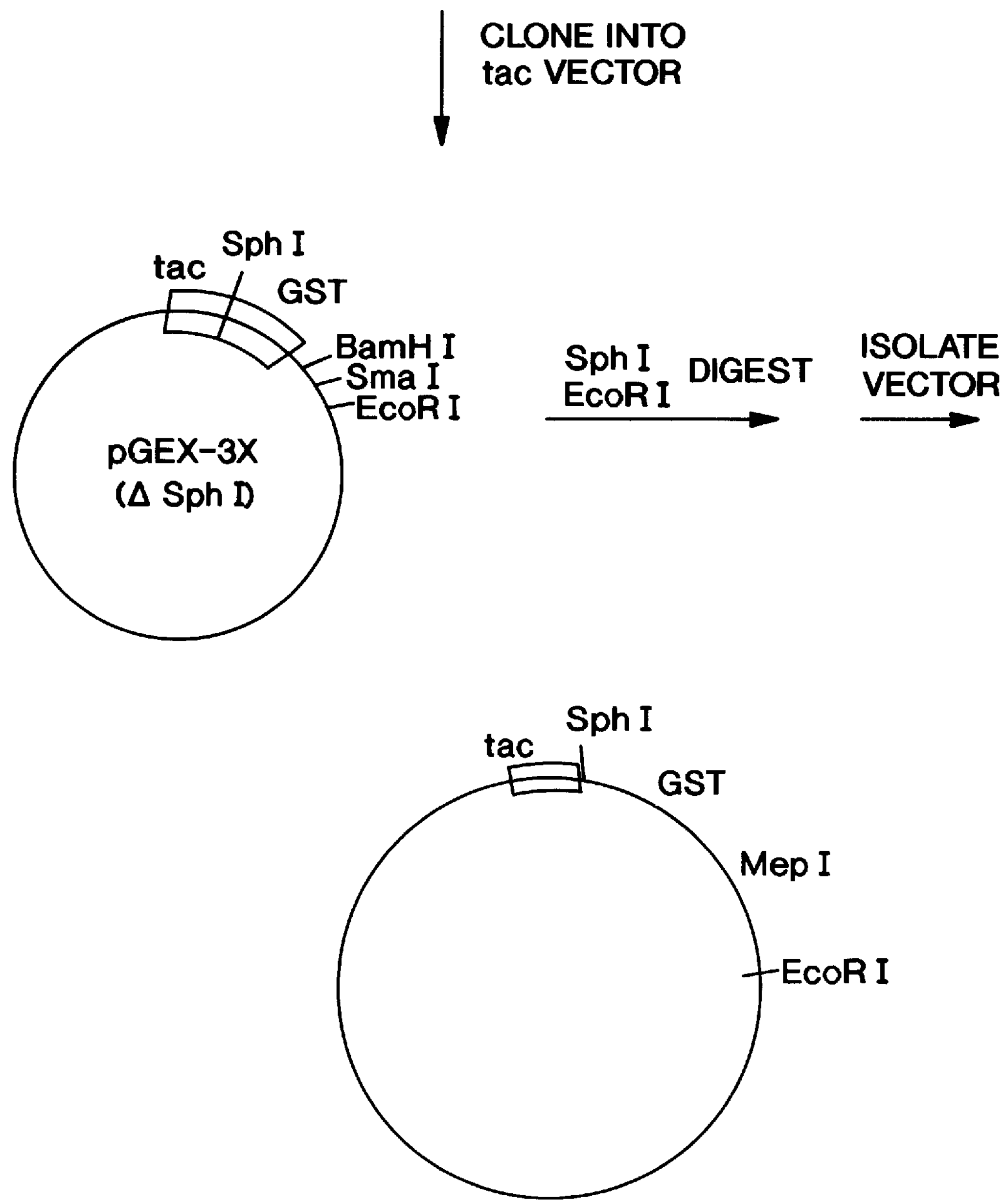

In general, this method is carried out as shown in FIGS. 8A and 8B-1 and 8B-2. FIG. 8A shows the general procedure for SOE; FIG. 8B shows SOE as applied to the preparation of gene fusions between polypeptide determinants and methylases. It is assumed that the two ORFs are cloned into separate plasmids. The ORF of the polypeptide determinant is represented by A, and the ORF of the methylase, such as Msp I methylase, is represented by B. Four PCR primers are required, to be used in two separate PCR reactions. For the first PCR reaction, primer 1 corresponds to the coding strand of the ORF of the polypeptide determinant, and contains a cloning site upstream of the start codon. Primer 2 corresponds to the non-coding sequence at the C-terminal end of the ORF of the polypeptide determinant, and includes a 5'-linker, such as a pGEX-3X linker, that is not base-paired (X).

For the second PCR reaction, primer 3 corresponds to the coding strand of the ORF of the methylase and contains a non-base-paired 5'-linker (X'), such as a pGEX-3X linker. Primer 4 corresponds to the non-coding strand of the ORF of the methylase and contains a site for cloning and methylase conjugation element insertion.

The combination and extension of the products of the PCR reaction yields a fusion product with the polypeptide determinant, such as glutathione S-transferase, fused to the methylase, such as Msp I methylase, through the hybridized linker sequences. The primers are designed to remove the termination codon of the polypeptide determinant so that the polypeptide determinant and the methylase are translated as one fusion protein, with the AUG codon of the methylase being translated simply as methionine and not initiating another polypeptide chain. The fusion product is cloned into pGEX-3X (Δ Sph I) that has been digested with Sph I and Eco RI to remove the glutathione transferase present in the vector while retaining the tac promoter (FIG. 8B).

Similar techniques can be used to prepare vectors including fusion proteins between genes other than glutathione S-transferase and the methylase. This process typically begins with cloning the fusion partner for the methylase into pNRT2, replacing the glutathione S-transferase. It may, again, in some cases be necessary to delete or add bases at the points where the fusion partner and the methylase begin to maintain the proper reading frame.

The above procedures describe processes for producing plasmids in which the polypeptide determinant is fused to the methylase so that the amino-terminus of the methylase is linked to the carboxyl-terminus of the polypeptide determinant (i.e., the linking orientation is the first linking orientation as described above). It is also possible to prepare plasmids according to the present invention in which the polypeptide determinant is fused to the methylase so that the carboxyl-terminus of the methylase is linked to the amino-terminus of the polypeptide determinant (i.e., the linking orientation is the second linking orientation as described above).

A method for preparing a C-terminal fusion between a methylase such as Msp I and a polypeptide determinant such as glutathione S-transferase, in which the glutathione S-transferase and methylase are expressed as a single fusion protein with the glutathione S-transferase at the amino-terminus and the methylase at the carboxyl terminus, can be as follows: First, the plasmid pGEX-3X is converted to pNRT2 as described above and by C. Taylor et al., "Determination of the Order of Substrate Addition to Msp I DNA Methyltransferase Using a Novel Mechanism-Based Inhibitor," *Biochem. J.* 291:493–504 (1993). Msp I methylase is active as both an N-terminal and a C-terminal fusion product with glutathione S-transferase.

Site-directed mutagenesis using the phosphorothioate method and materials provided by Amersham (Arlington Heights, Ill.) is used to introduce two Sph I restriction sites. The first Sph I site is in the tac promoter and the second is in the pGEX-3X linker region. The sequences and primers used are shown below:

The wild-type tac promoter and formyl-methionine initiator codon of glutathione S-transferase and the next four codons of the enzyme is: 5'-C-A-C-A-G-G-A-A-A-C-A-G-T-A-T-T-C-A-T-G-T-C-C-C-C-T-A-T-A-C-3' (SEQ ID NO: 34). The site-directed mutagenesis primer sequence is 5'-C-A-C-A-G-G-A-A-A-C-A-G-C-A-T-G-C-A-T-G-T-C-C-C-C-T-A-T-A-C-3'(SEQ ID NO: 35). The two mutant nucleotides are underlined. This site-directed mutagenesis primer will generate a Sph I site one nucleotide downstream of the GST N-formyl-methionine$_1$ codon. The primer spans nucleotides 241 to 270 in the pGEX-3X sequence; the N-formyl-methionine codon (ATG) of glutathione S-transferase is at nucleotide 258.

Figure 9:
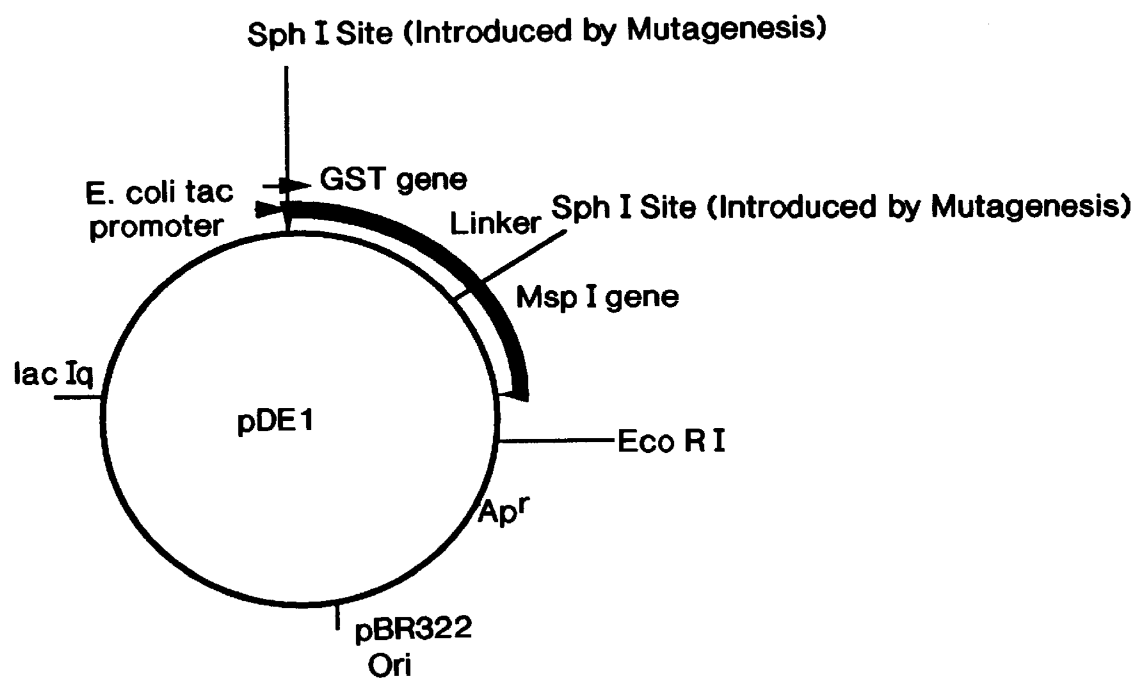
FIG. 9 is a schematic diagram of plasmid pDE1.

To introduce the second Sph I site, a mutagenic primer is used to introduce a second Sph I site one nucleotide upstream of the first codon in the Msp I methylase. The wild-type pNRT2 linker sequence is: 5'-G-G-T-C-G-T-G-G-G-A-T-C-G-A-T-C-C-C-C-C-C-C-A-T-G-C-A-A-C-C-T-G-A-3' (SEQ ID NO: 36). The mutagenic primer has the sequence 5'-G-G-T-C-G-T-G-G-G-A-T-C-G-A-T-G-C-A-T-G-C-A-T-G-C-A-A-C-C-T-G-A-3' (SEQ ID NO: 37). The mutations introduced are underlined. Use of this mutagenic primer introduces an in-frame Sph I site one nucleotide upstream of the first codon in Msp I, to yield the plasmid pDE1 shown in FIG. 9.

Digestion of pDE1 with the enzyme Sph I yields a cleaved plasmid with the glutathione S-transferase gene removed. Religation will yield the Msp I methylase in-frame and at the same distance from the tac ribosome binding site as the original glutathione S-transferase construct.

In general, it is preferred that the two site-directed mutagenesis steps are performed sequentially and that plasmids are isolated at each step to show the correct incorporation of the Sph I cleavage sites.

In the next step, the Msp I methylase gene is excised and its 3'-end is now modified to contain the linker sequence used in pNRT2. This is accomplished by a PCR reaction on the plasmid with two primers: a 5'-PCR primer corresponding to the coding strand, and a 3'-PCR primer corresponding to the non-coding strand.

The 5'-PCR primer is: 5'-C-A-C-A-G-G-A-A-A-C-A-G-C-A-T-G-C-A-T-G-C-A-A-C-C-T-G-3' (SEQ ID NO: 38). This primer includes the start of the coding sequence of Msp I methylase, beginning with ATG. The 3'-PCR primer is 5'-T-G-A-A-T-T-C-C-C-G-G-G-G-A-T-C-C-C-A-C-G-A-C-C-T-T-C-G-A-T-A-A-C-G-A-G-T-T-C-T-A-A-T-T-C-A-A-A-C-A-A-A-A-G-3' (SEQ ID NO: 39). The first 30 bases of this primer correspond to a linker sequence including EcoR I, Sma I, and BamH I restriction endonuclease sites, while the remainder correspond to non-coding sequences for the 3'-end of the Msp I methylase gene, namely E-N-F-E-L-E-L-V (SEQ ID NO: 40). The results of carrying out PCR on these primers is shown in FIG. 10. This results in a Msp I methylase gene with a SpH restriction endonuclease site fused to its amino-terminus, and a linker including the BamH I, Sma I, and EcoR I sites fused to the carboxy-terminal end of the gene. The construct also includes a factor X protease cleavage site near the carboxy-terminus of the Msp I methylase gene.

The PCR product is digested with the restriction endonucleases Sph I and EcoR I. The digested PCR product is cloned into the Sph I/EcoR I-digested pDE1 plasmid. The resulting construct is then ligated to yield pDE3. This step is shown in FIG. 11.

The plasmid pDE2 has the pGEX-3X linker fused to the 3'-end of the Msp methylase gene so that expression is driven by the *E. coli* tac promoter. The gene fusion product with Msp I methylase fused to the 5'-end of GST (Msp I-GST) is active.

In the next step, a glutathione S-transferase gene is generated so that it can be attached to the carboxy-terminus (3'-end) of the Msp I methylase, which is the reverse order than the order seen when the methylase is directly cloned into pGEX-3X. This is shown schematically in FIG. 12. The 5'-PCR primer is 5'-C-A-C-A-G-G-A-A-A-C-A-G-G-A-T-C-C-C-C-A-T-G-T-C-C-C-C-T-A-T-A-C-T-A-G-3' (SEQ ID NO: 41). This primer contains a tac promoter near its 5'-end. The underlined bases introduce a mutation that contains a BamH I site; the two C's adjacent to the underlined bases are required to keep the 5'-end of the glutathione S-transferase in the proper reading frame.

The 3'-primer has the sequence 5'-T-C-A-C-G-A-G-G-A-T-C-C-T-C-A-T-C-A-A-T-C-C-G-A-T-T-T-T-G-G-A-G-G-A-T-G-G-A-C-G-3' (SEQ ID NO: 42). This primer contains the non-coding strand for the 3'-end of glutathione S-transferase, a stop codon, sites for Sma I, Eco I, and BamH I restriction endonucleases, and another stop codon.

The resulting PCR product is then digested with BamH I restriction endonuclease and ligated into BamH I-digested pDE3 to yield the construct in which the glutathione S-transferase gene is attached to the C-terminus of the Msp I methylase. This construct is designated PREV herein. The Msp I-GST fusion protein is active.

This method can be used for other polypeptide determinants and other methylases or DNA binding proteins with the appropriate PCR primers. In particular, the primers for step (4) must be modified to include the proper nucleotides for the polypeptide determinant to be cloned, in this example, glutathione S-transferase. The primers in step (1) also must be modified appropriately to generate the Sph I site one nucleotide downstream of the fMet codon that initiates translation of the polypeptide determinant.

Similarly, the primers in steps (2) and (3) must be modified so that the sequence of the DNA binder or methylase other than Msp I methylase is matched appropriately.

In some cases, further adjustments must be made to maintain the proper reading frame, as was done in this example in step (4). These adjustments would be obvious to one of ordinary skill in the art, and it is routine to use primers with a degree of mismatching.

The following methods are used to generate and introduce methylase conjugation elements into vectors containing the gene fusion constructs. These methods are described for EcoR I, Hga I-1, Hga I-2, Hha I, Msp I and its isoschizomer Hpa II, NgoP II, and Nae I. Analogous methods can be used to synthesize and introduce methylase conjugation elements for other methylases or DNA binders, depending on the sequence recognized by the methylase or DNA binder.

For EcoR II, a palindromic sequence is used. This sequence is 5'-A-A-T-T-C-C-A-G-G-A-T-C-C-A-G-G-A-C-C-A-T-G-G-T-C-C-T-G-G-A-T-G-C-A-G-G-3' (SEQ ID NO: 43). This oligomer, which contains four copies of the methylase conjugation element for EcoR II, is cloned into the EcoR I site of the plasmid pNRT2 to generate the methylase conjugation element. Because the sequence is palindromic, only a single strand need be synthesized. Typically, synthesis occurs by solid-phase oligonucleotide synthesis according to well-known reaction schemes, such as the phosphodiester, phosphotriester, or H-phosphonate solid phase oligonucleotide synthesis procedures. The single strand is synthesized and purified from a 6% polyacrylamide gel (J. Sambrook et al., "Molecular Cloning: A Laboratory Manual" (Cold Spring Harbor Laboratory Press, Cold Spring Harbor, N.Y., 1989, 2d ed.), vol. 2, pp. 6.36–6.48. The isolated single-stranded DNA is then annealed by heating to 100° C. for 2 minutes in 50 mM NaCl, 50 mM NaCl, 50 mM Tris-HCl, pH 7.0, and cooled in a water bath slowly to room temperature (22° C.). The duplex thus formed is then ligated into dephosphorylated EcoR I-digested vector. The insertion of the oligomer into the vector is shown in FIG. 13; the lines at the left and the right indicate the EcoR I site and divide residues that are part of the vector from residues that are part of the methylase conjugation element.

Figure 13:
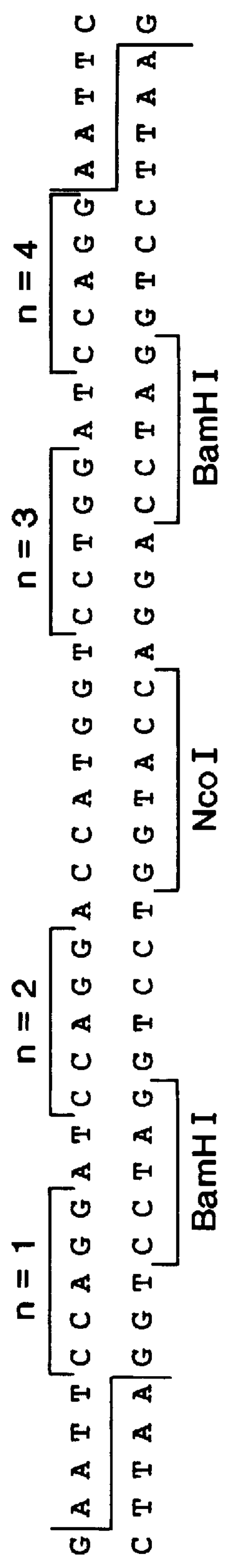
FIG. 13 is a schematic diagram of the insertion of a methylase conjugation element for EcoR II methylase into a vector (SEQ ID NO:61)

The resulting methylase conjugation element contains four EcoR II sites, two EcoR I sites regenerated at the ends of the oligomer, two BamH I sites, and one Nco I site, shown in FIG. 13.

Figure 14:
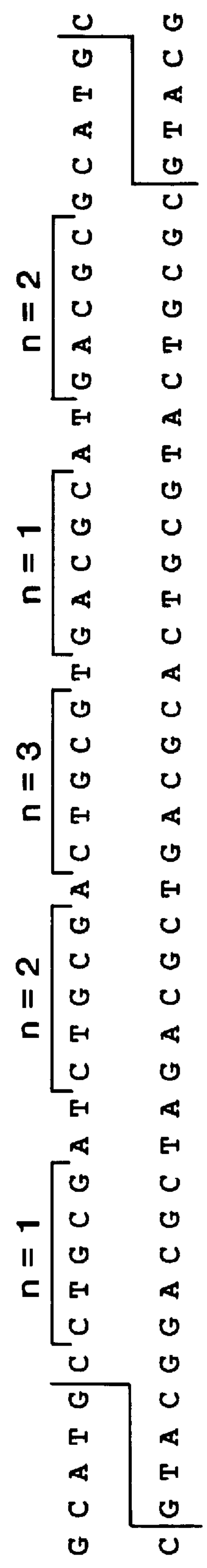
FIG. 14 is a schematic diagram of the insertion of a methylase conjugation element for Hga I-1 and Hga I-2 methylases into a vector (SEQ ID NO:62)

For a methylase conjugation element for the enzymes Hga I-I and Hga I-II, a similar procedure can be followed except that two separate strands are required rather than a palindromic single strand. The two strands are: 5'-C-C-T-G-C-G-A-T-C-T-G-C-G-A-C-T-G-C-G-T-G-A-C-G-C-A-T-G-A-C-G-C-G-C-A-T-G-3' (SEQ ID NO: 44). The second strand is 5'-C-G-C-G-T-C-A-T-G-C-G-T-C-A-C-G-C-A-G-T-C-G-C-A-G-A-T-C-G-C-A-G-G-C-A-T-G-3' (SEQ ID NO: 45). Each of the single-stranded oligonucleotides synthesized is 36 nucleotides. Both strands are synthesized separately, purified as described above, and annealed at a 1:1 ratio as determined by $A_{260nm}$. The duplex is then ligated into EcoR I-digested vector. The combination of the vector and the hybridized oligomers is shown in FIG. 14; the lines at the left and the right indicate the EcoR I site and divide residues that are part of the vector from residues that are part of the methylase conjugation element. This construct includes three Hga I-1 sites and two Hga I-2 sites, with the Hga I-1 sites being located at the left side of the oligomer and the Hga I-2 sites being located at the right-hand side of the oligomer.

Similar procedures can be used to introduce a methylase conjugation element for Hha I methylase. This also requires two separately synthesized single-stranded oligonucleotides: The first of these has the sequence 5'-A-A-T-T-C-A-G-C-G-C-T-G-C-G-C-A-G-C-G-C-T-G-C-G-C-A-G-C-G-C-T-G-C-G-C-G-3' (SEQ ID NO: 46). The second of these sequences is 5'-A-A-T-T-C-G-C-G-C-A-G-C-G-C-T-G-C-G-C-A-G-C-G-C-T-G-C-G-C-A-G-C-G-C-T-G-3' (SEQ ID NO: 47). The two sequences are synthesized separately and annealed, and ligated into an EcoR I-digested vector as described for Hga I-1 and Hga I-2. The resulting arrangement is shown in FIG. 15; the lines at the left and the right indicate the EcoR I site and divide residues that are part of the vector from residues that are part of the methylase conjugation element. The sequence contains six copies of the Hha I methylase recognition site.

For the isoschizomers Hpa II and Msp I, a palindromic sequence can be used and, therefore, synthesis of only one strand is required. The sequence synthesized can be: 5'-A-A-T-T-C-A-T-C-C-G-G-A-C-C-G-G-T-C-C-G-G-A-T-C-C-G-G-A-T-G-3' (SEQ ID NO: 48). This sequence is annealed and inserted as described for EcoR II, as in Example 2, below; see FIG. 16. The sequence contains six Hpa II or Msp I methylase binding sites and two BamH I sites.

Figure 17:
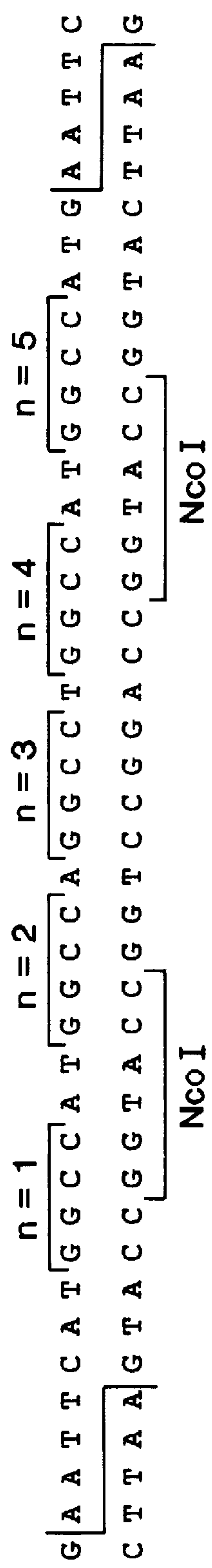
FIG. 17 is a schematic diagram of the insertion of a methylase conjugation element for the isoschizomeric NgoP or Hae III methylases into a vector (SEQ ID NO:65)

A similar procedure can be used to generate methylase conjugation elements specific for the methylases NgoP II or Hae III, which are also isoschizomers. A single palindromic sequence can be used. This sequence is 5'-A-A-T-T-C-A-T-G-G-C-C-A-T-G-G-C-C-A-G-G-C-C-T-G-G-C-C-A-T-G-G-C-C-A-T-G-3' (SEQ ID NO: 49). The resulting palindromic single-stranded sequence is synthesized, annealed, and cloned into the vector as described above for EcoR II. The resulting arrangement is shown in FIG. 17; the lines at the left and the right indicate the EcoR I site and divide residues that are part of the vector from residues that are part of the methylase conjugation element. The methylase conjugation element has five NgoP II or Hae III sites as well as two Nco I sites.

A similar arrangement can also be used for Nae I, for which a palindromic single oligonucleotide can be used. The oligonucleotide has the sequence 5'-A-A-T-T-C-G-C-C-G-G-C-A-T-G-C-C-G-G-C-T-A-G-C-C-G-G-C-A-T-G-C-C-G-G-C-G-3' (SEQ ID NO: 50).

Figure 18:
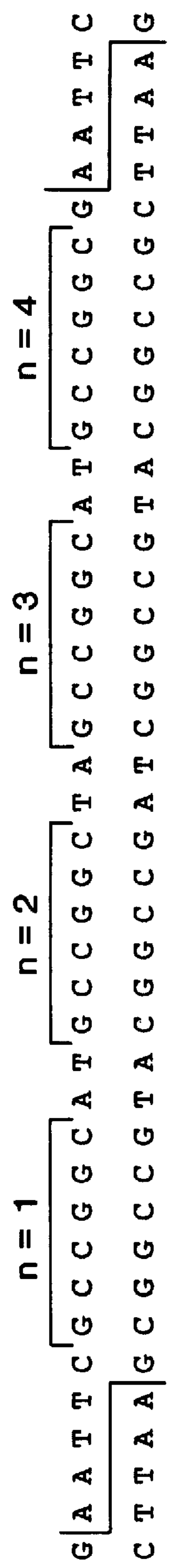
FIG. 18 is a schematic diagram of the insertion of a methylase conjugation element for Nae I methylase into a vector (SEQ ID NO:66)

The sequence is synthesized, annealed, and cloned as for EcoR I. The arrangement in the vector is shown in FIG. 18; the lines at the left and the right indicate the EcoR I site and divide residues that are part of the vector from residues that are part of the methylase conjugation element. The sequence contains four Nae I methylase recognition sites.

III. PLASMID-POLYPEPTIDE DETERMINANT CONJUGATES

Another aspect of the present invention is a plasmid-polypeptide determinant conjugate. In general, the plasmid-polypeptide determinant conjugate of the present invention comprises a plasmid and a gene fusion product covalently conjugated to the plasmid via a pyrimidine moiety of a cytidine suicide analogue, the plasmid including:

(1) a gene fusion construct including a DNA methylase gene and a polypeptide determinant gene covalently joined thereto, the gene fusion construct encoding a gene fusion product including a cytosine (C-5) DNA methylase having a methyltransferase activity and a polypeptide determinant covalently joined thereto;

(2) a promoter operatively linked to the gene fusion construct for promoting transcription of the gene fusion construct as messenger RNA; and (3) a methylase conjugation element linked to the gene fusion construct, the methylase conjugation element including a methylase binding site having a nucleotide sequence including a cytidine suicide analogue capable of irreversibly binding the cytosine (C-5) DNA methylase of the gene fusion product and having a methylation specificity for the cytosine (C-5) DNA methylase.

Alternatively, if the framework regions of the plasmid, as defined above, contain at least one methylase binding site that contains a cytidine suicide analog, the plasmid need not contain a methylase conjugation element. In this alternative, conjugation of the plasmid to the gene fusion product occurs by covalent linkage of the gene fusion product to the cytidine suicide analog in the framework region, and a separate methylase conjugation element is not necessary. For example, in the plasmid pGSX-3X there are 19 Msp I (or Hpa II) binding sites at nucleotides 1038, 1072, 1627, 1869, 1979, 2046, 2080, 2484, 2674, 2700, 2847, 3288, 3355, 3747, 3988, 4096, 4465, 4715, and 4733. These sites can be used to covalently link the plasmid to the gene fusion product by incorporating a cytidine suicide analog in one or more sites.

In the plasmid-polypeptide determinant, because of the existence of the gene fusion product, the polypeptide determinant is covalently linked to the nucleic acid encoding it via the gene fusion construct and the DNA methylase. This allows association of genetic information with proteins encoded by the genetic information. This association is stable as the result of covalent binding.

IV. LIBRARIES OF PLASMID-POLYPEPTIDE DETERMINANT CONJUGATES

Another aspect of the present invention is libraries of plasmid-polypeptide determinant conjugates. In general, such libraries comprise a plurality of plasmid-polypeptide determinant conjugates, each plasmid-polypeptide determinant conjugate including a plasmid and a gene fusion product covalently conjugated to the plasmid via a pyrimidine moiety of a cytidine suicide analogue, the plasmid including a gene fusion construct, promoter, and methylase conjugation element as described above.

One important type of library according to the present invention is a library that contains polypeptide determinants generated from an initial wild-type polypeptide determinant as the result of mutagenesis. Typically, this mutagenesis is random mutagenesis by mutagenic agents such as nitrous acid or methyl-N'-nitro-N-nitrosoguanidine. Other mutagens can also be used. Alternatively, directed or partially directed localized mutagenesis techniques can be used such as oligonucleotide-directed mutagenesis with a mixture of oligonucleotides, mutagenesis involving linkers, or randomly mutagenized oligonucleotide synthesis by in vitro synthesis of a single-stranded oligonucleotide, with random substitutions. These mutagenesis techniques are described, for example, in B. Perbal, "A Practical Guide to Molecular Cloning" (2d ed., John Wiley & Sons, 1988), ch. 23, pp. 685–718, and in J. Sambrook et al., "Molecular Cloning: A Laboratory Manual" (2d ed., Cold Spring Harbor Laboratory Press, Cold Spring Harbor, N.Y., 1989), ch. 15, pp. 15.1–15.113. Other mutagenesis techniques are also known in the art and can be used.

One particularly preferred mutagenic technique involves the use of the polymerase chain reaction (PCR) process. PCR amplification methods are described in detail in U.S. Pat. Nos. 4,683,195, 4,683,202, 4,800,159, and 4,965,188, all of which are incorporated herein by reference.

In the use of PCR for mutagenesis, the PCR process is used not only to produce a library of DNA molecules, but also to induce mutations within the library or to create diversity from a single parental clone and thereby provide a library having greater heterogeneity. First, it should be noted that the PCR process itself can be inherently mutagenic due to a variety of factors well known in the art. Second, in addition to the mutation-inducing variations described in U.S. Pat. No. 4,683,195, other mutation-inducing PCR variations can be employed. For example, the PCR reaction mixture can be formed with different amounts of one or more of the nucleotides to be incorporated into the extension product. Under such conditions, the PCR reaction proceeds to produce nucleotide substitutions within the extension product as a result of the scarcity of a particular base in the reaction mixture. Similarly, approximately equal molar amounts of the nucleotides can be incorporated into the initial PCR reaction mixture in an amount sufficient for efficient performance of X number of reaction cycles, and then an increased number of reaction cycles, for instance, 2X, can be performed, causing nucleotide substitutions as the result of scarcity of the required base in the later cycles. Alternatively, mutations can be induced during the PCR reaction by incorporating into the reaction mixture nucleotide derivatives such as inosine, not normally found in the nucleic acids of the repertoire being amplified. During subsequent in viva DNA synthesis and replication of the nucleic acids in a host cell, the nucleotide derivative will then be replaced with a substitute nucleotide, thereby inducing a point mutation.

Among the expression vectors that can be used for producing libraries of mutagenized DNA molecules are linearized DNA molecules having two (upstream and downstream) cohesive termini adapted for directional ligation to a gene for a polypeptide determinant.

A linear DNA expression vector is typically prepared by restriction endonuclease digestion of a circular DNA expression vector to cut at two preselected restriction sites within the sequence of nucleotides of the vector adapted for directional ligation to produce a linear DNA molecule having the required cohesive termini that are adapted for directional ligation. Directional ligation refers to the presence of two (a first and second) cohesive termini on a vector, or on the insert DNA molecule to be ligated into the vector selected, so that the termini on a single molecule are not complementary. A first terminus of the vector is complementary to a first terminus of the insert, and the second terminus of the vector is complementary to the second terminus of the insert. This ensures that the insert can be inserted into the vector in only one orientation.

In preparing a library of DNA molecules, such as a library to be subjected to PCR mutagenesis or other mutagenic procedures, a ligation reaction mixture is prepared, and the reaction mixture is subjected to ligation conditions for a time period sufficient for the repertoire of polypeptide determinant genes to ligate (become operatively linked) to the plurality of DNA expression vectors to form the library.

Ligation conditions are conditions selected to favor a ligation reaction wherein a phosphodiester bond is formed between adjacent 3'-hydroxyl and 5'-phosphoryl termini of DNA. The ligation reaction is preferably catalyzed by the enzyme T4 DNA ligase, although other ligases are known, such as *E. coli* ligase. Ligation conditions can vary in time, temperature, concentration of buffers, quantities of DNA molecules ligated, and other variables. Ligated molecules can be resolved from unligated molecules by agarose gel electrophoresis or other methods.

One particularly preferred vector useful for increasing the diversity of a population through mutagenesis is the filamentous phage, such as those disclosed in J. Sambrook et al., "Molecular Cloning: A Laboratory Manual," supra, vol. 1, pp. 4.1–4.54. One particularly useful filamentous phage vector is M13; other useful vectors are derived from M13.

One particularly useful method of mutagenesis employs single-stranded DNA, prepared from filamentous phage, as a template for primer-directed, PCR, or phosphorothioate mutagenesis reactions.

After subjecting single-stranded DNA, derived from a phage vector incorporating the polypeptide determinant gene, to random mutagenesis, a library of polypeptide determinant genes is obtained. The library of polypeptide determinant genes can remain within the genome of the filamentous phage into which they have been cloned. Alternatively, the library of polypeptide determinant genes can be cloned out of the phage host, isolated en masse, and cloned into an appropriate selection plasmid.

One particularly preferred expression-selection plasmid is pDE1. An alternative expression-selection plasmid is pDE2. Another alternative expression-selection plasmid is pNRT2 from which the GST gene has been deleted. Cloning a library of polypeptide determinant genes into the expression-selection vector pDE1 would generate a library of plasmids in which the expression of mutant polypeptide determinant genes is driven by the *E. coli* tac promoter fused to the 5'-end of the mutant polypeptide determinant gene. The 3'-end of the polypeptide determinant gene is covalently joined either directly or through a linker to a gene encoding a DNA methylase. It is obvious to one skilled in the art that in vivo expression of the gene fusion product from the gene fusion construct contained in the expression-selection plasmids of such a library of plasmids would yield a corresponding library of gene fusion products.

A particularly preferred polypeptide determinant gene is the glutathione-S-transferase gene from *S. japonicum*. A particularly preferred region for random mutagenesis is the GST active site. Particularly preferred residues within the GST active site for mutation are the first residues in the amino-terminal region. Of particular relevance are residues Tyr7 and Trp8 (X. Ji et al., "Structure and Function of the Xenobiotic Substrate Binding Site of a Glutathione S-Transferase as Revealed by X-Ray Crystallographic Analysis of Product Complexes with the Diastereomers of 9-(S-Glutathionyl)-10-Hydroxy-9,10-Dihydrophenanthrene," *Biochemistry* 33: 1043–1052 (1994)).

A particularly preferred DNA methylase gene is the gene for Msp I methylase.

Oligonucleotide primers that may be used in error-prone PCR reactions to generate random mutations in the GST gene can be primers 1, 2, 3, and 4 (SEQ ID NO: 51, 52, 53, & 54), respectively, or any of the GST specific primers disclosed herein. The use of these primers or other primers is obvious to one skilled in the art.

Mutagenesis methods according to the present invention provide methods for changing the diversity of a library as described above, such as a library of filamentous phage. These methods generally increase the diversity of the library, thereby increasing the pool of possible receptor-binding or other specific binding pair-member binding complexes from which to screen for a desired binding activity. Alternatively, the methods can be directed at enriching for a class of hapten-, substrate-, inhibitor-, or epitope-binding complexes. The class is typically defined by the ability to bind a particular hapten, substrate, inhibitor, or epitope or family of haptens, substrates, inhibitors, or epitopes.

A particularly preferred method for increasing diversity is to alter the amino acid residue sequence of one or more polypeptide determinants of an epitope-, receptor-, or other specific binding pair-member binding complex. Alterations can be conveniently introduced at the nucleic acid level by mutation of the nucleic acid, such as in a PCR reaction as described above. PCR mutagenesis can be random or directed to specific nucleotide sequences, as is generally well known. Conducting PCR under conditions favorable for random mutagenesis has been described previously, and is referred to as "error prone PCR." Similarly, directed mutagenesis involves the use of PCR primers designed to target a specific mutation into a nucleotide segment, typically by use of a mismatch.

Other amplification procedures, such as isothermal amplification (J. C. Guatelli et al., *Proc. Natl. Acad. Sci. USA* 87: 1874–1878 (1990)), can also be used.

Methods for in vitro evolution of nucleic acids, involving mutagenesis and selection, are disclosed, for example, in J. Tsang & G. F. Joyce, "Evolutionary Optimization of the Catalytic Properties of a DNA-Cleaving Ribozyme," *Biochemistry* 33: 5966–5973 (1994).

Methods for in vitro mutagenesis to yield diverse populations of nucleic acids are of course adaptable to nucleic acids encoding polypeptide determinant genes, as is obvious to one skilled in the art. See for example, R. C. Caldwell & G. F. Joyce, "Randomization of Genes by PCR Mutagenesis," *PCR Meth. & Applications* 2: 28–33 (1992); A. R. Davidson & R. T. Sauer, "Folded Proteins Occur Frequently in Libraries of Random Amino Acid Sequences," *Proc. Natl. Acad. Sci. USA* 91: 2146–2150 (1994); A. P. Brunet et al., "The Role of Turns in the Structure of an α-Helical Protein," *Nature* 364: 355–358 (1993); W.

Mandecki, "A Method for Construction of Long Randomized Open Reading Frames and Polypeptides," *Prot. Engineerinq* 3: 221–226 (1990); J. D. Hermes et al., "Searching Sequence Space by Definably Random Mutagenesis: Improving the Catalytic Potency of an Enzyme," *Proc. Natl. Acad. Sci. USA* 87: 696–700 (1990); M. H. Hecht & R. T. Sauer, "Phage Lambda Repressor Revertants," *J. Mol. Biol.* 186: 53–63 (1985); D. K. Dube & L. A. Loeb, "Mutants Generated by the Insertion of Random Oligonucleotides into the Active Site of the β-Lactamase Gene," *Biochemistry* 28: 5703–5707 (1989); J. D. Hermes et al., "A Reliable Method for Random Mutagenesis: The Generation of Mutant Libraries Using Spiked Oligodeoxyribonucleotide Primers," *Gene* 84: 143–151 (1989); A. R. Oliphant & K. Struhl, "An Efficient Method for Generating Proteins with Altered Enzymatic Properties: Application to β-Lactamase," *Proc. Natl. Acad. Sci. USA* 86: 9094–9098 (1989); U.S. Pat. No. 5,223,409 to Ladner et al., issued Jun. 29, 1993; and "Current Protocols in Molecular Biology" (F. M. Ausubel et al., eds., Current Protocols, 1994), vol. 1, pp. 8.0.1–8.4.7), all incorporated herein by this reference.

Figure 19:
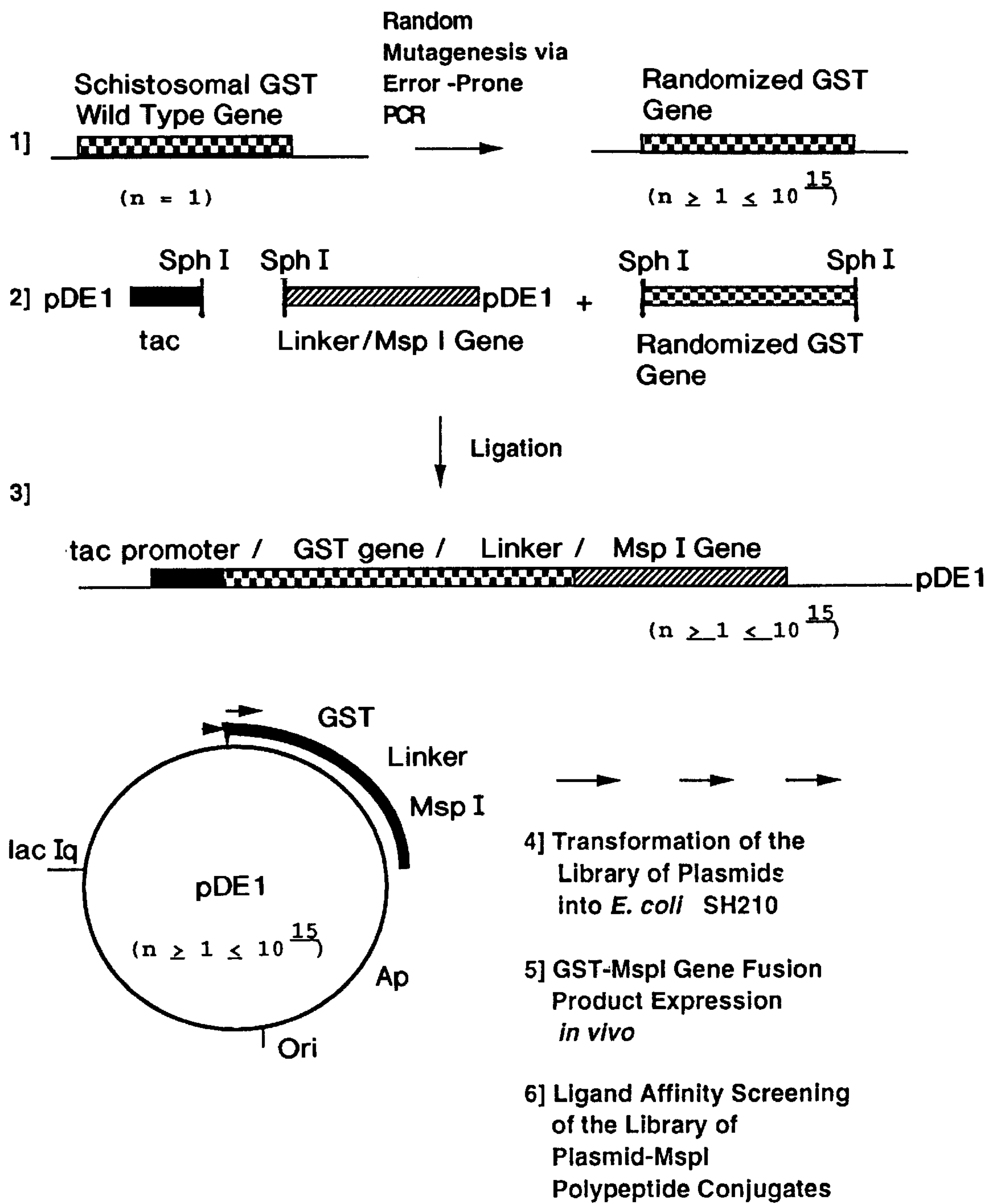
FIG. 19 is a diagram showing, schematically, the preparation of a plasmid library encoding a mutagenized polypeptide determinant covalently linked to a DNA methylase.

This procedure is shown schematically in FIG. 19.

These libraries according to the present invention can be used in a number of methods. For example, a method for obtaining a purified plasmid-polypeptide determinant conjugate that binds a predetermined target moiety can comprise:

(1) causing expression of a gene fusion product from members of a library of plasmids, each plasmid encoding a gene fusion product, to produce a plurality of polypeptide determinants, each polypeptide determinant being an expressed gene fusion product;

(2) forming an irreversible covalent joining of the polypeptide determinants of step (1) to the plasmids encoding them to form a library of plasmid-polypeptide determinant conjugates; and (3) isolating a plasmid-polypeptide determinant conjugate that binds a predetermined target moiety from the library of plasmid-polypeptide determinant conjugates.

This is a method of isolating a plasmid-polypeptide determinant conjugate that binds a predetermined target moiety. As discussed below, in conjunction with mutagenesis of the original polypeptide determinant, the method can be used to isolate mutants with increased affinity or other properties. In this method, the step of isolating the plasmid-polypeptide determinant conjugate that binds a predetermined target moiety can comprise:

(a) isolating the library of plasmid-polypeptide determinant conjugates of step (2); and (b) contacting the library of plasmid-polypeptide determinant conjugates with the predetermined target moiety for a period sufficient to allow the polypeptide determinant and the predetermined target moiety to form a complex.

Once a purified plasmid-polypeptide determinant conjugate is obtained, the plasmid-polypeptide determinant conjugate can be substantially deproteinized to obtain a purified plasmid obtaining a polypeptide determinant. This can be done by use of non-specific proteolytic enzymes such as pronase or protease K, typically in the presence of a chaotropic agent such as sodium dodecyl sulfate (SDS). This is followed by extraction of the DNA with phenol, which can be used in conjunction with chloroform and isoamyl alcohol. The DNA extracted from this procedure is subsequently precipitated with ethanol. These techniques are described, for example in D. M. Wallace ("Large- and Small-Scale Phenol Extractions," in *Guide to Molecular Cloning Techniques* (S. L. Berger & A. R. Kimmel, eds., Methods in Enzymology, vol. 152, Academic Press, Orlando, 1987), pp. 33–41, and in D. M. Wallace, "Precipitation of Nucleic Acids," in *Guide to Molecular Cloning Techniques*, supra, pp. 41–48. Although complete deproteinization of the plasmid is not possible because of the covalent linkage at the cytosine in the methylase conjugation element, a few amino acids remaining at this site after deproteinization will not interfere with cleavage, transcription, or amplification procedures such as those described below.

A method for obtaining a library of plasmid-polypeptide determinant conjugates according to the present invention can comprise:

(1) causing expression of gene fusion products from each of a library of plasmids, each plasmid encoding a polypeptide determinant;

(2) forming an irreversible covalent joining of gene fusion products to the plasmids encoding the gene fusion products so that each gene fusion product is joined to the plasmid encoding it to form a library of plasmid-polypeptide determinant conjugates; and (3) isolating the library of plasmid-polypeptide determinant conjugates.

The library can incorporate mutagenized polypeptide determinants derived from an original wild-type polypeptide determinant by mutagenesis as described above. Once a plasmid-gene fusion product conjugate is isolated, a DNA fragment can then be isolated from the plasmid-gene fusion product conjugate. The DNA fragment includes the polypeptide determinant gene linked to a methylase conjugation element, with the gene fusion product covalently joined to the methylase conjugation element. In this isolated DNA fragment, the gene for the DNA methylase has been removed. Typically, this is done by restriction endonuclease cleavage at restriction endonuclease sites surrounding the DNA methylase gene. To make this feasible, restriction endonuclease sites for known restriction endonucleases can be introduced in the linker or in the region of the plasmid surrounding the DNA methylase gene to provide for this isolation step.

The DNA fragment so isolated still contains the gene fusion product covalently attached to the methylase conjugation site through a cytosine in the methylase conjugation site. This DNA fragment can then be deproteinized as described above to form a purified polynucleotide fragment encoding a polypeptide determinant, with the DNA methylase having been removed.

The purified polynucleotide fragment isolated can be obtained from a library of plasmid-polypeptide determinant conjugates after contacting the library with a predetermined target moiety for a sufficient period to allow the polypeptide determinant and a predetermined target moiety to form a complex. This is a way of isolating a purified polynucleotide fragment encoding a polypeptide determinant in which the polypeptide determinant forms a complex with a predetermined target moiety. As described in below in Section VI, this procedure can be used to isolate purified polynucleotide fragments that encode a polypeptide determinant that bind the target moiety with a defined affinity by choosing the conditions under which the complex is formed. This allows, for example, the isolation of receptor proteins that bind their ligands with an affinity greater than a predetermined value by forming the complex under conditions such that only receptor proteins that bind with the required affinity will form a stable complex. This can be accomplished by forming the complex at, for example, relatively high salt or in the presence of an inhibitor of binding.

The purified polynucleotide fragment encoding the polypeptide determinant can then be cloned into a suitable plasmid in order to prepare a polypeptide determinant gene expression plasmid. The polypeptide determinant gene expression plasmid has the polypeptide determinant gene and a promoter operatively linked to the polypeptide determinant gene for promoting transcription of the polypeptide determinant gene as messenger RNA. Typically, the polypeptide determinant gene encodes a polypeptide determinant having a binding activity specific for a predetermined target moiety. This binding activity can be selected as described above to obtain polynucleotides encoding polypeptide determinants binding their ligands with an affinity greater than a certain specified value. Expression plasmids for expression of cloned DNA in prokaryotic hosts, particularly *Escherichia coli*, are well known in the art and need not be described here in detail. Such plasmids are described, for example, in J. Sambrook, "Molecular Cloning: A Laboratory Manual," supra, vol. 3, ch. 17, and in P. Balbas & F. Bolivar, "Design and Construction of Expression Plasmid Vectors in Escherichia coli," in *Gene Expression Technology* (D. V. Goeddel, ed. Methods In Enzymology, vol. 185, Academic Press, San Diego, 1991), pp. 14–36.

Typically, the protein product is expressed as a fusion protein. Typical plasmids include pBR322, pDF41, pRK356, pBEU50, pRK2501, RSF1010, pRK353, the pUR series of vectors, such as pUR278, pUR288, pUR289, pUR290, pUR291, pUR292, pEX2, pKC30, and other plasmids. If the polypeptide determinant is expressed as an intact native protein, a strong, regulated promoter and an efficient ribosome-binding site are required.

Typical promoters include the bacteriophage $\lambda p_L$ promoter, the trp-lac promoter or tac promoter and the bacteriophage T7 promoter; other prokaryotic promoters subject to regulation are also known and can be used. Other prokaryotic hosts can also be used and are known in the art, such as *Salmonella typhimurium*. Still other prokaryotic hosts suitable for expression are also known in the art.

Polypeptide determinant gene expression plasmids according to the present invention can then be used to transfect or transform suitable prokaryotic hosts to produce the polypeptide determinant by expression of the polypeptide determinant from the polypeptide determinant gene expression plasmid.

Another aspect of the present invention is a method for obtaining a library of gene-gene product conjugates. In general, the method comprises:

(1) causing expression of gene fusion products from each of a library of plasmids, each plasmid encoding a polypeptide determinant;

(2) forming an irreversible covalent joining of gene fusion products to the plasmids encoding the gene fusion products so that each gene fusion product is joined to the plasmid encoding it to form a library of plasmid-polypeptide determinant conjugates;

(3) isolating a library of plasmid-polypeptide determinant conjugates; and (4) from each member of the library of plasmid-polypeptide determinant conjugates, isolating a DNA fragment including a polypeptide determinant gene linked to a methylase conjugation element with the methylase conjugation element being joined to the gene fusion product to form a library of gene-gene product conjugates.

The library of plasmids can be formed incorporating a polypeptide determinant that is mutagenized from an original wild-type polypeptide determinant as described above. The DNA fragments isolated each contain polypeptide determinant genes linked to a methylase conjugation element, with the gene fusion product covalently joined to a cytosine analog in the methylase conjugation element. Thus, a library of gene-gene product conjugate results.

Another aspect of the present invention is a method for making a plasmid-polypeptide determinant conjugate. In general, this method comprises:

(1) introducing a plasmid into a host cell to form a transformed cell, the host cell being capable of incorporating a cytidine suicide analog into its DNA to partially replace cytidine, the plasmid including:

(a) a gene encoding a DNA methylase and a gene encoding a polypeptide determinant covalently joined, either directly or through a linker, the gene fusion construct encoding a gene fusion product including a cytosine (C-5) DNA methylase having a methyltransferase activity and a polypeptide determinant covalently joined thereto, either directly or through a peptide linker;

(b) a promoter operatively linked to the gene fusion construct for promoting transcription of the gene fusion construct as messenger RNA; and (c) a methylase conjugation element linked to the gene fusion either directly or through an intervening sequence, the methylase conjugation element including a methylase binding site;

(2) growing the transformed cell on a defined medium including a cytidine suicide analogue to incorporate the cytidine suicide analogue into the methylase binding site;

(3) causing expression of the gene fusion product from the plasmid of the transformed cell; and (4) forming an irreversible covalent joining of the gene fusion product to the methylase binding site of the plasmid.

This is a method for making a single plasmid-polypeptide determinant conjugate, and yields the entire plasmid, including the DNA methylase gene and any linker present. The methylase conjugation element can include 1 to 50 copies of the methylase binding site, so that 1 to 50 molecules of the gene fusion product are conjugated in the plasmid-polypeptide determinant conjugate via the methylase conjugation element.

Another aspect of the present invention is a method for obtaining a nucleotide sequence encoding a polypeptide determinant that binds a predetermined target moiety.

In general, this method comprises:

(1) causing expression of a gene fusion product from a library of plasmids, each plasmid within the library of plasmids including:

(a) a gene fusion including a DNA methylase gene and a polypeptide determinant gene covalently joined thereto, the gene fusion encoding a gene fusion product including a cytosine (C-5) DNA methylase and a polypeptide determinant covalently joined thereto;

(b) a promoter operatively linked to the gene fusion construct for promoting transcription of the gene fusion construct as messenger RNA; and (c) a methylase conjugation element linked to the gene fusion construct, the methylase conjugation element including a methylase binding site;

(2) forming an irreversible covalent joining of the gene fusion product of each plasmid in the library of plasmids to the plasmid encoding the gene fusion product to form a library of plasmid-polypeptide determinant conjugates;

(3) from the library of plasmid-polypeptide determinant conjugates, isolating a plasmid-polypeptide determinant conjugate that binds a predetermined target moiety; and (4) determining the nucleotide sequence of the polypeptide determinant gene encoded within the gene fusion construct of the plasmid-polypeptide determinant conjugate isolated in step (3).

Once the plasmid-polypeptide determinant conjugate that binds a predetermined target moiety is isolated, the nucleotide sequence of the polypeptide determinant gene encoded within the gene fusion construct of the plasmid-polypeptide determinant conjugate can be obtained by standard techniques. In general, the DNA is isolated from the plasmid after deproteinization, cleaved with appropriate restriction endonucleases, and subjected to DNA sequencing.

Methods of nucleotide sequencing, particularly DNA sequencing, are well known in the art and need not be described in detail here. Such methods are described, in general, in J. Sambrook et al., "Molecular Cloning: A Laboratory Manual," supra, vol. 2, ch. 13, pp. 13.1–13.104. In general, the two most commonly used methods of sequencing are the Gilbert-Maxam chemical cleavage method and the Sanger dideoxynucleotide chain termination method. The latter is typically performed subsequent to the cloning of the DNA sequence into a bacteriophage M13 vector. One or both strands of a double-strand DNA sequence can be sequenced; if both strands are sequenced, the second strand serves as a check upon the first strand.

Once the plasmid-polypeptide determinant conjugate that binds a predetermined target moiety is isolated, a nucleic acid fragment encoding essentially the gene fusion construct, or alternatively, encoding the polypeptide determinant gene can be obtained. This is typically done by deproteinization, isolation, and restriction endonuclease cleavage as described above. Other techniques, such as primer-based sequence-specific amplification, i.e. the polymerase chain reaction, the ligase amplification reaction, or other specific amplification reactions, can be carried out to obtain a sufficient quantity of nucleic acid for sequencing and/or subsequent recloning as required. These methods need not be described further here.

Primer-based sequence-specific amplification methods, such as PCR, can be performed on the plasmid in the plasmid-polypeptide conjugate without prior deproteinization or cleavage of the DNA as long as the primers used do not define a region for amplification that includes a polypeptide-nucleic acid covalent linkage.

V. GROWTH AND PRODUCTION OF PLASMID-POLYPEPTIDE DETERMINANT CONJUGATES

A. Bacterial Strains

The chemistry of the invention requires particular properties of the strains of *E. coli* used to produce the linkage of gene fusion product and plasmid DNA in vivo. In particular, several genotypes are preferable to ensure incorporation of 2'-deoxy-5-azacytidine or 2'-deoxy-5-fluorocytidine into DNA, although it is well known in the art that 2'-deoxy-5-azacytidine ("5AC") and 2'-deoxy-5-fluorocytidine ("5FC") are incorporated into prokaryotic and eukaryotic DNA in wild-type *E. coli* strains (D. V. Santi et al., "Covalent Bond Formation Between a DNA-Cytosine Methyltransferase and DNA Containing 5-Azacytosine," *Proc. Natl. Acad. Sci. USA* 81: 6993–6997 (1984); S. Friedman, "The Irreversible Binding of Azacytosine-Containing DNA Fragments to Bacterial DNA(cytosine-5)methyltransferases," *J. Biol. Chem.* 260: 5698–5705 (1985); S. Friedman, "The Effect of Azacytosine Containing DNA," *Mol. Pharmacol.* 19: 314–320 (1981); V. Paces et al., "Incorporation of 5-Azacytidine into Nucleic Acids of *Escherichia coli,*" *Biochim. Biophys. Acta* 161:352–360 (1968); J. Doskocil et al., "Inhibition of Protein Synthesis by 5-Azacytidine in *Escherichia coli,*" *Biochim. Biophys. Acta* 145:771–779 (1967); S. M. Taylor & P. A. Jones, "Mechanism of Action of Eukaryotic DNA Methyltransferase," *J. Mol. Biol.* 162: 679–692 (1982); M. Tanaka et al., "Utilization of 5-Fluoro-2'-Deoxyuridine Triphosphate and 5-Fluoro-2'-Deoxycytidine Triphosphate in DNA Synthesis by DNA Polymerases $\alpha$ and $\beta$ from Calf Thymus," *Cancer Res.* 41:4132–4135 (1981); J. Kaysen et al., "Incorporation of 5-Fluorodeoxycytidine and Metabolites into Nucleic Acids of Human MCF-7 Breast Carcinoma Cells," *Cancer Res.* 46: 4534–4538 (1986); M. H. N. Tattersall et al., "The Mechanisms of Action of Three Fluorine Substituted Cytosine Analogs: Implications for Cancer Chemotherapy," *Biochem. Pharmacol.* 23: 2533–2536 (1974); G. M. Cooper & S. Greer, "Phosphorylation of 5-Halogenated Deoxycytidine Analogues by Deoxycytidine Kinase," *Mol. Pharmacol.* 9: 704–710 (1973).

Several genotypes are preferred to insure that 5-substituted cytidines do not end up as 5-substituted uracil and then become inactivators of thymidylate synthetase (E. M. Newman et al., "Metabolism and Mechanism of Action of 5-Fluorodeoxycytidine," *Proc. Natl. Acad. Sci. USA* 79: 6419–6423 (1982)) or end up incorporated into RNA. Thus, it is advantageous that the genotype of *E. coli* used lacks the enzymes that convert cytosine to uracil or cytidine to uridine. These enzymes are cytosine deaminase (codA genotype) and cytidine deaminase (cdd genotype). Particularly preferred strains include SH210 (*E. coli* Genetic Stock Center (CGSC) #7096), which is codA$^-$and mcrB$^-$. Many other codA$^-$and codA$^-$B$^-$strains are known.

Another particularly preferred strain is X2465 (CGSC #7307), which is codA$^-$, cdd$^-$, as well as pyrF$^-$and pyrG$^-$. Yet another preferred strain is JF618 (CGSC #5566) which is codA$^-$, cdd$^-$, pyrE$^-$and pyrG$^-$. Still another preferred strain is X2469 (CGSC #6448), which is codAa$^-$, cdd$^-$, pyrF$^-$and pyrG$^-$. The interconversion of cytosine and uracil is blocked in these strains, which prevents interference with tRNA synthesis and protein translation resulting from the incorporation of 5-substitute uracil (5-azauracil or 5-fluorouracil) into tRNA. Thus, when wild-type strains are grown on minimal media supplemented with 5-substituted cytosine or 5-substituted cytidine, 5-substituted cytidine is incorporated into DNA and RNA. However, when SH210, X2465, X2469, or JF628 are grown on minimal media supplemented with 5-substituted cytosine or 5-substituted cytidine, the incorporation into DNA occurs while RNA synthesis remains largely unaffected.

Additional requirements are introduced by the specificity of the methylases. In particular, the methylases require strains of *E. coli* that are Mcrb$^-$, to prevent restriction and attack of the DNA (J. E. Kelleher & E. A. Raleigh, "A Novel Activity in *Escherichia coli* K-12 that Directs Restriction of DNA Modified at CG Dinucleotides," *J. Bacteriol.* 173:5220–5223 (1991); E. A. Raleigh & G. Wilson, "*Escherichia coli* K-12 Restricts DNA Containing 5-Methylcytosine," *Proc. Natl. Acad. Sci. USA* 83:9070–9074 (1986); P. A. Waite-Rees, "Characterization and Expression of the *Escherichia coli* Mrr Restriction System," *J. Bacteriol.* 173:5207–5219 (1991)). Thus, strains such as SH210 (codA$^-$, mcrb$^-$) are particularly preferred.

It has been shown that 5-fluoro-2'-deoxycytidine is incorporated into DNA (M. Tanaka et al. (1981), supra; D. A. Boothman et al., "Metabolic Channeling of 5-Fluoro-2'-Deoxycytidine Utilizing Inhibitors of Its Deamination in Cell Culture," *Mol. Pharmacol.* 27:584–594 (1985); J. Kaysen et al. (1986), supra; D. V. Santi et al. (1984), supra; S. Friedman (1985), supra; S. Friedman (1981), supra).

It is known that 5-azacytidine is incorporated into *E. coli* DNA. In addition, the proteins produced prior to 5AC incorporation into DNA are stable after induction of gene expression and after addition of 5-azacytidine. If protein synthesis is begun before addition of the drug, synthesis of proteins and new polynucleotides continues (V. Paces et al. (1968), supra; J. Doskocil et al., (1967), supra).

Of particular importance for Hpa II methylase, an in vitro covalent bond formation has been deduced between the methylase and purified DNA isolated from *E. coli* grown in the presence of 5-azacytidine (D. V. Santi et al., "Covalent Bond Formation Between a DNA-Cytosine Methyltransferase and a DNA Containing 5-Azacytosine," *Proc. Natl. Acad. Sci. USA* 81: 6993–6997 (1984)). Thus, *E. coli* grown in the presence of 5-azacytidine incorporate 5-azacytidine into their DNA, and this DNA is an irreversible suicide substrate for a cytosine C-5 DNA methylase Hpa II.

Thus, 5-fluorocytidine, 5-azacytosine, or 5-azacytidine was used as the source of the modified cytidine moiety using SH210. The desired expression plasmid, pNRT2 or the like, encoding the DNA methylase/polypeptide determinant sequences under inducible transcriptional control, were transformed into SH210. SH210 transformants were then grown in batch culture with 5-fluorocytosine. Expression of the gene fusion construct is induced at mid-log phase. Covalent binding of the plasmid to the gene fusion product occurs in vivo. The cells are then harvested, gently lysed, and the plasmid-polypeptide determinant conjugates are isolated. The lysis procedure is typically performed under conditions that would preserve large aggregates and involve minimum shear stress. A suitable lysis procedure is that described in U.S. Pat. No. 5,270,170 to Schatz et al., incorporated herein by this reference. The lysis buffer contains 35 mM HEPES, pH 7.5 with KOH, 0.1 mM EDTA, 100 mM Na glutamate, 5% glycerol, 0.3 mg/ml bovine serum albumin (BSA), 1 mM dithiothreitol, and 0.1 mM phenylmethylsulfonylfluoride. Lysozyme is then added (0.03 volume at 10 mg/ml in 35 mM HEPES, pH 7.5 with KOH, 0.1 mM EDTA, and 100 mM Na glutamate), and the mixture is incubated on ice for 1 hour. The lysate is then centrifuged, e.g., at 20,000×g for 15 minutes. The supernatant can be concentrated, such as by ultrafiltration.

Figure 20A:
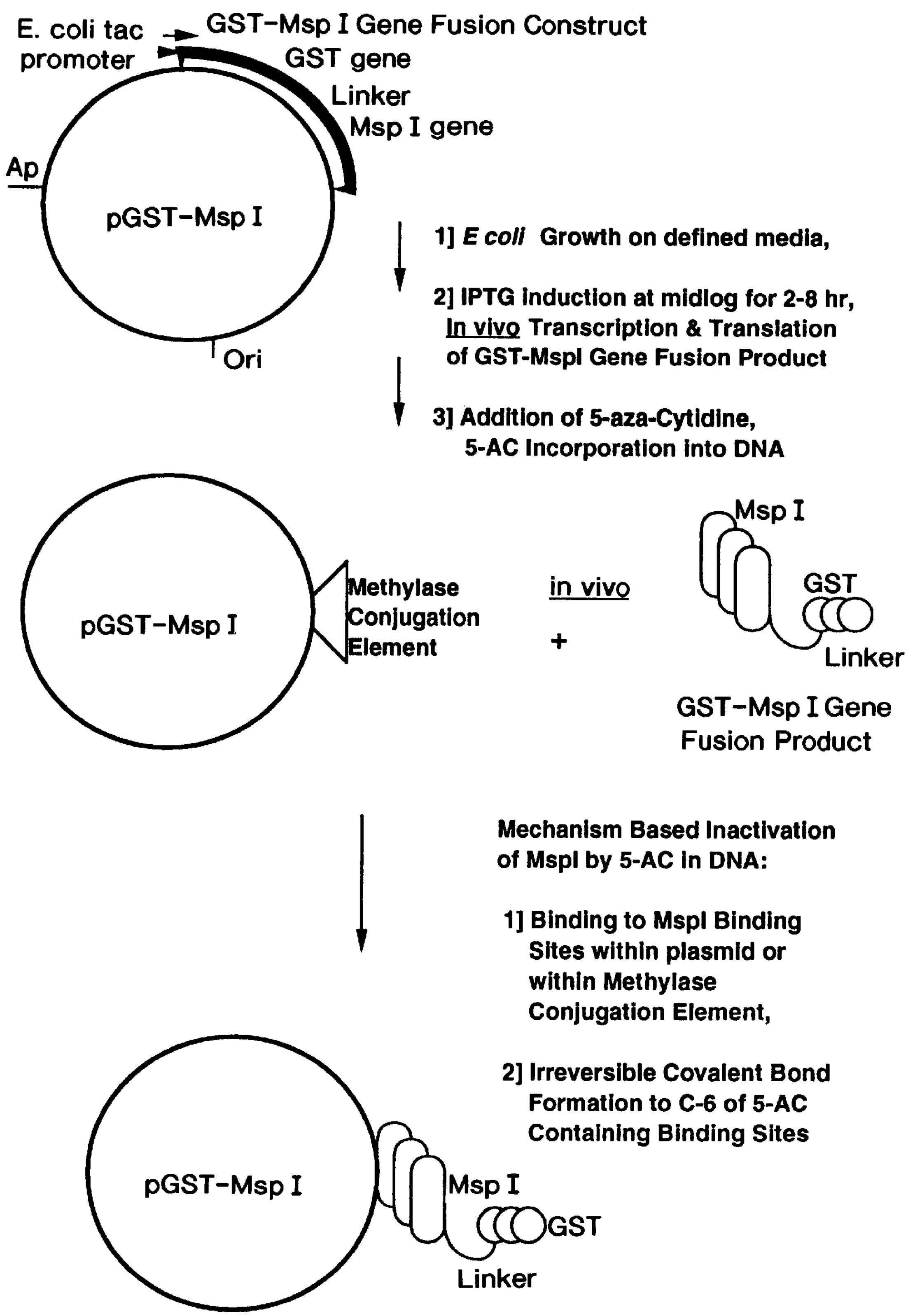
FIG. 20A is a diagram showing, schematically, the in vivo production of a library of plasmid-polypeptide determinant conjugates using azacytidine as the cytidine suicide analog.
Figure 20B:
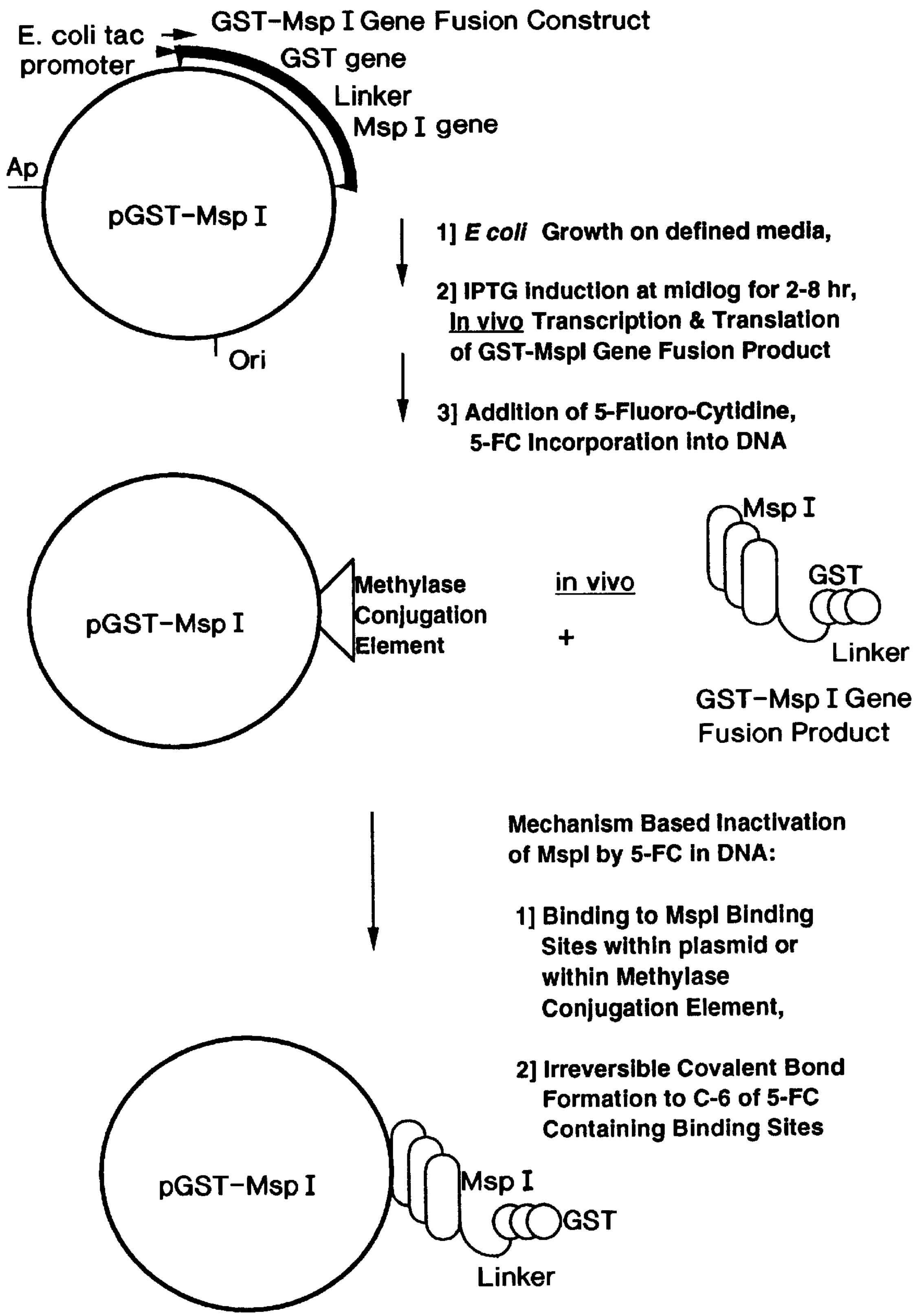
FIG. 20B is a similar diagram showing, schematically, the in vivo production of a library of plasmid-polypeptide determinant conjugates using fluorocytidine as the cytidine suicide analog.

This procedure is shown schematically in FIG. 20A using 5-azacytidine as the cytidine suicide analog and in FIG. 20B using 5-fluorocytidine as the cytidine suicide analog.

When 5-azacytidine or 5-fluorocytidine is used, fusion protein expression is induced during log phase growth, followed by addition of the 5-azacytidine. Cells are then incubated under these growth conditions for about 0.5 to about 3 hours, and then harvested to yield the plasmid-fusion protein conjugate.

VI. APPLICATIONS

The covalent linkage of DNA encoding a protein with that protein has a number of significant applications. As described above, one of the significant applications is the isolation of libraries containing a plurality of plasmid-polypeptide determinant conjugates, in which each plasmid is covalently joined to the polypeptide determinant encoded by that plasmid. One application of this, as indicated above, is the construction of a library derived from an original wild-type polypeptide determinant sequence by random mutagenesis within the sequence. As indicated below, this provides a novel method of in vitro protein evolution by the selection of proteins or peptides that have a difference in at least one property from the wild-type molecule. This property can be affinity for a ligand, such as a hormone.

Another application is functional cloning of low copy number "wild-type" proteins. In this application, a protein, even though present in a low copy number, can be cloned as long as a specific binding partner is available for the protein. This can be an antibody, receptor, or other binding partner. In this case, a library of ligand-polypeptide conjugates is prepared using a "shotgun" approach, by random cleavage of either the genome of the organism or preparation of cDNA from unfractionated mRNA. After the preparation of a library of plasmid-polypeptide determinant conjugates, the plasmid-polypeptide determinant conjugates in which the plasmids encode the low copy number protein of interest are isolated by detection of their binding to a predetermined moiety. This can be carried out by affinity chromatography, as described below. As described above, standard genetic engineering techniques, such as deproteinization, restriction endonuclease cleavage, DNA sequencing, and primer-based, sequence-specific nucleic acid amplification methods such as PCR can be applied to the isolated gene fusion construct or to the nucleic acid segment encoding the polynucleotide determinant. Alternatively, the amplification method, such as PCR, can be applied to the isolated plasmid-polypeptide determinant conjugate, for example, after affinity chromatography of the polypeptide determinant to isolate polypeptide determinants having the desired affinity for a ligand, such as a steroid hormone.

One particularly preferred primer-based, sequence-specific nucleic acid amplification method is PCR. PCR procedures are described, for example, in "PCR Protocols" (M. A. Innis et al., eds., Academic Press, San Diego, 1990), in "PCR Technology: Principles and Applications for DNA Amplification" (H. Erlich, ed., Stockton Press, New York, 1989), and in U.S. Pat. Nos. 4,683,195, 4,683,202, 4,800,159, and 4,965,188, all incorporated herein by this reference. In general, PCR involves denaturation, primer annealing, and primer extension steps, with a number of cycles. PCR is typically carried out by thermocycling, i.e., repeatedly increasing and decreasing the temperature of a PCR reaction mixture within a temperature range whose lower limit is generally about 10° C. to about 40° C. and whose upper limit is generally about 90° C. to about 100° C. The increasing and decreasing can be continuous, but are preferably phasic with time periods of relative temperature stability at each of the temperatures favoring polynucleotide synthesis, denaturation, and hybridization. Preferably, a thermostable DNA polymerase is used, such as the DNA polymerase from *Thermus aquaticus* (Tag), allowing the process to be carried out at elevated temperatures without the need for readdition of the DNA polymerase.

PCR can be used, for example, to amplify and clone either the entire gene fusion construct (methylase gene plus polypeptide determinant, together with any linker, if present), or either the methylase gene or the polypeptide determinant, if desired. In either case, appropriate primers can be chosen to include restriction endonuclease cleavage sites on either or both ends of the gene fusion construct in the plasmid so that these sites are replicated for further cleavage and cloning into another vector. Alternatively, sites for further manipulation, such as restriction endonuclease cleavage sites, promoters, and other sites, can be introduced as 5'-overhangs in a primer that then form double-stranded structures on the next round of replication.

An example of a suitable set of PCR primers is the PCR primers useful for amplification and cloning from plasmids containing fusions of the Msp I methylase gene and glutathione S-transferase (GST). These primers include:

(1) a 5'-primer covering a region upstream of the promoter for GST, namely the Ssp I site at base 167, with a sequence of 5'-G-T-T-C-T-G-G-C-A-A-A-T-A-T-T-C-T-G-A-A-A-T-G-A-G-C-T-G-3' (SEQ ID NO: 51);

(2) a 5'-primer covering a Bal I site within the GST coding region itself at base 466, with a sequence of 5'-C-A-C-A-G-T-C-T-A-T-G-G-C-C-A-T-C-A-T-A-C-G-T-T-A-T-A-T-A-G-3' (SEQ ID NO: 52);

(3) a 3'-primer covering an Eco RI site past the carboxyl-terminus of the methylase gene, with a sequence of 5'-G-T-C-A-G-T-C-A-G-T-C-A-C-G-A-T-G-A-A-T-T-C-C-A-C-T-T-C-T-T-G-3' (SEQ ID NO: 53); and (4) a 3'-primer at the carboxyl end of the GST gene, with a sequence of 5'-C-A-T-G-G-G-G-G-A-T-C-C-C-A-C-G-A-C-C-T-T-C-G-3' (SEQ ID NO: 54).

The above-described primers are particularly preferred for PCR amplification of altered variants of glutathione S-transferase.

These primers can be used pairwise, with one 5'-primer and one 3'-primer, to amplify and clone the DNA segments between them, either the GST gene alone or the GST-Msp I gene fusion, yielding the desired region. The restriction endonucleases used for subsequent cloning into a vector depend on the restriction endonuclease sites generated by the PCR amplification. For in vitro selection and evolution of altered GST enzymes, primers 1 and 4 (SEQ ID NO: 51 and 54) are particularly preferred for PCR amplification of the GST gene. Primers 1 and 4 may also be used in subsequent error-prone PCR reactions to prepare second, third, or fourth generation GST mutants, or GST mutants of subsequent generations. These new mutants are particularly suitable for xenobiotic drug screening.

In addition to analytical techniques useful for studying the nucleic acid portion of the plasmid-polypeptide determinant conjugate, analytical techniques can also be applied to the polypeptide determinant portion of the conjugate. In particular, methods for isolating proteins on the basis of specific binding affinity, referred to generally as affinity chromatography, can be used if the polypeptide determinant has an affinity for a binding partner such as a ligand. Such ligands include carbohydrates, peptides, hormones, nucleic acids, enzyme substrates and inhibitors, proteins, and antigens. Other ligands can also be used. The use of affinity chromatography for screening is shown schematically in FIG. 21.

Affinity chromatography is described generally in G. T. Hermanson, "Immobilized Affinity Ligand Techniques" (Academic Press, San Diego, 1991). A variety of solid supports can be used, including agarose, cellulose, controlled pore glass, silica, acrylamide derivatives, methacrylate derivatives, polystyrene and its derivatives, and membranes. A particularly preferred affinity chromatography medium which is specific for glutathione S-transferase is glutathione-Sepharose 4B (Pharmacia Biotech, Inc.). The GST-Msp I methylase fusion product is readily purified by conventional column chromatography by binding the GST-Msp I methylase fusion product to the glutathione-Sepharose column followed by subsequent elution with reduced glutathione (C. Taylor et al. (1993), supra).

Typically, the ligand is covalently bound to the solid support, often through a spacer arm. A number of reagents can be used for coupling, including cyanogen bromide, N-hydroxysuccinimide esters, carbonyldiimidazole, tosyl chloride, tresyl chloride, divinylsulfone, azlactone, trichloro-s-triazine, iodoacetyl and bromoacetyl reagents, malemides, pyridyl disulfide, divinylsulfone, hydrazide, diazonium, and other reagents. The protein-polypeptide conjugate is then bound to the immobilized ligand and removed by a change in conditions such as a change in pH, an increase in ionic strength, or an increase in temperature. Either stepwise or gradient elution can be used.

Another application of the present invention is in vitro evolution and selection of polypeptide determinants and nucleic acid segments encoding the polypeptide determinants in which the polypeptide determinants have at least one property altered from a wild-type polypeptide. In general, this method comprises:

(1) obtaining a nucleic acid segment encoding the wild-type polypeptide;

(2) subjecting the nucleic acid segment encoding the wild-type polypeptide to random mutagenesis to generate a plurality of mutagenized nucleic acid segments;

(3) constructing a library of plasmids from the plurality of mutagenized nucleic acid segments, each plasmid within the library of plasmids including:

(a) a gene fusion construct including a DNA methylase gene and one of the plurality of mutagenized nucleic acid sequences covalently joined thereto, the gene fusion construct encoding a gene fusion product including a cytosine (C-5) DNA methylase having a methyltransferase activity and a polypeptide determinant covalently joined thereto;

(b) a promoter operatively linked to the gene fusion construct for promoting transcription of the gene fusion construct as messenger RNA; and (c) a methylase conjugation element linked to the gene fusion constructs the methylase conjugation element including a methylase binding site having a nucleotide sequence including a cytidine suicide analog capable of irreversibly binding the cytosine (C-5) DNA methylase of the gene fusion product;

(4) causing expression of the gene fusion product from each of the library of plasmids;

(5) forming an irreversible joining of the gene fusion product to the plasmid encoding the gene fusion product for each member of the library of plasmids, forming a library of plasmid-polypeptide determinant conjugates;

(6) isolating a plasmid-polypeptide determinant conjugate from the library of plasmid-polypeptide determinant conjugates that binds a predetermined target moiety in a manner such that only plasmid-polypeptide determinant conjugates that have a property altered when compared to the wild-type polypeptide bind the target moiety;

(7) deproteinizing the plasmid-polypeptide determinant conjugate obtained in step (6) to form a purified plasmid encoding a polypeptide determinant having an altered property; and (8) isolating from the purified plasmid of step (7) a nucleic acid segment that encodes a polypeptide determinant having at least one property altered when compared with the wild-type polypeptide determinant.

Alternatively, the method can omit the deproteinization step, in which case the isolation of the nucleic acid segment that encodes the polypeptide determinant having at least one altered property can be performed by amplifying the nucleic acid segment encoding the polypeptide determinant with the at least one altered property by a sequence-specific primer-based amplification method employing at least two primers, such as PCR.

The altered property can be an increased affinity of the receptor formed by the polypeptide determinant for its ligand. Thus, through one in vitro protein evolution cycle which includes: random mutagenesis of the GST gene, expression of a library of GST-Msp I gene fusion products, and selection of GST enzymes using the methylase linking reaction coupled to affinity chromatography using glutathione-Sepharose 4B, altered glutathione S-transferase enzymes are identified and their gene sequences are readily determined. The altered ST enzymes may have altered affinity for glutathione relative to that of wild-type GST.

The step of isolating the plasmid-polypeptide determinant conjugate that binds the predetermined target moiety in such a way that only the polypeptide determinant with at least one altered property binds the target moiety can comprise the step of binding the plasmid-polypeptide determinant conjugate to a ligand, such as on an affinity column, under conditions such that the wild-type polypeptide determinant does not bind to the ligand and only polypeptide determinant conjugates with increased affinity for the ligand bind to the ligand. Properties other than increased affinity can be selected by this method. For example, antibodies or complementarity-determining regions of antibodies can be selected on the basis of freedom from cross-reactions by performing affinity chromatography using the immobilized cross-reacting ligand and selecting those plasmid-polypeptide determinant conjugates that do not bind to the cross-reacting ligand, and then performing affinity chromatography on this subset of plasmid-polypeptide determinant conjugates to select those that have affinity for the desired ligand.

Although affinity chromatography is generally preferred, in some applications other means of determining binding between the polypeptide determinant and the ligand, such as filter binding or centrifugation, can be used. Such methods are well known in the art and need not be described further here.

A particularly preferred ligand is glutathione in which case this method can be used to isolate glutathione S-transferase molecules with an altered reactivity with glutathione.

The nucleic acid segment encoding the polypeptide determinant with at least one altered property can then be subjected to further random mutagenesis to produce a plurality of doubly mutagenized nucleic acid segments. A second library of plasmids can then be constructed. In general, this procedure comprises:

(9) subjecting the nucleic acid segment of step (8) encoding the polypeptide determinant with at least one altered property to further random mutagenesis to produce a plurality of doubly mutagenized nucleic acid segments;

(10) constructing a second library of plasmids, each plasmid comprising a gene fusion construct, a promoter, and a methylase conjugation element, each gene fusion construct including a DNA methylase gene and one of the plurality of doubly mutagenized polypeptide determinant genes covalently joined thereto;

(11) causing expression of the gene fusion product from each of the second library of plasmids;

(12) forming an irreversible covalent joining of each of the gene fusion products to the plasmid encoding for the gene fusion product to form a second library of plasmid-polypeptide determinant conjugates;

(13) isolating a plasmid-polypeptide determinant conjugate from the second library of plasmid-polypeptide determinant conjugates that binds a predetermined target moiety in such a way that neither the wild-type protein determinant nor the protein determinant encoded by the nucleic acid segment of step (8), above, binds the predetermined target moiety; and

(14) deproteinizing the plasmid-polypeptide determinant conjugate obtained in step (13) to form a purified plasmid encoding a doubly mutagenized polypeptide determinant.

The polypeptide determinant encoded by the doubly mutagenized nucleic acid segment can be selected in such a way so that it binds a ligand with an increased affinity so that the final isolation step occurs under conditions such that neither the wild-type polypeptide moiety nor the polypeptide moiety encoded by the originally selected singly mutagenized nucleic acid segment binds. Thus, polypeptide determinants with further increased affinity can be selected by the second step. This procedure can be further repeated.

A nucleic acid segment encoding a polypeptide determinant with at least one altered property selected from this process can be amplified by a primer-based sequence-specific amplification technique such as the polymerase chain-reaction amplification technique. The amplified nucleic acid can then be sequenced by standard techniques such as the Sanger chain termination technique or the Maxam-Gilbert chemical cleavage technique, as described above.

The present invention is illustrated by the following Examples. The Examples are for illustrative purposes only and are not intended to limit the invention.

EXAMPLES

Example 1

Construction of GST-Msp I Expression Vector

The construction of a GST-Msp I expression vector (C. Taylor et al. (1993), supra) started with a 2.9-kb Eco RI-Hind III restriction fragment including the Msp I restriction and modification genes, also including a Eco RI site. This fragment was subjected to PCR amplification with two primers, a first primer of the sequence 5'-T-G-A-C-G-G-C-G-C-A-T-G-C-A-A-C-C-T-G-A-3' (SEQ ID NO: 1), which includes a partial mismatch to introduce a Sph I site, and a second primer, the M13–20 primer, with the sequence 5'-G-T-A-A-A-A-C-G-A-C-G-G-C-C-A-G-T-3' (SEQ ID NO: 2). The PCR amplification generated a fragment including the Msp I coding region with a mutation introduced in the second codon so that the original sequence of the first four codons, 5'-A-T-G-A-A-A-C-C-T-G-A-A-3' (SEQ ID NO: 3), was mutated to yield 5'-A-T-G-C-A-A-C-C-T-G-A-A-3' (SEQ ID NO: 4). This changed the second codon from one coding for lysine to a codon for glutamine. This mutation also introduced a Sph I restriction endonuclease cleavage site.

Figure 22:
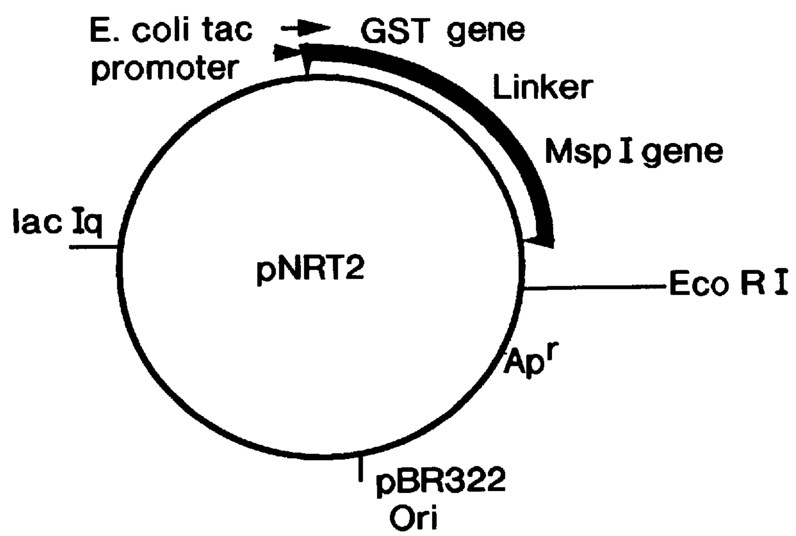
FIG. 22 is a schematic diagram of the plasmid pNRT2 (GST=glutathione S-transferase gene)

The resulting fragment was then cloned into the pBS vector (Stratagene, San Diego, Calif.) into a blunt-ended Sma I site within the pBS plasmid. This blunt-end ligation resulted in the Msp I methylase gene being inserted into pBS in the two possible orientations. The orientation in which the amino-terminus of Msp I is closer to the Eco RI site located in the pBS plasmid near the Sma I site was used for subsequent cloning after digestion with Eco RI restriction endonuclease. The Eco RI fragment was cloned into the expression plasmid pGEX-3X (Pharmacia Biotech, Alameda, Calif.) which incorporates the gene for glutathione S-transferase from *Schistosoma japonicum*. The pGEX-3X plasmid allows cleavage of the methylase protein from the glutathione S-transferase with factor X protease, if desired. The resulting clone was then subjected to double digestion with Sma I and Sph I, removing unwanted DNA upstream of the start site for the methylase. The digest was then religated. This introduced a frameshift. To restore the original reading frame, the religated plasmid was digested with Bam HI, the partially single-stranded ends filled in, and the resulting construct religated again to yield the plasmid pNRT2 (FIG. 22). This construct has both the glutathione S-transferase gene and MspI methylase gene positioned contiguously in an open reading frame so that a GST-Msp I fusion product is formed through a peptide linker. The peptide linker is G-I-D-P-P (SEQ ID NO: 5).

The sequences of the resulting nucleotide segment and encoded fusion protein are shown in FIG. 3A through 3D, including the factor X cleavage site near the carboxy-terminal end of the glutathione transferase and the linker. For comparison, the sequences of the wild-type Msp I methylase gene and protein are shown in FIG. 4A through 4D, and the sequences of the mutated Msp I methylase portion of the fusion protein are shown in FIG. 5A through 5D.

Example 2

Cloning of Methylase Conjugation Element Into pNRT2

Figure 23:
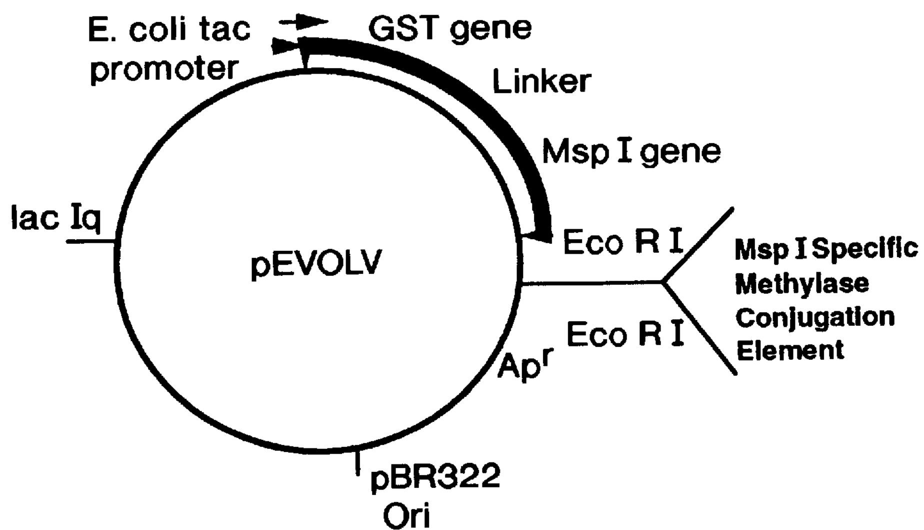
FIG. 23 is a schematic diagram of the resulting vector, designated pEVOLV, including the methylase conjugation element (MCE)

A methylase conjugation element is cloned into pNRT2 (Example 1) using the EcoR I site. After EcoR I digestion, the vector is dephosphorylated. A fragment is then ligated in using the cohesive ends. The fragment ligated in is shown in FIG. 16; the lines at the left and the right indicate the EcoR I site and divide residues that are part of the vector from residues that are part of the methylase conjugation element. The resulting vector, designated pEVOLV herein, includes a methylase conjugation element; its schematic diagram is shown in FIG. 23.

Example 3

Demonstration of 5-Azacytidine or 5-Fluorocytidine Incorporation into *E. coli* Plasmid DNA and of Methylase-DNA Linkage This prospective example is based on the procedure described in S. Friedman, "The Irreversible Binding of Azacytosine-Containing DNA Fragments to Bacterial DNA (cytosine-5)methyltransferases," *J. Biol. Chem.* 260: 5698–5705 (1985), with strains appropriate for the plasmids and methods of the present invention.

Preparation of Azacytidine- or Fluorocytidine-DNA Fragments

DNA fragments are prepared from plasmid pBR322 grown in a suitable strain of *E. coli*, such as SH210. The cells are grown in 500 ml of minimal A medium (J. H. Miller, "Experiments in Molecular Genetics" (Cold Spring Harbor Laboratory, Cold Spring Harbor, N.Y., 1972), pp. 432–433) supplemented with 40 μg/ml DL-methionine in 2-liter flasks at 37° C. with continuous agitation. When the culture reaches an $A_{550}$ of 0.5, it is treated with 20 μg/ml 5-azacytidine or 5-fluorocytidine. After a 3-hr incubation, an additional 20 μg/ml of drug is added and the incubation is terminated after a further 3 hr of incubation. The plasmid is extracted from cleared lysates of cells. The supernatant is extracted with an equal volume of phenol. The DNA is precipitated from the aqueous phase with 2 volumes of ethanol, dissolved in 2 ml of 10 mM Tris-HCl, pH 8, 1 mM EDTA (TE buffer), and treated with ribonuclease A (boiled 10 min to destroy deoxyribonuclease), 100 μg/ml, at 37° C. for 30 min.

The DNA is again extracted with an equal volume of phenol and precipitated with 2 volumes of ethanol. The DNA is dissolved in TNE buffer (50 mM Tris-HCl, 50 mM NaCl, 5 mM EDTA, pH 7.8) and chromatographed on a Sephadex G-100 (Pharmacia, Uppsala, Sweden) column (2.5×30 cm). The excluded volume contains the plasmid. The DNA is precipitated with ethanol and further purified by equilibrium density centrifugation in CsCl. The plasmid is then purified by centrifugation through a 5–20% sucrose gradient containing 1M NaCl and 0.1M potassium phosphate, pH 7.2, in a SW 27 rotor (Beckman, Fullerton, Calif.) at 27,000 rpm, 18° C., for 15 hr. The position of the plasmid DNA in the gradient is determined by its absorbance at 260 nm. The appropriate fractions are pooled and dialyzed against TE buffer. The DNA is precipitated with 2 volumes of ethanol and dissolved in TE buffer. The DNA (20 μg) is digested with 20 units of Msp I or Hinf I restriction endonuclease and dephosphorylated with calf intestine alkaline phosphatase. The digest is electrophoresed through an 8% polyacrylamide gel, prepared in TBE buffer (0.089M Tris, 0.089M boric acid, 2 mM EDTA), at 5 V/cm for 15 hr. The gel is stained with 1 μg/ml ethidium bromide and the appropriate bands are eluted by diffusion.

DNA fragments are end-labeled with $^{32}$p. The fragments are end-labeled to a specific activity of $1\times10^7$ cpm/μg.

Demonstration of Methylase-DNA Linkage

DNA-Enzyme Binding. The reaction mixture contains KCl, 100 mM, dithiothreitol, 20 mM, Tris-HCl, pH 7.7, 50 mM, bovine serum albumin, 500 μg/ml; EDTA, 1 mM; DNA, as indicated, 500–5000 cpm; and enzyme in a total volume of 30 μl. The reactions are incubated at 28° C. for 15 min. *E. coli* B DNA (2.5 mg/ml), 2 μl, or 6% SDS, 1 μl, is added, followed by 4 μl of 50% glycerol containing 0.1% bromphenol blue. The reaction mixture is then loaded on an 8% polyacrylamide gel prepared with TBE buffer and run at 5 V/cm for 15 hr. The gels are autoradiographed with one Dupont Lightning Plus intensifying screen at −70° C.

Electrophoresis. Protein electrophoresis is performed in SDS-polyacrylamide gels by the method of Laemmli (U. K. Laemmli, "Cleavage of Structural Proteins During the Assembly of the Head of Bacteriophage T4*," Nature* 227:680 (1970)) The protein is concentrated by precipitation with 10% trichloroacetic acid, washed twice with ethanol/ether (50:50), and dried prior to electrophoresis.

Enzyme Assay. The standard assay measures the transfer of [$^3$H]methyl groups to *E. coli* B DNA from AdoMet [methyl-$^3$H], as described in S. Friedman (1981), supra. The assay for the $K_m$ determination is modified from that of Rubin & Modrich (R. A. Rubin & P. Modrich, *J. Biol. Chem.* 252: 7263–7272 (1977). Reactions contain 50 μg of bovine serum albumin, 10 μmol of Tris-HCl (pH 8), 0.5 μmol of dithiothreitol, 0.5 μmol of EDTA, 17.5 μg of DNA, a concentration of [$^3$H]AdoMet varying from 0.25 μM to 2 μM, 855 μCi/mol, and enzyme in a volume of 0.1 ml. After incubation for 10 min at 37° C., 50-μl aliquots are spotted on 1.5-cm squares of filter paper (Whatman DE81). The papers are washed 5 times with 0.2M ammonium bicarbonate, 3 times with ethanol, and once with ether, and dried under a heat lamp; the radioactivity is determined in 5 ml of a toluene-based scintillation fluid. The assay is linear for 20 min with a quantity of enzyme that transfers 0.3 pmol of methyl group per min. Protein is determined by the method of Lowry et al. (O. H. Lowry et al., *J. Biol. Chem.* 193: 265–275 (1951)).

Determination of Base Methylated by Methyltransferase. Calf thymus DNA, 6 μg, is methylated in a reaction mixture containing 100 mM Tris-HCl, pH 8, 500 μg bovine serum albumin, 5 mM EDTA, 10 mM dithiothreitol, and 18 ng of enzyme in a volume of 0.2 ml for 30 min at 37° C. The DNA is purified by phenol extraction, precipitated with ethanol, washed with ethanol, and dried. The DNA is dissolved in 0.5 ml of formic acid and hydrolyzed in a sealed glass tube at 175° C. for 30 min. The hydrolysate is taken to dryness, dissolved in 20 μl of 0.1M HCl, and chromatographed on cellulose thin layer plates as described by Günthert et al. (U. Gunthert et al., *Proc. Natl. Acad. Sci. USA* 73: 3923–2927 (1976)). The spots are scraped off the plates and counted in scintillation fluid.

Determination of pBR322 Msp I DNA Fragments Methylated by the Methyltransferase. pBR322 DNA, 5 μg, extracted from *E. coli* B, is methylated with 4 μg of enzyme as described above. The DNA is dissolved in 20 μl of TE buffer and digested overnight with 5 units of Msp I endonuclease as described by the manufacturer (New England Biolabs). The DNA fragments are then separated by electrophoresis on a 7.5% polyacrylamide gel. The gel is dried and autoradiographed.

Methyltransferase Purification. *E. coli* B (R15) is grown in three 2-liter flasks, each containing 660 ml of SLBH medium (P. J. Greene et al., in *Methods in Molecular Biology* (R. D. Wickner, ed., Marcel Dekker Inc., New York, 1974), vol. 7, pp. 87–109) plus 0.02% sulfathiazole. Each flask is inoculated from a fresh overnight culture grown in the same medium. The flasks are incubated for 16 hours at 37° C. on a rotating platform. The pH of the cultures is adjusted to pH 7.3 with 2.5N NaOH and transferred to a high density fermentor containing 4 liters of SLBH medium, 400 ml of phosphate buffer (382 ml of 1.0M $K_2HPO_4$ plus 117 ml of 1.0M $KH_2PO_4$), and 60 ml of sulfathiazole are then added and the fermentor is assembled. Incubation is performed as described by Greene et al. (1974), supra. The culture stops increasing in mass at 1600 Klett units (Filter 54). The cells are harvested by centrifugation at 10,000×g in a continuous flow Lourdes centrifuge, washed with 10 mM Tris, pH 8, containing 5 mM 2-mercaptoethanol, and stored frozen. Typically, 120 g of cells are harvested.

The remaining purification steps are performed at 4° C. Cells (250 g) are suspended in 1250 ml of Buffer A (10 mM potassium phosphate, pH 7, 1 mM EDTA, 7 mM 2-mercaptoethanol) containing 1 mM sodium azide, 0.4M NaCl, and 25 μg/ml phenylmethylsulfonylfluoride. The cells are treated with 50 μg/ml lysozyme for 15 min and then sonicated five times with a sonicator. The solution is centrifuged at 30,000 rpm for 1 hr in a Beckman 30 rotor (Beckman Instruments). The supernatant is diluted 2.5-fold with Buffer A and loaded onto a P-11 phosphocellulose column (5×30 cm) at 2 ml per min. The column is washed with 500 ml of Buffer A containing 0.2M NaCl and the enzyme is eluted with a linear gradient generated by mixing 1500 ml of Buffer A containing 0.2M NaCl and 1500 ml of Buffer A containing 0.8M NaCl. The fractions containing enzyme activity are pooled and dialyzed for 4 hr against 10 volumes of Buffer A. The dialyzate is centrifuged at 10,000×g for 15 min and the supernatant is applied to a DE52 DEAE-cellulose column (2.5×12 cm) equilibrated with Buffer A containing 0.05M NaCl. The column is washed with 200 ml of the same buffer. The enzyme is eluted with a linear 600-ml gradient of 0.05M NaCl to 0.04M NaCl in Buffer A. The fractions containing enzyme activity are pooled and applied to a hydroxyapatite column (2×8 cm) equilibrated with Buffer A containing 0.2M NaCl. The column is washed with 100 ml of the same buffer and eluted with a linear gradient formed by mixing 125 ml of Buffer A containing 0.2M NaCl with 125 ml of 0.5M potassium phosphate, pH 7, containing 1 mM EDTA, 7 mM 2-mercaptoethanol, 0.2M NaCl, and 15 glycerol (Buffer B). The fractions containing enzyme activity are pooled, diluted 2-fold with Buffer A, and concentrated by absorption onto a 2.5×1.5 cm hydroxyapatite column equilibrated in Buffer A. The column is washed with 20 ml of Buffer A and eluted with Buffer B. The fractions containing protein are then applied to Bio-Gel A-0.5 m (100–200 mesh, 3×40 cm) (Bio-Rad, Richmond, Calif.) column and eluted with Buffer A containing 0.2M NaCl and 5% glycerol. Peak fractions are pooled and applied to a heparin-Sepharose column (1×8 cm) equilibrated with Buffer A. The column is washed with Buffer A and the enzyme eluted with an 80-ml linear gradient of 0.2M NaCl to 0.8M NaCl in Buffer A containing 20% glycerol. The active fractions are pooled and stored at 4° C.

Example 4

Preparation of *E. coli* DNA Containing 5-Azacytidine or 5-Fluorocytidine

This prospective example is based on the procedure described in D. V. Santi et al., "Covalent Bond Formation Between a DNA-Cytosine Methyltransferase and dNA Containing 5-Azacytosine," *Proc. Natl. Acad. Sci. USA* 81: 6993–6997 (1984), with strains appropriate for the plasmids and methods of the present invention. A suitable *E. coli* strain is grown in appropriately supplemented minimal medium until mid-log phase ($A_{600}$ approximately 0.5–0.6); to individual 10-ml cultures is added: (i) azacytidine at 25 μg/ml; (ii) 0.3 mCi of [6-$^3$H]azacytidine; (iii) 150 μCi of [$^3$H]thymidine; or (iv) 150 μCi of [$^3$H]thymidine plus azacytidine at 25 μg/ml. The culture containing [6-$^3$H] azacytidine is incubated for 30 min and the others for 1 hr prior to harvesting. The DNA preparations are isolated by a procedure known in the art with care taken to avoid exposure to acidic or basic conditions, which would result in the degradation of azacytosine residues. Cells are washed with 2 ml of cold 150 mM NaCl/100 mM $Na_2$EDTA/20 mM Tris-HCl, pH 7.4, and resuspended in 1.0 ml of the same buffer. The suspension is treated with 100 μg of lysozyme for 15 min at room temperature and brought to 1% in sodium dodecyl sulfate. After 5 min, the mixture is extracted three times with equal volumes of phenol/chloroform (1:1, vol/vol), and nucleic acids are precipitated with 2 volumes of ethanol. The precipitate is dissolved in 0.5 mM of 10 mM Tris-HCl, pH 7.4, 1.0 mM EDTA and treated with previously boiled pancreatic RNase at 100 μg/ml for 1 hr at 37° C. The solution is brought to 0.1M in NaCl and 0.2% in sodium dodecyl sulfate and extracted twice with phenol/chloroform; the DNA is precipitated with 2 volumes of ethanol. The precipitate is redissolved in 10 mM Tris-HCl, pH 7.4, 1.0 mM EDTA, and the DNA is precipitated with 2-propanol, redissolved in the same buffer, and stored at −80° C.

The tritium content of the [6-$^3$H]azacytidine-containing DNA is determined and calculated on the basis of the specific activity of the analog and the 50% G+C content of *E. coli* DNA; the tritium corresponds to a 1% substitution of the cytosine residues. To estimate the azacytosine content of azacytosine-containing DNA prepared with the unlabeled analog, the G+C content can be determined by HPLC after digestion to the component nucleotides. A solution (300 $\mu$l) containing 10 $\mu$g of [$^3$H]thymidine-containing azacytosine-containing DNA, 50 mM Tris-HCl, pH 8.2, 10 mM $MgCl_2$, and 70 units of deoxyribonuclease I is incubated at 37° C. After 2 hr, 3.6 units of snake venom diesterase and 2 units of bacterial alkaline phosphatase are added and incubation continued for 3 hr. The acid-soluble fraction is prepared and neutralized. HPLC using an Altex Ultra Sphere ODS column (5-$\mu$m diameter spheres; 4.6×250 mm) proceeds for loo min with a linear gradient of 0–10% (vol/vol) methanol containing 5 mM sodium hexanesulfonate/5 mM acetic acid, pH 3.3, at a flow rate of 1.2 ml/min. This system effectively separates all major ribo- and deoxyribonucleosides; no ribonucleosides are detected, verifying the absence of RNA contamination. The deoxycytidine-to-deoxyguanosine ratio is 0.74, indicating that 26% of the cytosine residues are replaced by azacytosine. This indicates that a replacement of a relatively large proportion of cytosine residues by azacytosine is feasible in *E. coli*.

Example 5

Preparation of a Library of Plasmid-Polypeptide Conjugates

Prospective Example

A wild-type gene from pDE1, encoding glutathione S-transferase from *S. japonicum*, is subjected to random in vitro mutagenesis by error-prone PCR reactions (R. C. Caldwell & G.F. Joyce (1992), supra) using 5'-primer 1 (SEQ ID NO: 51) and 3'-primer 3 (SEQ ID NO: 53), which are admixed with pDE1 to yield a randomized GST gene library containing up to $10^{15}$ variants. The linear fragments containing the intact GST-Msp I methylase gene construct, approximately 2 kb, are digested with Sph I restriction endonuclease to yield the approximately 700 bp GST gene with Sph I cohesive ends. The library of GST variants is thus the library of 700 bp Sph I fragments. The 700 bp fragment is purified from 1.2% agarose by electroelution and then cloned into Sph I-digested pDE1 vector DNA, to produce a library of pDE1 encoding GST variants fixed to the $NH_2$-terminus of the linker sequence fused to the $NH_2$-terminus of Msp I methylase. Alternatively, a new restriction endonuclease site can be engineered into the linker section by PCR or site-directed mutagenesis to facilitate directional ligation of the library of 700 bp GST genes.

The library of pDE1 variants is thus placed into an *E. coli* expression plasmid encoding the gene fusion product under IPTG inducible transcriptional control; it is transformed into *E. coli* SH210 (codA$^-$, mcrb$^-$). The transformed SH210 library is used to inoculate a 2-liter minimal medium culture containing 2% glucose, $MgSO_4$, $CaCl_2$, ampicillin, a vitamin supplement (containing biotin, D-Ca pantothenate, choline chloride, folic acid, i-inositol, niacinamide, pyridoxal hydrochloride, riboflavin, and thiamine hydrochloride) and arginine. SH210/pDE1 is then grown at 37° C. to mid-log phase, cooled to 25° C., and the gene fusion product is induced by the addition of IPTG to 1 mM. Induction is allowed to proceed for 2–6 hr at 25° C. At that point, 20–25 $\mu$g/ml of 5-azacytidine or 5-fluorocytidine is added, and the culture is allowed to continue to grow at 25° C. for 3 hr. Linkage of the GST-Msp I gene fusion product is allowed to occur in vivo, as the modified nucleotide is incorporated into DNA. The GST-Msp I gene fusion product encoded within the bacterial plasmid is transcribed and translated in vivo. The DNA methylase Msp I binds to its 4-base-pair recognition sequence at any of the 20 sites within pNRT2 and initiates the DNA methylation reaction, and as described above, becomes covalently attached to the 5-azacytidine or 5-fluorocytidine-containing plasmid DNA.

After expression is induced, the cells are harvested, gently lysed, and the plasmid/DNA-methylase/fusion library is isolated.

Example 6

Screening a Plasmid pDE1 GST-Msp I Gene Fusion Product Conjugate Library

Prospective Example

The covalent plasmid/methylase/fusion complex of Example 5 is isolated under gentle lysis conditions. A glutathione ligand affinity matrix utilizing glutathione ligand covalently bound to a solid support is equilibrated in lysis buffer. The library is then screened by conventional affinity chromatography. PCR cloning and amplification then yields genes encoding novel high affinity, altered receptors. Subsequent rounds of mutagenesis and screening yield in vitro evolved proteins.

Example 7

Purification of Active GST-Msp I Methylase Gene Fusion Product

This prospective example is based on the procedure described in C. Taylor et al., "Determination of the Order of Substrate Addition to Msp I DNA Methyltransferase Using a Novel Mechanism-Based Inhibitor," *Biochem. J.* 291:493–504 (1993). A suitable regime for extraction of soluble material involves growth at 30° C. in Luria broth. Extracts are prepared by sonication of cells which are resuspended in 0.1 volume of PBS, pH 7.3. Large-scale (500 ml) cultures are grown from an overnight 5-ml inoculum to an $A_{595}$ of 0.4, whereupon IPTG is added to give a final concentration of 0.05 mM and the cells are allowed to grow for a further 2 hr at 30° C. Harvested cells are resuspended in PBS (pH 7.3) and sonicated on ice. After brief centrifugation (40,000×g) to pellet insoluble material, the supernatant is applied directly to a reduced glutathione-agarose column pre-equilibrated in a buffer of 50 mM Tris-HCl, pH 8, and 1 mM EDTA. After 4 column volume washes with the loading buffer, the fusion protein is eluted with 3 ml of 10 mM reduced glutathione in 50 mM Tris-HCl, pH 8.0, 1 mM EDTA. The purity of the GST-Msp I methylase fractions (0.5 ml) is analyzed by SDS-polyacrylamide gel electrophoresis.

Example 8

Gel Retardation Assay for Determination of Fusion Protein Binding to Plasmid

This prospective example is based on the procedure described in C. Taylor et al. (1993), supra. The oligonucleotides are labeled at the 5'-end with [$\gamma$-$^{32}$P]ATP using T4 polynucleotide kinase. Unincorporated label is removed by gel filtration using Sephadex G-25 resin (Pharmacia) and a spun column procedure. Typically, 0.1 μg of fusion protein (final concentration 0.038 μM, assuming the fusion protein is dimeric) is incubated in Mtase buffer (50 mM NaCl, 50 mM Tris-HCl, pH 7.5, 10 mM EDTA, and 5 mM 2-mercaptoethanol) with 1 ng of labeled oligodeoxynucleotide (final concentration 0.004 μM) and 160 μM AdoMet in a final reaction volume of 20 μl. Incubation is typically for 35 min on ice. The reaction mixture is subsequently loaded onto a 4% non-denaturing polyacrylamide (19:1) gel in 0.5×TBE buffer (50 mM Tris, 0.4M boric acid, 1.25 mM EDTA) and electrophoresed for 2–3 hr at 100 V and 15° C. Protein-DNA complexes are visualized after autoradiography with intensifying screens at −70° C., overnight. Protein bound to the DNA retards the DNA in the gel.

Example 9

Demonstration of Covalent Linkage of GST-Msp I Methylase Gene Fusion Product with pNRT2 Containing 5-Azacytidine Prospective Example A. Preparation of 5-Azacytidine Plasmid DNA

*E. coli* SH210 transformed with plasmid pNRT2 are grown in 1 liter minimal medium, containing 2% glucose, M9 salts, 1 mM $MgSO_4$, 10 μM $CaCl_2$, 50 μg/ml ampicillin, supplemented with 10 ml of Eagle's basal vitamin solution (Gibco) at 37° C. The culture is grown to mid-log phase at which time 5-azacytidine is added to a final concentration of 25 μg/ml and 150 μCi [$^3$H]thymidine is also added, as in Example 4. The culture is incubated for an additional 1 hr at 37° C. Plasmid DNA containing 5-azacytidine and [$^3$H] thymidine is isolated by standard procedures, as described in Example 4.

B. Preparation of GST-Msp I Methylase Gene Fusion Product

*E. coli* SH210 cells transformed with plasmid pNTR2 are grown in LB media containing 50 μg/ml ampicillin (1 liter of culture at37° C.) . When the culture reaches mid-log phase, IPTG is added to a final concentration of 1 mM and the culture is incubated at 25° C. for 2 to 8 hr. Cells are harvested and lysed by sonication and the GST-Msp I gene fusion product is isolated by glutathione-Sepharose 4B affinity chromatography as described by C. Taylor et al. (1993), supra. The GST-Msp I gene fusion product is 647 residues and migrates as an approximately 70-kDa band on an 8–25% SDS-polyacrylamide gradient gel (See FIGS. 24A, 24B, 24C)

C. Reaction of GST-Msp I Gene Fusion Product with 5-Azacytidine-Containing pNRT2 Plasmid The product of Step (A), [$^3$H]thymidine labeled pNRT2 plasmid DNA containing 5-azacytidine (50 μg) is incubated with purified GST-Msp I gene fusion product under standard assay conditions (37° C., 20 mM Tris-HCl, pH 7.7), in the presence of S-adenosylmethionine as described in C. Taylor et al. (1993), supra. After 1 hr, the reaction mixture is loaded onto an equilibrated reduced glutathione-Sepharose 4B affinity column. After extensive washing in 20 mM Tris-HCl, 100 mM NaCl, pH 8.0. The column is eluted with reduced glutathione. Fractions are assayed for the presence of trichloroacetic acid precipitable [$^3$H] radioactivity indicating the presence of labeled plasmid DNA. Plasmid DNA containing the GST-Msp I conjugate is subjected to PCR amplification of the gene fusion construction construct using PCR primers 1 and 3 (SEQ ID NOS: 51 & 53), respectively.

D. Restriction Endonuclease Digestion

The GST-Msp I gene fusion product conjugate with pNRT2 is subjected to restriction endonuclease digestion with a restriction endonuclease such as Sau 3A (which will yield 23 DNA fragments), or Sca I (with sites at base pairs 832 and 1662) to yield DNA fragments conjugated to GST-Msp I. The DNA (GST-Msp I) fragments are subjected to native polyacrylamide gel electrophoresis to indicate the presence of bound protein. Other restriction enzymes can be chosen as well.

E. Detection of Both Protein and Nucleic Acid

DNA fragments may be electrophoresed on polyacrylamide gels and stained alternately with Coomassie blue or another protein stain and with ethidium bromide to indicate the presence of both nucleic acid and proteins.

Example 10

Effect of Varying Proportions of Cytosine to 5-Fluorocytosine on Growth of *E. coli* Strain SH210 Harboring pNTR2

*E. coli* SH210 transfected with pNRT2 were inoculated into six cultures of M9 minimal medium (5 ml). Each culture contained the following: 3.15 ml water; 1 ml of 5×M9 salts (64 g/l $NaHPO_4.7H_2O$, 15 g/l $KH_2PO_4$; 2.5 g/l NaCl, 5.0 g/l $NH_4Cl$), 100 μl 20% glucose; 0.5 ml 10×$MgSO_4$ (to final concentration of 1 mM); 55 μl 100×$CaCl_2$ (to final concentration of 10 μM), 55 μl 100×ampicillin (to final concentration of 50 μg/ml); 55 μl of 100×vitamin supplement (8.5 g/l NaCl, 100 mg/l biotin, 100 mg/l D-Ca pantothenate, 100 mg/l choline chloride, 100 mg/l folic acid, 200 mg/l i-inositol, 100 mg/l niacinamide, 100 mg/l pyridoxal hydrochloride, 10 mg/l riboflavin, and 100 mg/l thiamine hydrochloride), 55 μl arginine (to final concentration of 20 μg/ml), and 100 μl of 5 mg/l cytosine or fluorocytosine in the following proportions for each culture as given below. For 26-1, the proportion was 100% cytosine; for 26-2, 80% cytosine, 20% fluorocytosine, for 26-3, 60% cytosine, 40% fluorocytosine, for 26-4, 40% cytosine, 60% fluorocytosine, for 26-5, 20% cytosine, 80% fluorocytosine, and for 26-6, 0% cytosine, 100% fluorocytosine.

The cultures were inoculated with 100 μl inocula, and grown up approximately 5½ hours to mid-log phase ($A_{600}$ of about 0.6–0.8). At this point, the inducer isopropylthiogalactoside (IPTG) was added to 1 mM and the cultures were incubated on a roller drum at room temperature for about 11 hours. In some cases, as indicated below, samples of induced cultures were taken 2 hours after induction. An uninduced sample of each cell culture was stored as a pellet at −20° C. Triplicate samples were then taken of the induced cell cultures and stored as pellets at −20° C.

The base analogue 5-fluorocytosine, under these conditions, did not significantly inhibit the growth of the cells. The GST-Msp I gene fusion product is expressed at high levels in the presence of fluorocytosine in the medium.

Example 11

Effect of Varying Concentrations of 5-Fluorocytosine on Growth of Plasmid pNRT2 in *E. coli* Strain ER1647

Cultures were set up and inoculated of *E. coli* ER1647 transfected with plasmid pNRT2 in M9 minimal medium. The cultures were set up as in Example 10 except that arginine was replaced with tryptophan, methionine and histidine (each 55 μl to final concentration of 20 μg/ml), as well as uracil, adenine, and guanine (each 55 μl of to final concentration of 20 μg/ml). The cultures were inoculated after about 5½ hours, at $A_{600}$ of 1.0–1.2, isopropylthiogalactoside was added and the cells grown overnight on a roller drum as in Example 10; samples were taken as indicated. As in Example 10, six cultures were used, with proportions of fluorocytosine to cytosine varying from 0% to 100%. Again, the 5-fluorocytosine had little or no effect on growth of the cells, and the GST-Msp I gene fusion product is expressed at high levels in these cells under these conditions.

Example 12

Sodium Dodecyl Sulfate-Polyacrylamide Gel Electrophoresis of Cell Cultures of Examples 10 and 11 Grown with Varying Proportions of 5-Fluorocytosine The cell pellets from Examples 10 and 11 were run in sodium dodecyl sulfate-polyacrylamide gel electrophoresis to determine whether or not the glutathione S-transferase-Msp I methylase fusion protein was expressed. Sodium dodecyl sulfate-polyacrylamide gel electrophoresis was performed under standard conditions (U. K. Laemmli, "Cleavage of Structural Proteins During the Assembly of the Head of Bacteriophage T4," Nature 227:680 (1970)), using a gradient gel (8%–25%). Cell pellets were boiled 5 minutes in 200 μl of loading buffer (U. K. Laemmli (1970), supra). On gel 1 (FIG. 24A), the lanes were, from left to right: (1) ER1647 non-transformed, uninduced (from a previous experiment); (2) ER1647 non-transformed, induced; (3) culture 1 of Example 11 induced; (4) culture 2 of Example 4 uninduced; (5) culture 6 of Example 11 induced; (6) culture 6 of Example 11 taken 2 hours after induction; (7) culture 1 of Example 11 after overnight growth uninduced; and (8) a low molecular weight marker set. In gel B (FIG. 24B), the lanes were, from left to right: (1) the low molecular weight marker set; (2) culture 1 of Example 10 induced 2 hours after induction; (3) culture 1 of Example 10 uninduced; (4) culture 2 of Example 10 induced 2 hours after induction; (5) culture 3 of Example 10 induced 2 hours after induction; (6) culture 4 of Example 10 induced 2 hours after induction; (7) culture 5 of Example 10 induced 2 hours after induction; and (8) culture 6 of Example 10 induced 2 hours after induction. In the third gel, gel C (FIG. 24C), the lanes were, from left to right: (1) culture 2 of Example 11 induced 2 hours after induction; (2) culture 1 of Example 11 uninduced; (3) culture 3 of Example 11 induced 2 hours after induction; (4) culture 3 of Example 11 uninduced; (5) culture 4 of Example 11 induced 2 hours after induction; (6) culture 4 of Example 11 uninduced taken at the time of induction for the other cultures; (7) culture 5 of Example 11 induced 2 hours after induction; and (8) the low molecular weight marker.

The results show that the glutathione S-transferase-Msp I methylase is expressed in both SH210 and ER1647 cells transfected with pNRT2 plasmid. The 70-kDa GST-Msp I gene product is not present in significant quantities in uninduced cells. However, the GST-Msp I gene fusion product is expressed to high levels on minimal medium supplemented with varying proportions of 5-fluorocytosine and cytosine, including on 100% fluorocytosine.

Example 13

Growth of Transfected *E. coli* in 5-Fluorocytosine- and 5-Azacytosine-Containing Medium

*E. coli* SH210 transfected with plasmid pNRT2 was grown as in Example 10 in three cultures. In culture 1, cytosine was used; in culture 2, 5-fluorocytosine; and in culture 3, 5-azacytosine. The cells were grown 3 hours and induced with isopropylthiogalactoside. Samples were taken 2 hours after induction and after overnight growth after induction. Gel electrophoresis was performed as in Example 12. The results showed that 5-azacytosine could be substituted for 5-fluorocytosine or cytosine without interfering with either cell growth or expression of the 70-kDa gene fusion product.

Example 14

Isolation of a GST-Msp I Fusion Protein Conjugated to the 2 kb GST-Msp I Gene Sequence Prospective Example The *E. coli* expression plasmid pDE1, encoding the GST-Msp I gene fusion construct and the Msp I methylase conjugation element cloned into the EcoR I site of pDE1 AMCE, under IPTG-inducible transcriptional control, is transformed into SH210. SH210/pDElAMCE are grown in a 1-liter minimal medium culture containing 2% glucose, M9 salts, 10 μM $CaCl_2$, and 1% Eagle's Basal Medium (amino acids) without 5-azacytidine at 37° C. until the culture reaches mid-log phase. The culture is then cooled to 25° C. and IPTG is added to 1 mM final concentration; the induction is then continued for 2 hr at 25° C. At this point, 20–25 μg/ml of 5-azacytidine is added and the culture is incubated at 25° C. for an additional 2 hr to allow the incorporation of the nucleotide analog. Cells are harvested, gently lysed, and the pDElAMCE-Msp I/GST conjugates are isolated. The plasmid-gene fusion product conjugate is digested with restriction endonucleases EcoR I and Ssp I to release the approximately 2 kb fragment encoding the GST-Msp I construct linked to the methylase conjugation element through which the gene fusion product is conjugated. Protein and nucleic acid are identified by Coomassie blue and ethidium bromide staining. The gene-gene product conjugate can be substantially deproteinized by incubation with proteinase K at 65° C., and the purified fragment amplified by PCR using primers 1 (SEQ ID NO: 51) and 3 (SEQ ID NO: 53) to yield the GST-Msp I construct. The amplified GST-Msp I gene fusion fragment is subsequently cloned and sequenced.

ADVANTAGES OF THE PRESENT INVENTION

The present invention provides a rapid and efficient way of linking genetic information with proteins or peptides encoded by the genetic information. The Dlasmids and methods of the present invention are useful for screening and in vitro evolution, particularly for selecting receptors that have increased affinity for ligands. The plasmid-polypeptide linkages resulting from the processes of the invention, because they are covalent, are stable and allow manipulation of both the plasmid and polypeptide without breaking the linkages. This allows selection of mutated receptors by processes such as affinity chromatography under optimum conditions without risk of breaking the linkage between the plasmid and polypeptide and introducing errors.

The methods and plasmids of the present invention are well suited for use with nucleic acid amplification and sequencing techniques, such as the polymerase chain reaction technique.

In particular, the methods and plasmids of the present invention are suitable for developing mutations in glutathione S-transferase, an important target of chemotherapy in both cancer and Schistosoma parasitic infection.

Although the present invention has been described in considerable detail with regard to certain preferred versions thereof, other versions are possible. Therefore, the spirit and scope of the appended claims should not be limited to the descriptions of the preferred versions contained herein.

I claim:

1. A plasmid comprising:

(a) a gene fusion construct including a gene encoding a DNA methylase and a gene encoding a polypeptide determinant covalently joined, either directly or through a linker, the gene fusion construct encoding a gene fusion product including a cytosine (C-5) DNA methylase having a methyltransferase activity and a polypeptide determinant covalently joined thereto, either directly or through a peptide linker;

(b) a promoter operatively linked to the gene fusion construct for promoting transcription of the gene fusion construct as messenger RNA; and (c) a methylase conjugation element linked to the gene fusion construct either directly or through an intervening sequence, the methylase conjugation element including a methylase binding site having at least one copy of a nucleotide sequence including a cytidine suicide analog capable of irreversibly binding the cytosine (C-5) DNA methylase within the gene fusion product wherein said methylase binding site nucleotide sequence is a methylase substrate for said cytosine (C-5) DNA methylase.

2. The plasmid of claim 1 wherein the cytidine suicide analogue is selected from the group consisting of 2'-deoxy-5-fluorocytidine, 2'-deoxy-5-azacytidine, and 2'-pyrimidinone-1β-D-2-deoxyriboside.

3. The plasmid of claim 2 wherein the cytidine suicide analogue is 2'-deoxy-5-azacytidine.

4. The plasmid of claim 1 wherein the methylase conjugation element includes 1 to 50 copies of the methylase binding site having a specificity for the cytosine (C-5) DNA methylase.

5. The plasmid of claim 4 wherein the methylase conjugation element includes 3 to 20 copies of the methylase binding site.

6. The plasmid of claim 5 wherein the methylase conjugation element includes 4 to 6 copies of the methylase binding site.

7. The plasmid of claim 1 wherein the gene fusion construct has the DNA methylase gene covalently joined contiguously in-frame to the polypeptide determinant gene with a linking orientation selected from the group consisting of a first orientation with the 5'-terminus of the DNA methylase gene covalently joined to the 3'-terminus of the polypeptide determinant gene and a second orientation in which the 3'-terminus of the DNA methylase gene is covalently linked to the 5'-terminus of the polypeptide determinant gene.

8. The plasmid of claim 1 wherein the cytosine (C-5) DNA methylase is selected from the group consisting of Aqu I, Eag I, Eco 72 I, Hga I-1, Hga I-2, Hha I, Hpa II, Msp I, Nae I, Sss I, EcoR II, Hae III, NgoP II, Fnu DI, Fnu DII, Nla III, ScrF I, Sin I, Sso II, BsuF I, NgoM I, and Arabt, and wherein the nucleotide sequence of the methylase binding site of the methylase conjugation element serves as a substrate for the cytosine (C-5) DNA methylase.

9. The plasmid of claim 8 wherein the DNA methylase is selected from the group consisting of Msp I, Aqu I, and Hha I.

10. The plasmid of claim 1 wherein the gene fusion construct includes the linker for linking the DNA methylase gene to the polypeptide determinant gene, the linker encoding from 1 to 20 amino acids.

11. The plasmid of claim 10 wherein the peptide linker encoded by the gene fusion is from 5 to 20 amino acids and is of substantially α-helical secondary structure.

12. The plasmid of claim 11 wherein the amino acids of the peptide linker are selected from the group consisting of glycine, valine, isoleucine, leucine, and alanine.

13. The plasmid of claim 12 wherein the peptide linker is polyglycine.

14. The plasmid of claim 10 wherein the peptide linker has the sequence G-I-D-P-P (SEQ ID NO: 5).

15. The plasmid of claim 1 wherein the promoter is a prokaryotic promoter which promotes transcription in *Escherichia coli.*

16. The plasmid of claim 15 wherein the promoter is the tac promoter.

17. A plasmid comprising:

(a) a gene fusion construct including a DNA methylase gene and a polypeptide determinant gene covalently joined thereto, the DNA methylase gene covalently joined contiguously in-frame to the polypeptide determinant gene with a linking orientation selected from the group consisting of a first orientation in which the 5'-terminus of the DNA methylase gene is covalently joined to the 3'-terminus of the polypeptide determinant gene and a second orientation in which the 3'-terminus of the DNA methylase gene is covalently joined to the 5'-terminus of the polypeptide determinant gene, the DNA methylase gene and the polypeptide determinant gene being joined through a linker for linking the DNA methylase gene to the polypeptide determinant gene, the linker encoding from 1 to 20 amino acids, the DNA methylase gene being selected from the group consisting of genes coding for Aqu I, Eag I, Eco 72 I, Hga I-1, Hga I-2, Hha I, Hpa II, Msp I, Nae I, Sss I, EcoR II, Hae III, NgoP II, Fnu DI, Fnu DII, Nla III, ScrF I, Sin I, Sso II, BsuF I, NgoM I, and Arabt, the gene fusion construct encoding a gene fusion product including a cytosine (C-5) DNA methylase having a methyltransferase activity and a polypeptide determinant covalently joined thereto;

(b) a prokaryotic promoter operatively linked to the gene fusion for promoting transcription of the gene fusion as messenger RNA, wherein the promoter promotes transcription in *Escherichia coli*; and (c) a methylase conjugation element linked to the gene fusion construct, the methylase conjugation element including from 1 to 50 copies of a methylase binding site, the methylase binding site having a nucleotide sequence that is a substrate for the methyltransferase activity of the cytosine (C-5) DNA methylase, the nucleotide sequence including a cytidine suicide analogue selected from the group consisting of 2'-deoxy-5-fluorocytidine, 2'-deoxy-5-azacytidine, and 2-pyrimidinone-1-β-D-2-deoxyriboside wherein said methylase binding site nucleotide sequence is a methylase substrate for said cytosine (C-5) DNA methylase.

18. A plasmid-polypeptide determinant conjugate comprising a plasmid and a gene fusion product covalently conjugated to the plasmid via a pyrimidine moiety of a cytidine suicide analogue, the plasmid including:

(a) a gene fusion construct including a DNA methylase gene and a polypeptide determinant gene covalently joined thereto, the gene fusion construct encoding a gene fusion product including a cytosine (C-5) DNA methylase having a methyltransferase activity and a polypeptide determinant covalently joined thereto;

(b) a promoter operatively linked to the gene fusion construct for promoting transcription of the gene fusion construct as messenger RNA; and (c) a methylase conjugation element linked to the gene fusion construct, the methylase conjugation element including a methylase binding site having a nucleotide sequence including a cytidine suicide analogue which irreversibly binds the cytosine (C-5) DNA methylase of the gene fusion product and having a methylation specificity for the cytosine (C-5) DNA methylase wherein said methylase binding site nucleotide sequence is a methylase substrate for said cytosine (C-5) DNA methylase.

19. The plasmid-polypeptide determinant conjugate of claim 18 wherein the cytidine suicide analogue is selected from the group consisting of 2'-deoxy-5-fluorocytidine, 2'-deoxy-5-azacytidine, and 2-pyrimidinone-1-β-D-2-deoxyriboside.

20. The plasmid-polypeptide determinant conjugate of claim 19 wherein the cytidine suicide analogue is 2'-deoxy-5-azacytidine.

21. The plasmid-polypeptide determinant conjugate of claim 19 wherein the cytosine (C-5) DNA methylase encoded by the gene fusion construct and present within the gene fusion product is selected from the group consisting of Aqu I, Eag I, Eco 72 I, Hga I-1, Hga I-2, Hha I, Hpa II, Msp I, Nae I, Sss I, EcoR II, Hae III, NgoP II, Fnu DI, Fnu DII, Nla III, ScrF I, Sin I, Sso II, BsuF I, NgoM I, and Arabt, and wherein the nucleotide sequence of the methylase binding site of the methylase conjugation element in the plasmid serves as a substrate for the methyltransferase activity of the cytosine (C-5) DNA methylase.

22. The plasmid-polypeptide determinant conjugate of claim 18 wherein the gene fusion product further includes a linker encoded by the gene fusion construct, the linker linking the DNA methylase to the polypeptide determinant in the gene fusion product, the linker having from 1 to 20 amino acids.

23. A library comprising a plurality of plasmid-polypeptide determinant conjugates, each plasmid-polypeptide determinant conjugate including:

(a) an encoding plasmid molecule, each encoding plasmid molecule including:

(i) a gene fusion construct including a DNA methylase gene and a polypeptide determinant gene covalently joined thereto, the gene fusion construct encoding a gene fusion product including a cytosine (C-5) DNA methylase having a methyltransferase activity and a polypeptide determinant covalently joined thereto;

(ii) a promoter operatively linked to the gene fusion construct for promoting transcription of the gene fusion construct as messenger RNA; and (iii) a methylase conjugation element linked to the gene fusion construct, the methylase conjugation element including a methylase binding site having a nucleotide sequence including a cytidine suicide analogue which irreversibly binds the cytosine (C-5) DNA methylase of the gene fusion product wherein said methylase binding site nucleotide sequence is a methylase substrate for said cytosine (C-5) DNA methylase; and (b) the gene fusion product encoded by the gene fusion construct and covalently bound to the plasmid.

24. The library of claim 23 wherein the cytidine suicide analogue is selected from the group consisting of 2'-deoxy-5-fluorocytidine, 2'-deoxy-5-azacytidine, and 2-pyrimidinone-1-β-D-2-deoxyriboside.

25. The library of claim 24 wherein the cytidine suicide analogue is 2'-deoxy-5-azacytidine.

26. The library of claim 23 wherein the methylase conjugation element of the encoding plasmid molecule has from 1 to 50 copies of the methylase binding site which irreversibly binds the cytosine (C-5) DNA methylase of the gene fusion product and having a specificity for the cytosine (C-5) DNA methylase.

27. The library of claim 23 wherein within each gene fusion product, the DNA methylase is linked contiguously in-frame to the polypeptide determinant in a linking orientation selected from the group consisting of a first linking orientation in which the amino-terminus of the DNA methylase is linked to the carboxyl-terminus of the polypeptide determinant and a second linking orientation in which the carboxyl terminus of the DNA methylase is linked to the amino-terminus of the polypeptide determinant.

28. The library of claim 23 wherein the cytosine (C-5) DNA methylase is selected from the group consisting of Aqu I, Eag I, Eco 72 I, Hga I-1, Hga I-2, Hha I, Hpa II, Msp I, Nae I, Sss I, EcoR II, Hae III, NgoP II, Fnu DI, Fnu DII, Nla III, ScrF I, Sin I, Sso II, BsuF I, NgoM I, and Arabt, and wherein the methylase binding site in the methylase conjugation element of the plasmid in each plasmid-polypeptide determinant conjugate has a nucleotide sequence which irreversibly binds the DNA methylase.

29. The library of claim 28 wherein the cytosine (C-5) DNA methylase is selected from the group consisting of Msp I, Aqu I, and Hha I.

30. The library of claim 23 wherein each of the polypeptide determinant genes within the plurality of plasmid-polypeptide determinant conjugates is derived from a single parent polypeptide determinant gene by random mutagenesis.

31. The library of claim 30 wherein the parent polypeptide determinant gene is the wild-type glutathione S-transferase gene from *Schistosoma japonicum.*

32. The library of claim 23 wherein each gene fusion product further includes a linker for linking the cytosine (C-5) DNA methylase to the polypeptide determinant, the linker having from 1 to 20 amino acids.

33. A library comprising a plurality of plasmid-polypeptide determinant conjugates, each plasmid-polypeptide determinant conjugate including:

(a) an encoding plasmid molecule including:

(i) a gene fusion construct including a DNA methylase gene and a polypeptide determinant gene covalently joined thereto, the DNA methylase gene covalently joined contiguously in-frame to the polypeptide determinant gene with a linking orientation selected from the group consisting of a first linking orientation in which the 5'-terminus of the DNA methylase gene is covalently joined to the 3'-terminus of the polypeptide determinant gene and a second linking orientation in which the 3'-terminus of the DNA methylase is covalently joined to the 5'-terminus of the polypeptide determinant gene, the DNA methylase gene selected from the group consisting of genes coding for Aqu I, Eag I, Eco 72 I, Hga I-1, Hga I-2, Hha I, Hpa II, Msp I, Nae I, Sss I, EcoR II, Hae III, NgoP II, Fnu DI, Fnu DII, Nla III, ScrF I, Sin I, Sso II, BsuF I, NgoM I, and Arabt, the gene fusion construct encoding a gene fusion product including a cytosine (C-5) DNA methylase having a methyltransferase activity and a polypeptide determinant covalently joined thereto;

(ii) a promoter operatively linked to the gene fusion construct for promoting transcription of the gene fusion construct as messenger RNA; and (iii) a methylase conjugation element linked to the gene fusion construct, the methylase conjugation element including a methylase binding site which serves as a substrate for the DNA methylase encoded by the DNA methylase gene, the methylase conjugation element having 1 to 50 copies of the methylase binding site, each methylase binding site including a nucleotide sequence including a cytidine suicide analogue selected from the group consisting of 2'-deoxy-5-fluorocytidine, 2'-deoxy-5-azacytidine, and 2'-pyrimidinone-1-β-D-2-deoxyriboside wherein said methylase binding site nucleotide sequence is a methylase substrate for said cytosine (C-5) DNA methylase; and (b) said encoded gene fusion product covalently bound to said analogue.

34. The library of claim 33 wherein the polypeptide determinant gene in each of the plurality of plasmid-polypeptide determinant conjugates is derived from a parent polypeptide determinant gene by random mutagenesis.

35. The library of claim 34 wherein the parent polypeptide determinant gene encodes a protein selected from the group consisting of glutathione S-transferase, estrogen receptor, triose phosphate isomerase, thrombin, plasminogen, tissue plasminogen activator, streptokinase, human insulin, erythropoietin, thrombopoietin, a fibrinogen type III domain or a protein including a fibrinogen type III domain, a DNA binding domain or a protein including a DNA binding domain, a helix-turn-helix DNA binding domain or a protein including a helix-turn-helix DNA binding domain, interleukin, HIV reverse transcriptase, HIV protease, renin, elastase, subtilisin, α-lytic protease, hirudin, omatin, kistin, and eglin C.

36. A method for obtaining a nucleic acid segment encoding a polypeptide, the polypeptide having at least one property altered from a wild-type polypeptide, comprising the steps of:

(a) obtaining a nucleic acid segment encoding a wild-type polypeptide;

(b) subjecting the nucleic acid segment encoding the wild-type polypeptide to random mutagenesis to generate a plurality of mutagenized nucleic acid segments;

(c) constructing a library of plasmids from the plurality of mutagenized nucleic acid segments, each plasmid within the library of plasmids including:

(1) a gene fusion construct including a DNA methylase gene and one of the plurality of mutagenized nucleic acid sequences covalently joined thereto, the gene fusion construct encoding a gene fusion product including a cytosine (C-5) DNA methylase having a methyltransferase activity and a polypeptide determinant covalently joined thereto;

(2) a promoter operatively linked to the gene fusion construct for promoting transcription of the gene fusion construct as messenger RNA; and (3) a methylase conjugation element linked to the gene fusion construct, the methylase conjugation element including a methylase binding site having a nucleotide sequence including a cytidine suicide analog which irreversibly binds to the cytosine (C-5) DNA methylase of the gene fusion product wherein said methylase binding site nucleotide sequence is a methylase substrate for said cytosine (C-5) DNA methylase;

(d) causing expression of the gene fusion product from each plasmid of the library of plasmids;

(e) forming an irreversible joining of the gene fusion product to the plasmid encoding the gene fusion product for each plasmid of the library of plasmids, thereby forming a library of plasmid-polypeptide determinant conjugates;

(f) isolating a plasmid-polypeptide determinant conjugate from the library of plasmid-polypeptide determinant conjugates that binds a predetermined target moiety in a manner such that only plasmid-polypeptide determinant conjugates that have a property altered when compared to the wild-type polypeptide bind the target moiety;

(g) deproteinizing the plasmid-polypeptide determinant conjugate obtained in step (f) to form a purified plasmid encoding a polypeptide determinant having an altered property; and (h) isolating from the purified plasmid of step (g) a nucleic acid segment that encodes a polypeptide determinant having at least one property altered when compared with the wild-type polypeptide determinant.

37. The method of claim 36 wherein the step of isolating the plasmid-polypeptide determinant conjugate that binds a predetermined target moiety in such a way that only the polypeptide determinant with at least one altered property binds the target moiety comprises the step of binding the plasmid-polypeptide determinant conjugate to a ligand under conditions such that the wild-type polypeptide determinant does not bind to the ligand and only polypeptide determinant conjugates with increased affinity for the ligand bind to the ligand.

38. The method of claim 37 wherein the ligand is glutathione.

39. The method of claim 37 further comprising:

(i) subjecting the nucleic acid segment of step (h) encoding the polypeptide determinant with at least one altered property to further random mutagenesis to produce a plurality of doubly mutagenized nucleic acid segments;

(j) constructing a second library of plasmids, each plasmid comprising:

(1) a gene fusion construct including a DNA methylase gene and one of the plurality of doubly mutagenized polypeptide determinant genes covalently joined thereto, the gene fusion construct encoding a gene fusion product including a cytosine (C-5) DNA methylase having a methyltransferase activity and a polypeptide determinant covalently joined thereto;

(2) a promoter operatively linked to the gene fusion construct for promoting transcription of the gene fusion as messenger RNA; and (3) a methylase conjugation element linked to the gene fusion construct, the methylase conjugation element including a methylase binding site having a nucleotide sequence including a cytidine suicide analog which irreversibly binds to the cytosine (C-5) DNA methylase of the gene fusion product wherein said methylase binding site nucleotide sequence is a methylase substrate for said cytosine (C-5) DNA methylase;

(k) causing expression of the gene fusion product from each plasmid of the second library of plasmids;

(l) forming an irreversible covalent joining of each of the gene fusion products to the plasmid encoding for the gene fusion product to form a second library of plasmid-polypeptide determinant conjugates;

(m) isolating a plasmid-polypeptide determinant conjugate from the second library of plasmid-polypeptide determinant conjugates that binds a predetermined target moiety in such a way that neither the wild-type protein determinant nor the protein determinant encoded by the nucleic acid segment of step (h) binds the predetermined target moiety; and (n) deproteinizing the plasmid-polypeptide determinant conjugate obtained in step (m) to form a purified plasmid encoding a doubly mutagenized polypeptide determinant.

40. The method of claim 39 wherein the polypeptide determinant encoded by the doubly mutagenized nucleic acid segment binds a ligand with an increased affinity so that the isolation of step (m) occurs under conditions such that neither the wild-type polypeptide moiety nor the polypeptide moiety encoded by the nucleic acid segment of step (h) binds.

41. The method of claim 36 wherein step (h) comprises the step of amplifying the nucleic acid segment encoding the polypeptide determinant with the at least one altered property by a sequence-specific primer-based amplification method employing at least two primers.

42. The method of claim 41 wherein the sequence-specific primer-based nucleic acid amplification technique is the polymerase chain reaction technique.

43. The method of claim 36 wherein the polypeptide determinant gene encodes a protein selected from the group consisting of glutathione S-transferase, estrogen receptor, triose phosphate isomerase, thrombin, plasminogen, tissue plasminogen activator, streptokinase, human insulin, erythropoietin, thrombopoietin, a fibrinogen type III domain or a protein including a fibrinogen type III domain, a DNA binding domain or a protein including a DNA binding domain, a helix-turn-helix DNA binding domain or a protein including a helix-turn-helix DNA binding domain, interleukin, HIV reverse transcriptase, HIV protease, renin, elastase, subtilisin, $\alpha$-lytic protease, hirudin, omatin, kistin, and eglin C.

44. The method of claim 43 wherein the wild-type polypeptide determinant gene encodes glutathione S-transferase.

45. A method for obtaining a nucleic acid segment encoding a polypeptide, the polypeptide having at least one property altered from a wild-type polypeptide, comprising the steps of:

(a) obtaining a nucleic acid segment encoding the wild-type polypeptide;

(b) subjecting the nucleic acid segment encoding the wild-type polypeptide to random mutagenesis to generate a plurality of mutagenized nucleic acid segments;

(c) constructing a library of plasmids from the plurality of mutagenized nucleic acid segments, each plasmid within the library of plasmids including:

(i) a gene fusion construct including a DNA methylase gene and one of the plurality of mutagenized nucleic acid sequences covalently joined thereto, the gene fusion construct encoding a gene fusion product including a cytosine (C-5) DNA methylase having a methyltransferase activity and a polypeptide determinant covalently joined thereto;

(ii) a promoter operatively linked to the gene fusion construct for promoting transcription of the gene fusion construct as messenger RNA; and (iii) a methylase conjugation element linked to the gene fusion construct, the methylase conjugation element including a methylase binding site having a nucleotide sequence including a cytidine suicide analog which irreversibly binds to the cytosine (C-5) DNA methylase of the gene fusion product wherein said methylase binding site nucleotide sequence is a methylase substrate for said cytosine (C-5) DNA methylase;

(d) causing expression of the gene fusion product from each plasmid of the library of plasmids;

(e) forming an irreversible joining of the gene fusion product to the plasmid encoding the gene fusion product for each plasmid of the library of plasmids, thereby forming a library of plasmid-polypeptide determinant conjugates;

(f) isolating a plasmid-polypeptide determinant conjugate from the library of plasmid-polypeptide determinant conjugates that binds a predetermined target moiety in a manner such that only plasmid-polypeptide determinant conjugates that have a property altered when compared to the wild-type polypeptide bind the target moiety;

(g) isolating from the purified plasmid of step (f) a nueleic acid segment that encodes a polypeptide determinant having at least one property altered when compared with the wild-type polypeptide determinant by amplifying the nucleic acid segment encoding the polypeptide determinant with the at least one altered property by a sequence-specific primer-based amplification method employing at least two primers.

46. The method of claim 45 wherein the sequence-specific primer-based amplification method employing at least two primers is the polymerase chain reaction (PCR) technique.

47. A plasmid-polypeptide determinant conjugate comprising a plasmid and a gene fusion product covalently conjugated to the plasmid via a pyrimidine moiety of a cytidine suicide analogue, the plasmid including:

(a) a gene fusion construct including a DNA methylase gene and a polypeptide determinant gene covalently joined thereto, the gene fusion construct encoding said gene fusion product including a cytosine (C-5) DNA methylase having a methyltransferase activity and a polypeptide determinant covalently joined thereto;

(b) a promoter operatively linked to the gene fusion construct for promoting transcription of the gene fusion construct as messenger RNA; and (c) a framework region including at least one methylase binding site having a nucleotide sequence including a cytidine suicide analogue which irreversibly binds the cytosine (C-5) DNA methylase of the gene fusion product and having a methylation specificity for the cytosine (C-5) DNA methylase wherein said methylase binding site nucleotide sequence is a methylase substrate for said cytosine (C-5) DNA methylase.

48. The plasmid-polypeptide determinant conjugate of claim 47 wherein the cytidine suicide analogue is selected from the group consisting of 2'-deoxy-5-fluorocytidine, 2'-deoxy-5-azacytidine, and 2-pyrimidinone-1-β-D-2-deoxyriboside.

49. The plasmid-polypeptide determinant conjugate of claim 48 wherein the cytidine suicide analogue is 2'-deoxy-5-azacytidine.

50. The plasmid-polypeptide determinant conjugate of claim 47 wherein the cytosine (C-5) DNA methylase encoded by the gene fusion construct and present within the gene fusion product is selected from the group consisting of Aqu I, Eag I, Eco 72 I, Hga I-1, Hga I-2, Hha I, Hpa II, Msp I, Nae I, Sss I, EcoR II, Hae III, NgoP II, Fnu DI, Fnu DII, Nla III, ScrF I, Sin I, Sso II, BsuF I, NgoM I, and Arabt, and wherein the nucleotide sequence of the methylase binding site of the framework region in the plasmid serves as a substrate for the methyltransferase activity of the cytosine (C-5) DNA methylase.

51. The plasmid-polypeptide determinant conjugate of claim 47 wherein the gene fusion product further includes a linker encoded by the gene fusion construct, the linker linking the DNA methylase to the polypeptide determinant in the gene fusion product, the linker having from 1 to 20 amino acids.

* * * * *